United States Patent
Sellman et al.

(10) Patent No.: US 9,527,905 B2
(45) Date of Patent: Dec. 27, 2016

(54) **ANTIBODIES THAT SPECIFICALLY BIND *STAPHYLOCOCCUS AUREUS* ALPHA TOXIN AND METHODS OF USE**

(75) Inventors: Bret Sellman, Gaithersburg, MD (US); Christine Tkaczyk, Gaithersburg, MD (US); Lei Hua, Gaithersburg, MD (US); Partha Chowdhury, Gaithersburg, MD (US); Reena Varkey, Gaithersburg, MD (US); Melissa Damschroder, Gaithersburg, MD (US); Li Peng, Gaithersburg, MD (US); Vaheh Oganesyan, Gaithersburg, MD (US); Jamese Johnson Hilliard, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 204 days.

(21) Appl. No.: 13/983,804

(22) PCT Filed: Feb. 7, 2012

(86) PCT No.: PCT/US2012/024201
§ 371 (c)(1),
(2), (4) Date: Nov. 21, 2013

(87) PCT Pub. No.: WO2012/109285
PCT Pub. Date: Aug. 16, 2012

(65) Prior Publication Data
US 2014/0072577 A1    Mar. 13, 2014

Related U.S. Application Data

(60) Provisional application No. 61/440,581, filed on Feb. 8, 2011.

(51) Int. Cl.
| | | |
|---|---|---|
| *A61K 51/00* | (2006.01) |
| *C07K 16/12* | (2006.01) |
| *G01N 33/569* | (2006.01) |
| *A61K 38/14* | (2006.01) |
| *A61K 39/40* | (2006.01) |
| *A61K 45/06* | (2006.01) |
| *A61K 39/00* | (2006.01) |

(52) U.S. Cl.
CPC .......... *C07K 16/1271* (2013.01); *A61K 38/14* (2013.01); *A61K 39/40* (2013.01); *A61K 45/06* (2013.01); *G01N 33/56938* (2013.01); *A61K 2039/505* (2013.01); *C07K 2299/00* (2013.01); *C07K 2317/21* (2013.01); *C07K 2317/24* (2013.01); *C07K 2317/34* (2013.01); *C07K 2317/56* (2013.01); *C07K 2317/76* (2013.01); *C07K 2317/90* (2013.01); *C07K 2317/92* (2013.01); *G01N 2333/31* (2013.01); *G01N 2800/20* (2013.01); *G01N 2800/44* (2013.01); *G01N 2800/709* (2013.01)

(58) Field of Classification Search
None
See application file for complete search history.

(56) References Cited

U.S. PATENT DOCUMENTS

| | | | |
|---|---|---|---|
| 6,596,541 B2 | 7/2003 | Murphy et al. | |
| 2003/0226155 A1 | 12/2003 | Sadeghi et al. | |
| 2005/0226876 A1 | 10/2005 | Graus et al. | |
| 2006/0093610 A1 | 5/2006 | Lang et al. | |
| 2008/0152587 A1 | 6/2008 | Zhou et al. | |
| 2009/0053235 A1* | 2/2009 | Taylor ................. | A61K 39/085 424/150.1 |
| 2009/0155164 A1 | 6/2009 | Brazel et al. | |

FOREIGN PATENT DOCUMENTS

| | | |
|---|---|---|
| CN | 1513874 | 7/2004 |
| EP | 2280787 A1 | 7/2010 |
| WO | WO 2009029831 A1 | 5/2009 |
| WO | WO 2010003108 A2 | 7/2010 |
| WO | WO 2014074540 A2 | 5/2014 |

OTHER PUBLICATIONS

Ragle et al. (Infection and Immunity vol. 77, No. 7, pp. 2712-2718).*
Bhakdi, S., et al., "Alpha-Toxin of *Staphylococcus aureus*," Microbiological Reviews 55(4): 733-751 (1991).
Brown, M., et al., "Tolerance to Single, but Not Multiple, Amino Acid Replacements in Antibody VH CDR2: A Means of Minimizing B Cell Wastage from Somatic Hypermutation?" The Journal of Immunology 156:3285-3291 (1996).
Gouaux, E., et al., "α-Hemolysin, γ-hemolysin, and leukocidin from *Staphylococcus aureus*: Distant in sequence but similar in structure" Protein Science 6: 2631-2635 (1997).
Hilliard, J., et al., "Anti-Alpha-Toxin Monoclonal Antibody and Antibiotic Combination Therapy Improves Disease Outcome and Accelerates Healing in a *Staphylococcus aureus* Dermonecrosis Model" Antimicrobial Agents and Chemotherapy 59(1): 299-309 (2015).
Hua, L., et al., "Assessment of an Anti-Alpha-Toxin Monoclonal Antibody for Prevention and Treatment of *Staphylococcus aureus*-Induced Pneumonia" Antimicrobial Agents and Chemotherapy 58(2): 1108-1117 (2014).
Meesters, C., et al., "Structural characterization of the α-hemolysin monomer from *Staphylococcus aureus*" Proteins 75: 118-126 (2009).
Oganesyan, V., et al., "Mechanisms of Neutralization of a Human Anti-α-toxin Antibody" The Journal of Biological Chemistry 289(43): 29874-29880 (2014).
Ragle, B., et al., "Anti-Alpha-Hemolysin Monoclonal Antibodies Mediate Proection against *Staphylococcus aureus* Pneumonia" Infection and Immunity 77(7): 2712-2718 (2009).
Song, L., et al., "Structure of Staphylococcal α-Hemolysin, a Heptameric Transmembrane Pore" Science 274: 1859-1866 (1996).
Tkaczyk, C., et al., "Identification of Anti-Alpha Toxin Monoclonal Antibodies That Reduce the Severity of *Staphylococcus aureus* Dermonecrosis and Exhibit a Correlation between Affinity and Potency" Clinical and Vaccine Immunology 19(3): 377-385 (2012).
Wilke, G., et al., Role of a disintegrin and metalloprotease 10 in *Staphylococcus aureus* α-hemolysin-mediated cellular injury PNAS 107(30): 13473-13478 (2010).

* cited by examiner

Primary Examiner — Gary Nickol
Assistant Examiner — Khatol Shahnan Shah

(57) ABSTRACT

Herein provided are compositions, methods of manufacture and methods of use pertaining to anti-alpha toxin antibodies and fragments.

9 Claims, 29 Drawing Sheets

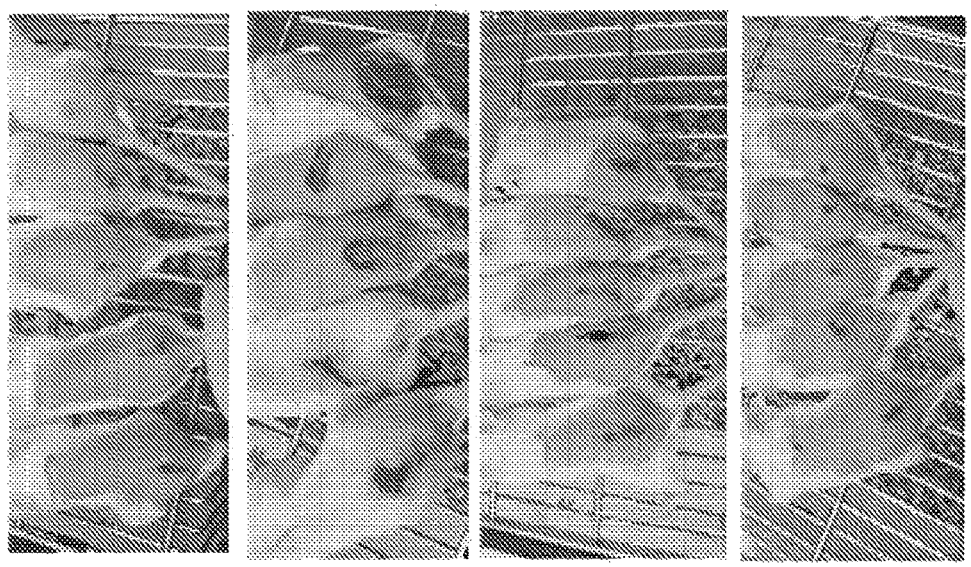
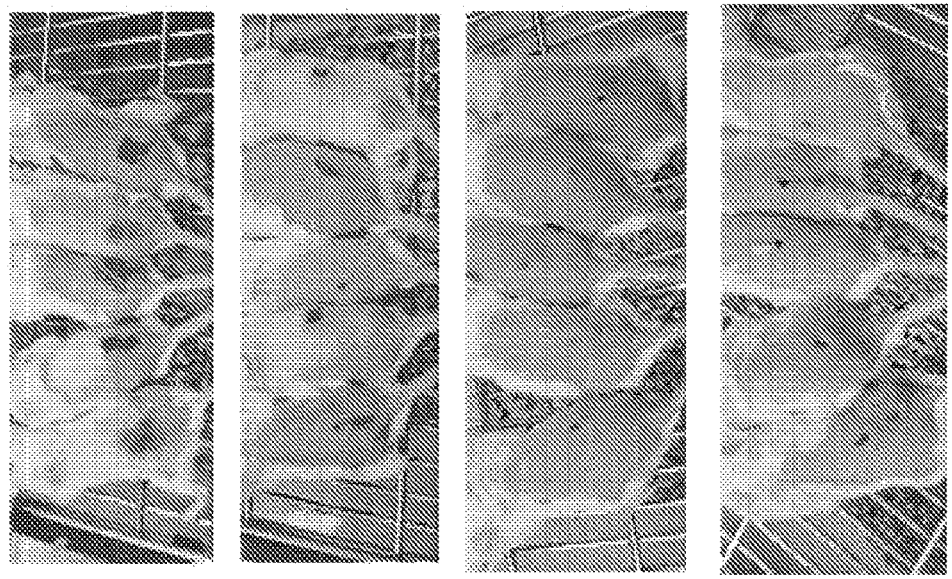
Figure 3A
2A3.1*
11D12.1
15B6.3
28F6.1*
R347
10A7.5*
12B8.19*
25E9.1*
* p-value = 0.0079

```
Alpha Toxin  ADSDINIKTGTTDIGSNTTVKTGDLVTYDKENGMHKKVFYSFDDKNHNKKLLVIRTKGT     60
LukF-PV      --AQHITPVSEKKVDDKITLYKTTATSDSDKLKISQILTFNFIKDKSYDKDTLILKAAGN     58
                *:  *:.:..:.:   *.  :      . .::  .:.:.:**.:**::  *::::.*.

Alpha Toxin  IAGQYRVYSEEGANKSGLAWPSAFKVQLQLPDNEVAQISDYYPRNSIDTKEYMSTLTYGF    120
LukF-PV      IYSGYTKPNPKDTISSQFYWGSKYNISINSDSVNVVDYAPKNQNEEFQVQQTVGYSY     118
             * . *.:  . :..*.   :.::::  *  :::. **. :* :.*: :*: :   . :

Alpha Toxin  NGNVTGDDTGKIGGLIGANVSIGHTLKYVQPDFKTILESPT-DKKVGWKVIFNNMVNQNW    179
LukF-PV      GGDIN-ISNGLSGGGNGS-KSESETINYKQESYRTSLDKRTNFKKIGWDVEAHKIMNNGW    176
              *:.. ...* *** :*.  . * *:: *  ::: .* * ::*.:**.* :*:::*.*

Alpha Toxin  GPYDRDSWNPVYGNQLFMKTRNGSMKAADNFLDENKASSLLSSGFSPDFATVITMDRKAS    239
LukF-PV      GPYGRDSYHSTYGNEMFLGSRQSNLNAGQNFLEYHKMPVLSRGN FNPEFGVLSRKQAA    236
             *** ***::..***::*:.: .*::.* :***: :*. .**.    :*:..:: *: **

Alpha Toxin  KQQTNIDVIYERVRDDYQLHWTSTNWKGTNTKDKWIDRSSERYKIDWEKEEMTN-----    293
LukF-PV      KK-SKITVTYQREMDRYTNFWNQLHWIGNNYKDENRATHTSIYEVDWENHTVKLIDTQSK    295
              : . :.*  : *:*     ::** ..*  **:     :*:.**::..

Alpha Toxin  ---          SEQ ID NO:39
LukF-PV      EKN P 299    SEQ ID NO:93
```

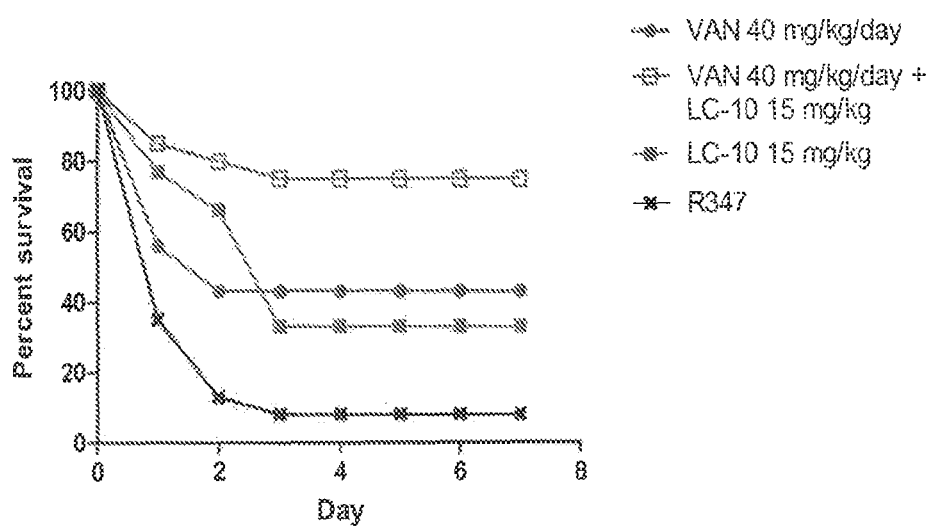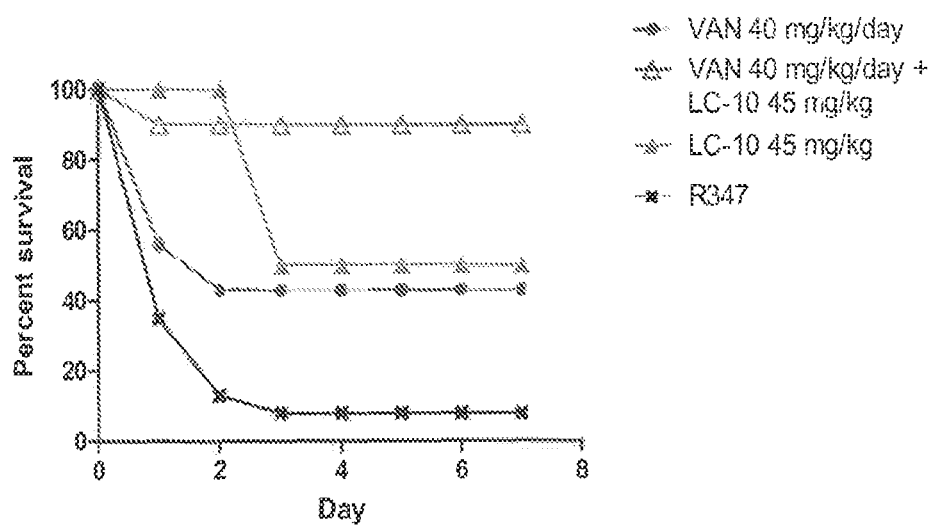
FIGURE 26

SEQUENCE LISTING

<160> NUMBER OF SEQ ID NOS: 92

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 1

Arg Ala Ser Gln Ser Ile Ser Ser Trp Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Ala Ser Ser Leu Glu Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Tyr Asn Ser Tyr Trp Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Gly Ile Arg Asn Asp Leu Gly
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ala Ser Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Gln Asp Tyr Asn Tyr Pro Trp Thr
1               5

<210> SEQ ID NO 7
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 7

Ser Tyr Asp Met His
1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ile Gly Thr Ala Gly Asp Thr Tyr Tyr Pro Gly Ser Val Lys Gly
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Asn Tyr Ser Ser Thr Gly Gly Tyr Tyr Gly Met Asp Val
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Tyr Asp Met His
1               5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Ile Gly Thr Asp Gly Asp Thr Tyr Tyr Pro Gly Ser Val Lys Gly
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Tyr Ser Ser Ser Asn His Tyr Asn Gly Met Asp Val
1               5                   10
```

```
<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Tyr Ala Met Thr
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Ile Ser Gly Ser Gly Gly Ser Thr Tyr Tyr Ala Asp Ser Val Lys
1               5                   10                  15

Gly

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Gly Arg Gln Val Glu Asp Tyr Tyr Tyr Tyr Tyr Gly Met Asp Val
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Arg Tyr Ser Pro Thr Gly His Tyr Met Gly Met Asp Val
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Ile Asp Thr Ala Gly Asp Thr Tyr Tyr Pro Gly Ser Val Lys Gly
1               5                   10                  15

<210> SEQ ID NO 18
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 18

Asp Arg Tyr Ser Gly Asn Phe His Tyr Asn Gly Met Asp Val
1               5                   10

<210> SEQ ID NO 19
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 20
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Leu Asn Ser Leu Arg Ala Gly Asp Thr Ala Val Tyr Phe Cys Ala
                85                  90                  95

Arg Asp Asn Tyr Ser Ser Thr Gly Gly Tyr Tyr Gly Met Asp Val Trp
            100                 105                 110

Gly Gln Gly Thr Thr Val Thr Val Ser Ser
        115                 120

<210> SEQ ID NO 21
<211> LENGTH: 106
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 22
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Thr Gly Lys Gly Leu Glu Trp Val
        35                  40                  45

Ser Val Ile Gly Thr Asp Gly Asp Thr Tyr Tyr Pro Gly Ser Val Lys
50                  55                  60

Gly Arg Phe Ile Ile Ser Arg Glu Asn Ala Lys Asn Ser Leu Tyr Leu
65                  70                  75                  80

Glu Met Asn Ser Leu Arg Ala Gly Asp Thr Ala Val Tyr Tyr Cys Ala
                85                  90                  95

Arg Asp Arg Tyr Ser Ser Ser Asn His Tyr Asn Gly Met Asp Val Trp
            100                 105                 110

Gly Gln Gly Thr Thr Val Thr Val Ser Ser
        115                 120

<210> SEQ ID NO 23
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30
```

```
Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 24
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asp Met His Trp Val Arg Gln Ala Thr Gly Lys Gly Leu Glu Trp Val
        35                  40                  45

Ser Val Ile Gly Thr Asp Gly Asp Thr Tyr Tyr Pro Gly Ser Val Lys
    50                  55                  60

Gly Arg Phe Ile Ile Ser Arg Glu Asn Ala Lys Asn Ser Leu Tyr Leu
65                  70                  75                  80

Glu Met Asn Ser Leu Arg Ala Gly Asp Thr Ala Val Tyr Tyr Cys Ala
                85                  90                  95

Arg Asp Arg Tyr Ser Ser Ser Asn His Tyr Asn Gly Met Asp Val Trp
            100                 105                 110

Gly Gln Gly Thr Thr Val Thr Val Ser Ser
        115                 120

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95
```

Thr Phe Gly Gln Gly Thr Lys Val Glu Ile Lys
            100                 105

<210> SEQ ID NO 26
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Arg Gln Val Glu Asp Tyr Tyr Tyr Tyr Gly Met
            100                 105                 110

Asp Val Trp Gly Gln Gly Thr Thr Val Thr Val Ser Ser
        115                 120                 125

<210> SEQ ID NO 27
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 28
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Thr | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Asp | Met | His | Trp | Val | Arg | Gln | Ala | Thr | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Val | Ile | Asp | Thr | Ala | Gly | Asp | Thr | Tyr | Tyr | Pro | Gly | Ser | Val | Lys |
|---|---|---|---|---|---|---|---|---|---|---|---|---|---|---|---|
| 50 | | | | | 55 | | | | | 60 | | | | | |

| Gly | Arg | Phe | Thr | Ile | Ser | Arg | Glu | Asn | Ala | Lys | Asn | Ser | Leu | Tyr | Leu |
|---|---|---|---|---|---|---|---|---|---|---|---|---|---|---|---|
| 65 | | | | | 70 | | | | | 75 | | | | | 80 |

| Gln | Met | Asn | Ser | Leu | Arg | Ala | Gly | Asp | Thr | Ala | Val | Tyr | Tyr | Cys | Val |
|---|---|---|---|---|---|---|---|---|---|---|---|---|---|---|---|
| | | | | 85 | | | | | 90 | | | | | 95 | |

| Arg | Asp | Arg | Tyr | Ser | Gly | Asn | Phe | His | Tyr | Asn | Gly | Met | Asp | Val | Trp |
|---|---|---|---|---|---|---|---|---|---|---|---|---|---|---|---|
| | | | 100 | | | | | 105 | | | | | 110 | | |

| Gly | Gln | Gly | Thr | Thr | Val | Thr | Val | Ser | Ser |
|---|---|---|---|---|---|---|---|---|---|
| | | 115 | | | | | 120 | | |

<210> SEQ ID NO 29
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaaactcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attggacgtt cggccaaggg   300
accaaggtgg aaatcaaa                                                  318
```

<210> SEQ ID NO 30
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
gaggtgcagc tggtggagtc tgggggaggc ttggtacagc ctgggggtc cctgagactc     60
tcctgtgcag cctctggatt caccttcagt agctacgaca tgcactgggt ccgccaagct   120
acaggaaaag gtctggagtg gtctcaggt attggcactg ctggtgacac atattatcca   180
ggctccgtga agggccgatt caccatctcc agagaaaatg ccaagaactc cttgtatctt   240
caattgaaca gcctgagagc cggggacacg gctgtgtact tctgtgcaag agacaattat   300
agcagcaccg ggggtacta cggtatggac gtctggggcc aagggaccac ggtcaccgtc   360
tcctca                                                              366
```

<210> SEQ ID NO 31
<211> LENGTH: 318
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 31

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaaactcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attggacgtt cggccaaggg   300
accaaggtgg aaatcaaa                                                 318
```

<210> SEQ ID NO 32
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
gaggtgcagc tggtggagtc tgggggaggc ttggtacagc ctggggggtc cctgagactc    60
tcctgtgcag cctctggatt caccttcagt aggtacgaca tgcactgggt ccgccaagct   120
acaggaaaag gtctggagtg ggtctcagtt attggtactg atggtgacac atactatcca   180
ggctccgtga agggccgatt catcatctcc agagaaaatg ccaagaactc cttgtatctt   240
gaaatgaaca gcctgagagc cggggacacg gctgtgtatt actgtgcaag agatcggtat   300
agcagctcga accactacaa cggtatggac gtctggggcc aagggaccac ggtcaccgtc   360
tcctca                                                              366
```

<210> SEQ ID NO 33
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaaggtcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attggacgtt cggccaaggg   300
accaaggtgg aaatcaaa                                                 318
```

<210> SEQ ID NO 34
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
gaggtgcagc tggtggagtc tgggggaggc ttggtacagc ctggggggtc cctgagactc    60
```

```
tcctgtgcag cctctggatt caccttcagt aggtacgaca tgcactgggt ccgccaagct      120
acaggaaaag gtctggagtg ggtctcagtt attggtactg atggtgacac atactatcca      180
ggctccgtga agggccgatt catcatctcc agagaaaatg ccaagaactc cttgtatctt      240
gaaatgaaca gcctgagagc cggggacacg gctgtgtatt actgtgcaag agatcggtat      300
agcagctcga accactacaa cggtatggac gtctggggcc aagggaccac ggtcaccgtc      360
tcctca                                                                 366

<210> SEQ ID NO 35
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gccatccaga tgacccagtc tccatcctcc ctgtctgcat ctgtaggaga cagagtcacc       60
atcacttgcc gggcaagtca gggcattaga aatgatttag ctggtatca gcagaaacca      120 gggaaagccc ctaagctcct gatctatgat gcatccagtt tacaaagtgg ggtcccatca      180
aggttcagcg gcagtggatc tggcacagat ttcactctca ccatcagcag cctgcagcct      240
gaagattttg caacttatta ctgtctacaa gattacaatt acccgtggac gttcggccaa      300
gggaccaagg tggaaatcaa a                                                321

<210> SEQ ID NO 36
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gaggtgcagc tgttggagtc tgggggaggc ttggtacagc ctgggggtc cctgagactc       60 tcctgtgcag cctctggatt cacctttagc agctatgcca tgacctgggt ccgccaggct      120
ccagggaagg ggctggaatg ggtctcagtt attagtggta gtggtggtag cacatactac      180
gcagactccg tgaagggccg gttcaccgtc tccagagaca attccaagaa cacgctgtat      240
ctgcaaatga acagcctgag agccgaggac acggccgtat attactgtgc gaaagatggg      300
aggcaggtcg aggattacta ctactactac ggtatggacg tctggggcca agggaccacg      360
gtcaccgtct cctca                                                       375

<210> SEQ ID NO 37
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gacatccaga tgacccagtc tccttccacc ctgtctgcat ctgtaggaga cagagtcacc       60
atcacttgcc gggccagtca gagtattagt agctggttgg cctggtatca gcagaaacca      120
gggaaagccc ctaagctcct gatctataag gcgtctagtt tagaaagtgg ggtcccatca      180
aggttcagcg gcagtggatc tgggacagaa ttcactctca ccatcagcag cctgcagcct      240
```

```
gatgattttg caacttatta ctgccaacag tataatagtt attggacgtt cggccaaggg      300
accaaggtgg aaatcaaa                                                    318
```

<210> SEQ ID NO 38
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
gaggtgcagc tggtggagtc tgggggaggc ttggtacagc ctggggggtc cctgagactc       60
tcctgtacag cctctggatt caccttcagt agttacgaca tgcactgggt ccgccaagct      120
acaggaaaag gtctggagtg ggtctcagtt attgatactg ctggtgacac atactatcca      180
ggctccgtga agggccgatt caccatctcc agagaaaatg ccaagaactc cttgtatctt      240
caaatgaaca gcctgagagc cggggacacg gctgtgtatt actgtgtaag agataggtat      300
agtgggaact tccactacaa cggtatggac gtctggggcc aagggaccac ggtcaccgtc      360
tcctca                                                                 366
```

<210> SEQ ID NO 39
<211> LENGTH: 293
<212> TYPE: PRT
<213> ORGANISM: Staphylococcus aureus

<400> SEQUENCE: 39

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220
```

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 40
<211> LENGTH: 293
<212> TYPE: PRT
<213> ORGANISM: Staphylococcus aureus

<400> SEQUENCE: 40

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn

290

<210> SEQ ID NO 41
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Met Gly Met Asp Val Trp
            100                 105                 110

Gly Gln Gly Thr Thr Val Thr Val Ser Ser
        115                 120
```

<210> SEQ ID NO 42
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105
```

<210> SEQ ID NO 43
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Arg Thr Gly His Tyr Met Gly Met Asp Val Trp
            100                 105                 110

Gly Gln Gly Thr Thr Val Thr Val Ser Ser
            115                 120

<210> SEQ ID NO 44
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105

<210> SEQ ID NO 45
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

```
Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Asp Arg Tyr Ser Arg Thr Gly His Tyr Met Gly Met Ser Leu Trp
            100                 105                 110

Gly Gln Gly Thr Thr Val Thr Val Ser Ser
        115                 120

<210> SEQ ID NO 46
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Thr Tyr Trp Thr
                 85                  90                  95

Phe Gly Gln Gly Thr Lys Val Glu Ile Lys
            100                 105

<210> SEQ ID NO 47
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Asp Asn Tyr Ser Arg Thr Gly His Tyr Met Gly Met Asp Val Trp
            100                 105                 110

Gly Gln Gly Thr Thr Val Thr Val Ser Ser
        115                 120
```

```
<210> SEQ ID NO 48
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys
            100                 105

<210> SEQ ID NO 49
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Asn Tyr Ser Arg Thr Gly His Tyr Met Gly Met Asp Val Trp
            100                 105                 110

Gly Gln Gly Thr Thr Val Thr Val Ser Ser
        115                 120

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105
```

<210> SEQ ID NO 51
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Met Gly Met Ser Leu Trp
            100                 105                 110

Gly Gln Gly Thr Thr Val Thr Val Ser Ser
        115                 120
```

<210> SEQ ID NO 52
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60
```

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Trp Thr
                85                  90                  95

Phe Gly Gln Gly Thr Lys Val Glu Ile Lys
            100                 105

<210> SEQ ID NO 53
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Arg Thr Gly His Tyr Met Gly Met Asp Val Trp
            100                 105                 110

Gly Gln Gly Thr Thr Val Thr Val Ser Ser
        115                 120

<210> SEQ ID NO 54
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys
            100                 105

<210> SEQ ID NO 55
<211> LENGTH: 122

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Asn Tyr Ser Ser Thr Gly Tyr Tyr Gly Met Asp Val Trp
            100                 105                 110

Gly Gln Gly Thr Thr Val Thr Val Ser Ser
        115                 120

<210> SEQ ID NO 56
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 57
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
```

```
                    20                  25                  30

Asp Met His Trp Val Arg Gln Ala Thr Gly Lys Gly Leu Glu Trp Val
            35                  40                  45

Ser Gly Ile Gly Thr Ala Gly Asp Thr Tyr Tyr Pro Asp Ser Val Lys
        50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
            115                 120

<210> SEQ ID NO 58
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys
            100                 105

<210> SEQ ID NO 59
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
```

```
                85                  90                  95

Arg Asp Asn Tyr Ser Pro Thr Gly Tyr Tyr Gly Met Asp Val Trp
            100                 105                 110

Gly Gln Gly Thr Thr Val Thr Val Ser Ser
        115                 120

<210> SEQ ID NO 60
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Trp Thr
                85                  90                  95

Phe Gly Gln Gly Thr Lys Val Glu Ile Lys
            100                 105

<210> SEQ ID NO 61
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Arg Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
        115                 120

<210> SEQ ID NO 62
<211> LENGTH: 122
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Arg Gly Asp Thr Tyr Tyr Pro Asp Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Lys Tyr Ser Pro Thr Gly His Tyr Tyr Gly Met Asp Val Trp
            100                 105                 110

Gly Gln Gly Thr Thr Val Thr Val Ser Ser
        115                 120

<210> SEQ ID NO 63
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Val Lys Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Trp Thr
                85                  90                  95

Phe Gly Gln Gly Thr Lys Val Glu Ile Lys
            100                 105

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Gln Tyr Asp Thr Tyr Trp Thr
1               5

<210> SEQ ID NO 65

-continued

```
<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Arg Tyr Ser Arg Thr Gly His Tyr Met Gly Met Asp Val
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Arg Tyr Ser Arg Thr Gly His Tyr Met Gly Met Ser Leu
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Asn Tyr Ser Arg Thr Gly His Tyr Met Gly Met Asp Val
1               5                   10

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Gln Tyr Ala Asp Tyr Trp Thr
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser His Asp Met His
1               5

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70
```

```
Gly Ile Gly Thr Ala Gly Asp Thr Tyr Tyr Pro Asp Ser Val Lys Gly
1               5                   10                  15
```

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

```
Asp Arg Tyr Ser Pro Thr Gly His Tyr Tyr Gly Met Asp Val
1               5                   10
```

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

```
Asp Asn Tyr Ser Pro Thr Gly Gly Tyr Tyr Gly Met Asp Val
1               5                   10
```

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

```
Lys Ala Ser Ser Leu Lys Ser
1               5
```

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

```
Gln Gln Tyr Glu Ser Tyr Trp Thr
1               5
```

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

```
Gly Ile Gly Thr Arg Gly Asp Thr Tyr Tyr Pro Asp Ser Val Lys Gly
1               5                   10                  15
```

<210> SEQ ID NO 76
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 76

Asp Lys Tyr Ser Pro Thr Gly His Tyr Tyr Gly Met Asp Val
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Ala Ser Ser Leu Val Lys
1               5

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Arg Tyr Ser Pro Thr Gly His Tyr Met Gly Met Ser Leu
1               5                   10

<210> SEQ ID NO 79
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser
        115                 120

<210> SEQ ID NO 80
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 80
atatatgagc tcgcagattc tgatattaat attaaaacc                                    39

<210> SEQ ID NO 81
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
atatataagc ttaatttgtc atttcttctt tttccc                                       36

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 82

His His His His His His
1               5

<210> SEQ ID NO 83
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gataaagaaa atggcatgct caaaaaagta ttttatagtt ttatc                             45

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gataaaacta taaatactt ttttgagcat gccattttct ttatc                              45

<210> SEQ ID NO 85
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
atattggatc cgcagattct gatattaata ttaaaac                                      37

<210> SEQ ID NO 86
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 86
atacttctcg agttatttat tatgattttt atcatcgata aaac                         44

<210> SEQ ID NO 87
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
catagggatc caaactgcta gttattagaa cgaaag                                  36

<210> SEQ ID NO 88
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
catagctcga gtcaatttgt catttcttct ttttcccaat c                            41

<210> SEQ ID NO 89
<211> LENGTH: 293
<212> TYPE: PRT
<213> ORGANISM: Staphylococcus aureus

<400> SEQUENCE: 89
```

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe

```
            210                 215                 220
Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Ile Asp Arg Ser Ser Glu Arg Tyr Lys Ile Asp Trp Glu Lys
            275                 280                 285

Glu Glu Met Thr Asn
        290

<210> SEQ ID NO 90
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ala Gln His Ile Thr Pro Val Ser Glu Lys Lys Val Asp Asp Lys Ile
1               5                   10                  15

Thr Leu Tyr Lys Thr Thr Ala Thr Ser Asp Ser Asp Lys Leu Lys Ile
            20                  25                  30

Ser Gln Ile Leu Thr Phe Asn Phe Ile Lys Asp Lys Ser Tyr Asp Lys
        35                  40                  45

Asp Thr Leu Ile Leu Lys Ala Ala Gly Asn Ile Tyr Ser Gly Tyr Thr
    50                  55                  60

Lys Pro Asn Pro Lys Asp Thr Ile Ser Ser Gln Phe Tyr Trp Gly Ser
65              70                  75                  80

Lys Tyr Asn Ile Ser Ile Asn Ser Asp Ser Asn Asp Ser Val Asn Val
            85                  90                  95

Val Asp Tyr Ala Pro Lys Asn Gln Asn Glu Glu Phe Gln Val Gln Gln
        100                 105                 110

Thr Val Gly Tyr Ser Tyr Gly Gly Asp Ile Asn Ile Ser Asn Gly Leu
    115                 120                 125

Ser Gly Gly Gly Asn Gly Ser Lys Ser Phe Ser Glu Thr Ile Asn Tyr
130                 135                 140

Lys Gln Glu Ser Tyr Arg Thr Ser Leu Asp Lys Arg Thr Asn Phe Lys
145                 150                 155                 160

Lys Ile Gly Trp Asp Val Glu Ala His Lys Ile Met Asn Asn Gly Trp
            165                 170                 175

Gly Pro Tyr Gly Arg Asp Ser Tyr His Ser Thr Tyr Gly Asn Glu Met
        180                 185                 190

Phe Leu Gly Ser Arg Gln Ser Asn Leu Asn Ala Gly Gln Asn Phe Leu
    195                 200                 205

Glu Tyr His Lys Met Pro Val Leu Ser Arg Gly Asn Phe Asn Pro Glu
210                 215                 220

Phe Ile Gly Val Leu Ser Arg Lys Gln Asn Ala Ala Lys Lys Ser Lys
225                 230                 235                 240

Ile Thr Val Thr Tyr Gln Arg Glu Met Asp Arg Tyr Thr Asn Phe Trp
            245                 250                 255

Asn Gln Leu His Trp Ile Gly Asn Asn Tyr Lys Asp Glu Asn Arg Ala
        260                 265                 270
```

```
Thr His Thr Ser Ile Tyr Glu Val Asp Trp Glu Asn His Thr Val Lys
            275                 280                 285

Leu Ile Asp Thr Gln Ser Lys Glu Lys Asn Pro
    290                 295

<210> SEQ ID NO 91
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Arg Tyr Ser Pro Thr Gly His Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Tyr Ile Thr Arg Glu Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320
```

```
Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 92
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Lys Gln Tyr Ala Asp Tyr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

```
Cys Glu Val Thr His Gln Gly Leu Ser Ser Pro Val Thr Lys Ser Phe
    195                 200                 205

Asn Arg Gly Glu
    210
```

ANTIBODIES THAT SPECIFICALLY BIND *STAPHYLOCOCCUS AUREUS* ALPHA TOXIN AND METHODS OF USE

CROSS-REFERENCE TO RELATED APPLICATIONS

This application is a U.S. National Stage application of International Application No. PCT/US2012/024201, filed on Feb. 7, 2012, said International Application No. PCT/US2012/024201 claims benefit under 35 U.S.C. §119(e) of the U.S. Provisional Application No. 61/440,581, filed Feb. 8, 2011. Each of the above listed applications is incorporated by reference herein in its entirety for all purposes.

REFERENCE TO THE SEQUENCE LISTING

This application incorporates by reference a Sequence Listing submitted with this application as text file entitled ATOX100US_Sequence Listing_2016 Sep. 9, created on Sep. 9, 2016, and having a size of 72.8 kilobytes.

FIELD

The technology relates in part to antibodies, and in certain embodiments, antibodies that specifically bind to *Staphylococcus aureus* alpha toxin.

BACKGROUND

*Staphylococcus aureus* is a gram-positive, facultatively aerobic, clump-forming cocci bacteria that commonly colonizes the nose and skin of healthy humans. Approximately 20-30% of the population is colonized with *S. aureus* at any given time. *Staphylococcus aureus* bacteria, sometimes also referred to as "staph", "Staph. aureus", or "S. aureus", are considered opportunistic pathogens that cause minor infections (e.g., pimples, boils) and systemic infections.

Mucosal and epidermal barriers (skin) normally protect against *S. aureus* infections. Interruption of these natural barriers as a result of injuries (e.g., burns, trauma, surgical procedures and the like) dramatically increases the risk of infection. Diseases that compromise the immune system (e.g., diabetes, end-stage renal disease, cancer and the like) also increase the risk of infection. Opportunistic *S. aureus* infections can become serious, causing a variety of diseases or conditions, non-limiting examples of which include bacteremia, cellulitis, eyelid infections, food poisoning, joint infections, skin infections, scalded skin syndrome, toxic shock syndrome, pneumonia, osteomyelitis, endocarditis, meningitis and abscess formation.

*S. aureus* also can cause infection and disease in animals. For example, *S. aureus* frequently is associated with bovine mastitis.

*S. aureus* expresses a number of virulence factors, including capsular polysaccharides and protein toxins. One virulence factor often associated with *S. aureus* infection that is the major cytotoxic agent is alpha-toxin (also known as alpha-hemolysin or Hla), a pore-forming and hemolytic exoprotein produced by most pathogenic strains of *S. aureus*. The toxin forms heptameric pores in membranes of susceptible cells such as white blood cells, platelets, erythrocytes, peripheral blood monocytes, macrophages, keratinocytes, fibroblasts and endothelial cells. Alpha toxin pore formation often leads to cell dysfunction or lysis.

BRIEF SUMMARY OF THE DISCLOSURE

In certain embodiments, provided is a purified or isolated antibody, or antigen-binding fragment thereof, which antibody or fragment immunospecifically binds to a *Staphylococcus aureus* alpha toxin polypeptide. The terms "alpha toxin polypeptide," "alpha toxin monomer" and "alpha toxin oligomers (e.g., heptamer)" are referred to herein as "AT," "AT monomer" and "AT oligomer," respectively. The term "variable heavy chain" is referred to as "VH". The term "variable light chain" is referred to as "VL".

In some embodiments, the isolated antibody or antigen-binding fragment thereof that immunospecifically binds to a *Staphylococcus aureus* alpha toxin polypeptide includes, (a) a VH CDR1 comprising an amino acid sequence identical to, or comprising 1, 2, or 3 amino acid residue substitutions relative to SEQ ID NO: 7, 10, 13 or 69; (b) a VH CDR2 comprising an amino acid sequence identical to, or comprising 1, 2, or 3 amino acid residue substitutions relative to SEQ ID NO: 8, 11, 14, 17, 70 or 75; and (c) a VH CDR3 comprising an amino acid sequence identical to, or comprising 1, 2, or 3 amino acid residue substitutions relative to SEQ ID NO: 9, 12, 15, 18, 16, 65, 66, 67, 71, 72, 76 or 78.

In particular embodiments, the isolated antibody or antigen-binding fragment thereof comprises a VH CDR1, VH CDR2 and VH CDR3 comprising amino acid sequences identical to, or comprising 1, 2, or 3 amino acid residue substitutions in each CDR relative to SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs 7, 8, and 67; SEQ ID NOs: 7, 8 and 78; SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

In some embodiments, the isolated antibody or antigen-binding fragment thereof that immunospecifically binds to a *Staphylococcus aureus* alpha toxin polypeptide includes, (a) a VL CDR1 comprising an amino acid sequence identical to, or comprising 1, 2, or 3 amino acid residue substitutions relative to SEQ ID NO: 1 or 4; (b) a VL CDR2 comprising an amino acid sequence identical to, or comprising 1, 2, or 3 amino acid residue substitutions relative to SEQ ID NO: 2, 5, 73 or 77; and (c) a VL CDR3 comprising an amino acid sequence identical to, or comprising 1, 2, or 3 amino acid residue substitutions relative to SEQ ID NO: 3, 6, 64, 68 or 74.

In particular embodiments, the isolated antibody or antigen-binding fragment thereof comprises a VL CDR1, VL CDR2 and VL CDR3 comprising amino acid sequences identical to, or comprising 1, 2, or 3 amino acid residue substitutions in each CDR relative to SEQ ID NOs: 1, 2 and 3; SEQ ID NOs: 4, 5 and 6; SEQ ID NOs: 1, 2 and 64; SEQ ID NOs: 1, 2 and 68; SEQ ID NOs: 1, 73 and 74; or SEQ ID NOs: 1, 77 and 74.

In some embodiments, the isolated antibody or antigen-binding fragment thereof that immunospecifically binds to a *Staphylococcus aureus* alpha toxin polypeptide comprises a VH CDR1, VH CDR2, VH CDR3, VL CDR1, VL CDR2 and VL CDR3 comprising amino acid sequences identical to, or comprising 1, 2, or 3 amino acid residue substitutions in each CDR relative to: (a) a VH CDR1 comprising the amino acid sequence of SEQ ID NO: 7, 10, 13 or 69; (b) a VH CDR2 comprising the amino acid sequence of SEQ ID NO: 8, 11, 14, 17, 70 or 75; (c) a VH CDR3 comprising the amino acid sequence of SEQ ID NO: 9, 12, 15, 18, 16, 65, 66, 67, 71, 72, 76 or 78; (d) a VL CDR1 comprising the amino acid sequence of SEQ ID NO: 1 or 4; (e) a VL CDR2 comprising the amino acid sequence of SEQ ID NO: 2, 5, 73, or 77; and (f) a VL CDR3 comprising the amino acid sequence of SEQ ID NO: 3, 6, 64, 68 or 74.

In particular embodiments, the isolated antibody or antigen-binding fragment thereof comprises a VH CDR1, VH CDR2, VH CDR3, VL CDR1, VL CDR2, and VL CDR3 comprising amino acid sequences identical to, or comprising 1, 2, or 3 amino acid residue substitutions in each CDR relative to SEQ ID NOs: 7, 8, 9, 1, 2 and 3; SEQ ID NOs: 10, 11, 12, 1, 2 and 3; SEQ ID NOs: 13, 14, 15, 4, 5 and 6; SEQ ID NOs: 7, 17, 18, 1, 2 and 3; SEQ ID NOs: 7, 8, 16, 1, 2 and 64; SEQ ID NOs: 7, 8, 65, 1, 2 and 64; SEQ ID NOs; 7, 8, 66, 1, 2 and 64; SEQ ID NOs: 7, 8, 67, 1, 2 and 68; SEQ ID NOs: 7, 8, 67, 1, 2 and 64; SEQ ID NOs: 7, 8, 78, 1, 2 and 64; SEQ ID NOs: 7, 8, 65, 1, 2 and 68; SEQ ID NOs: 69, 70, 71, 1, 2 and 68; SEQ ID NOs: 7, 8, 72, 1, 73 and 74; SEQ ID NOs: 69, 75, 71, 1, 2 and 68; SEQ ID NOs: 69, 75, 76, 1, 2 and 68; SEQ ID NOs: 69, 75, 76, 1, 77 and 74; SEQ ID NOs: 69, 70, 71, 1, 77 and 74, In some embodiments, provided is a composition that comprises an isolated antibody or antigen-binding fragment thereof that (i) includes a VH chain domain comprising three CDRs and a VL chain domain comprising three CDRs; and (ii) immunospecifically binds to a *Staphylococcus aureus* alpha toxin polypeptide, where the three CDRs of the VH chain domain include (a) a VH CDR1 comprising the amino acid sequence of SEQ ID NO: 7, 10, 13 or 69; (b) a VH CDR2 comprising the amino acid sequence of SEQ ID NO: 8, 11, 14, 17, 70 or 75; and (c) a VH CDR3 comprising the amino acid sequence of SEQ ID NO: 9, 12, 15, 18, 16, 65, 66, 67, 71, 72, 76 or 78. In particular embodiments, the VH CDR1, VH CDR2 and VH CDR3 correspond to SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs 7, 8, and 67; SEQ ID NOs: 7, 8 and 78; SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

Also provided in certain embodiments is a composition that comprises an isolated antibody or antigen-binding fragment thereof that (i) includes a VH chain domain comprising three CDRs and a VL chain domain comprising three CDRs; and (ii) immunospecifically binds to a *Staphylococcus aureus* alpha toxin polypeptide, where the three CDRs of the VL chain domain include (a) a VL CDR1 comprising the amino acid sequence of SEQ ID NO: 1 or 4; (b) a VL CDR2 comprising the amino acid sequence of SEQ ID NO: 2, 5, 73, or 77; and (c) a VL CDR3 comprising the amino acid sequence of SEQ ID NO: 3, 6, 64, 68 or 74. In particular embodiments, the VL CDR1, VL CDR2 and VL CDR3 correspond to SEQ ID NOs: 1, 2 and 3; SEQ ID NOs: 4, 5 and 6; SEQ ID NOs: 1, 2 and 64; SEQ ID NOs: 1, 2 and 68; SEQ ID NOs: 1, 73 and 74; or SEQ ID NOs: 1, 77 and 74.

Provided also in some embodiments are compositions that include an isolated antibody or antigen-binding fragment thereof that (i) immunospecifically binds to a *Staphylococcus aureus* alpha toxin polypeptide, (ii) comprises a heavy chain variable domain comprising at least 90% identity to the amino acid sequence of SEQ ID NO: 20, 22, 24, 26, 28, 41, 43, 45, 47, 49, 51, 53, 55, 57, 79, 59, 61, or 62 and (iii) comprises a light chain variable domain comprising at least 90% identity to the amino acid sequence of SEQ ID NO: 19, 21, 23, 25, 27, 42, 44, 46, 48, 50, 52, 54, 56, 58, 60 or 63.

In some embodiments, the isolated antibody or antigen-binding fragment thereof includes a heavy chain variable domain of SEQ ID NO: 20, 22, 24, 26, 28, 41, 43, 45, 47, 49, 51, 53, 55, 57, 79, 59, 61, or 62 and a light chain variable domain of SEQ ID NO: 19, 21, 23, 25, 27, 42, 44, 46, 48, 50, 52, 54, 56, 58, 60 or 63.

In particular embodiments, the isolated antibody or antigen-binding fragment thereof comprises a VH and a VL, where the VH and VL are each identical to or each have at least 90%, 95% or 98% identity to the VH and VL amino acid sequences of SEQ ID NOs: 20 and 19; SEQ ID NOs; 22 and 21; SEQ ID NOs: 24 and 23; SEQ ID NOs: 26 and 25; SEQ ID NOs: 28 and 27; SEQ ID NOs: 41 and 42; SEQ ID NOs: 43 and 44; SEQ ID NOs: 45 and 46; SEQ ID NOs: 47 and 48; SEQ ID NOs: 47 and 48; SEQ ID NOs: 49 and 50; SEQ ID NOs: 51 and 52; SEQ ID NOs: 51 and 52; SEQ ID NOs: 53 and 54; SEQ ID NOs: 55 and 56; SEQ ID NOs: 57 and 58; SEQ ID NOs: 59 and 60; SEQ ID NOs: 61 and 58; SEQ ID NOs: 62 and 58; SEQ ID NOs: 62 and 63; SEQ ID NOs: 79 and 63.

In some embodiments, an isolated antibody or antigen-binding fragment thereof immunospecifically binds to a *Staphylococcus aureus* alpha toxin polypeptide and has one or more of the characteristics selected from the group consisting of: (a) an affinity constant ($K_D$) of about 13 nM or less for the *Staphylococcus aureus* alpha toxin polypeptide; (b) inhibits oligomerization of the *Staphylococcus aureus* alpha toxin polypeptide by at least 50%, 60%, 70%, 80%, 90%, or 95%; and (c) reduces A549 (lung epithelial) lysis or THP-1 (monocyte) and erythrocyte lysis by at least 50%, 60%, 70%, 80%, 90%, or 95%, where the isolated antibody or antigen-binding fragment and the *S. aureus* toxin are present in a molar ratio of about 1:1.

In some embodiments, the erythrocyte is a cell from the blood. In certain embodiments, the cell from the blood is a red blood cell. In some embodiments, lysis is determined by an in vitro hemolytic assay. In other embodiments, lysis is determined by an in vitro lactate dehydrogenase release assay. These assays are described further below, or can be performed routinely by one of ordinary skill in the art.

In some embodiments, the isolated antibody or antigen-binding fragment thereof includes a diagnostic agent. In certain embodiments, the diagnostic agent includes an imaging agent. The diagnostic agent, in some embodiments, includes a detectable label. In certain embodiments, the isolated antibody or antigen-binding fragment thereof is linked to the diagnostic agent via a linker.

In some embodiments, a *Staphylococcus aureus* alpha toxin polypeptide is a native toxin polypeptide. A *Staphylococcus aureus* alpha toxin polypeptide in some embodiments includes one or more amino acid deletions, additions and/or substitutions (e.g., 1, 2, 3, 4, 5, 6, 7, 8, 9, 10 amino acid insertions, deletions and/or substitutions) relative to the native toxin polypeptide. In some embodiments, a *Staphylococcus aureus* alpha toxin polypeptide is a recombinant protein. In certain embodiments, the *Staphylococcus aureus* alpha toxin polypeptide includes an amino acid sequence of SEQ ID NO: 39, or fragments thereof. In certain other embodiments, the *Staphylococcus aureus* alpha toxin polypeptide is an attenuated form of the polypeptide, such as H35L, where the histidine at position 35 of the wild-type polypeptide is replaced with leucine, for example, as represented by SEQ ID NO: 40.

In certain embodiments, the isolated antibody or antigen-binding fragment thereof immunospecifically binds to a *Staphylococcus aureus* alpha toxin polypeptide and includes a VH CDR3 comprising an amino acid sequence identical to, or comprising 1, 2, or 3 amino acid residue substitutions relative to SEQ ID NO: 9, 12, 15, 18, 16, 65, 66, 67, 71, 72, 76 or 78, where the antibody or antigen-binding fragment thereof neutralizes the *Staphylococcus aureus* alpha toxin polypeptide. In some embodiments, the isolated antibody or antigen-binding fragment of an isolated antibody immunospecifically binds to a *Staphylococcus aureus* alpha toxin polypeptide and includes a VL CDR3 comprising an amino acid sequence identical to, or including 1, 2, or 3 amino acid residue substitutions relative to, SEQ ID NO: 3, 6, 64, 68 or 74, where the antibody or antigen-binding fragment thereof neutralizes the *Staphylococcus aureus* alpha toxin polypeptide.

In certain embodiments, the isolated antibody or antigen-binding fragment thereof immunospecifically binds to a *Staphylococcus aureus* alpha toxin polypeptide and includes a VH CDR3 comprising an amino acid sequence identical to, or including 1, 2, or 3 amino acid residue substitutions relative to, SEQ ID NO: 9, 12, 15, 18, 16, 65, 66, 67, 71, 72, 76 or 78, where the antibody or antigen-binding fragment thereof inhibits oligomerization of the *Staphylococcus aureus* alpha toxin polypeptide. In some embodiments, the isolated antibody or antigen-binding fragment thereof immunospecifically binds to a *Staphylococcus aureus* alpha toxin polypeptide and includes a VL CDR3 comprising an amino acid sequence identical to, or including 1, 2, or 3 amino acid residue substitutions relative to, SEQ ID NO: 3, 6, 64, 68 or 74, where the antibody or antigen-binding fragment thereof inhibits oligomerization of the *Staphylococcus aureus* alpha toxin polypeptide. In certain embodiments, the inhibition of oligomerization is determined by an in vitro binding and electrophoretic mobility assay.

Also provided herein are kits, including (a) a composition comprising an isolated antibody or antigen-binding fragment thereof, and (b) instructions for using the composition or directions for obtaining instructions for using the composition. In some embodiments, the antibody in the composition is linked to a solid support. In certain embodiments, the solid support is a bead, and in some embodiments, the bead is a sepharose bead. In some embodiments, the instructions for use include one or more of isolating, purifying, detecting and quantifying a *Staphylococcus aureus* alpha toxin polypeptide.

In certain embodiments, the kit includes a buffer and membrane suitable for a Western blot. In some embodiments, the kit includes a loading buffer and an elution buffer. In certain embodiments, the kit includes a buffer suitable for an enzyme-linked immunosorbant assay (ELISA).

Provided also herein is a method for preventing, treating or managing pneumonia in a subject, including: administering a composition that includes an antibody or antigen-binding fragment thereof that immunospecifically binds to a *Staphylococcus aureus* alpha toxin polypeptide to a subject in need thereof in an amount effective for preventing, treating or managing the pneumonia.

In some embodiments, the method prevents pneumonia. In certain embodiments, the antibody or antigen-binding fragment thereof immunospecifically binds to a linear or conformational epitope that comprises one or more residues or a portion or fragment of amino acids 1 to 293, or of amino acids 51 to 293 of a Staphylococcal alpha toxin polypeptide. In certain embodiments, the antibody or antigen-binding fragment thereof binds to a fragment where the antibody or antigen-binding fragment has contact residues at T261, T163, N264, K266 and K271 of SEQ ID NO: 39. In further embodiments, the antibody or antigen-binding fragment thereof binds a fragment of alpha toxin where the antibody or antigen-binding fragment has additional contact residues at N177, W179, G180, P181, Y182, D183, D185, S186, W187, N188, P189, V190, Y191 and R200 of SEQ ID NO: 39.

In certain embodiments, the antibody or antigen-binding fragment has contact residues at N177, W179, G180, P181, Y182, D183, D185, S186, W187, N188, P189, V190, Y191, R200, T261, T163, N264, K266 and K271 of SEQ ID NO: 39. In other embodiments, the antibody or antigen-binding fragment thereof binds to a fragment comprising amino acids 261-272 of SEQ ID NO: 39. In further embodiments, the antibody or antigen-binding fragment thereof binds to a fragment comprising amino acids 248-277 of SEQ ID NO: 39. In other embodiments, the antibody or antigen-binding fragment thereof binds to a fragment comprising amino acids 173-201 of SEQ ID NO: 39 and a fragment comprising amino acids 261-272 of SEQ ID NO: 39 or to a fragment comprising amino acids 173-201 of SEQ ID NO: 39 and a fragment comprising amino acids 248-277 of SEQ ID NO: 39

In certain embodiments, the antibody or antigen-binding fragment thereof binds to a fragment where the antibody or antigen-binding fragment has contact residues at T261, T163, N264, K266 and K271 of SEQ ID NO: 40. In further embodiments, the antibody or antigen-binding fragment thereof binds a fragment of alpha toxin where the antibody or antigen-binding fragment has additional contact residues at N177, W179, G180, P181, Y182, D183, D185, S186, W187, N188, P189, V190, Y191 and R200 of SEQ ID NO: 40.

In certain embodiments, the antibody or antigen-binding fragment has contact residues at N177, W179, G180, P181, Y182, D183, D185, S186, W187, N188, P189, V190, Y191, R200, T261, T163, N264, K266 and K271 of SEQ ID NO: 40. In other embodiments, the antibody or antigen-binding fragment thereof binds to a fragment comprising amino acids 261-272 of SEQ ID NO: 40. In further embodiments, the antibody or antigen-binding fragment thereof binds to a fragment comprising amino acids 248-277 of SEQ ID NO: 40. In other embodiments, the antibody or antigen-binding fragment thereof binds to a fragment comprising amino acids 173-201 of SEQ ID NO: 40 and a fragment comprising amino acids 261-272 of SEQ ID NO: 40, In other embodiments, the antibody or antigen-binding fragment thereof binds to a fragment comprising (1) amino acids 261-272, (2) amino acids 248-277 or (3) amino acids 173-201 and 261-272, of a Staphylococcal alpha toxin polypeptide or Staphylococcal alpha toxin polypeptide variant, where amino acids 261-272, amino acids 248-277 or amino acids 173-201 correspond to the same amino acid sequence as that of the corresponding region in SEQ ID NO: 39, or contain substitutions within the fragment having the corresponding region in SEQ ID NO: 39, where the substitutions do not alter the ability of the antibody or antigen-binding fragment thereof to bind to the alpha toxin polypeptide.

Provided in some embodiments is a method for preventing, treating or managing a skin infection condition in a subject that includes: administering a composition that includes an antibody or antigen-binding fragment thereof that immunospecifically binds to a *Staphylococcus aureus* alpha toxin polypeptide according to the present invention to a subject in need thereof in an amount effective for preventing, treating or managing the skin infection condition. In certain embodiments, the skin infection condition is dermonecrosis. In some embodiments, the skin infection condition includes a *Staphylococcus aureus* infection of the skin. In certain embodiments, the method prevents the skin infection condition.

In some embodiments, provided is a method for preventing, treating or managing a condition associated with *Staphylococcus aureus* infection that includes: administering a composition that includes an antibody or antigen-binding fragment thereof that immunospecifically binds to a *Staphylococcus aureus* alpha toxin polypeptide according to the present invention to a subject in need thereof, in an amount effective to reduce oligomerization of the toxin polypeptide. In certain embodiments, the method prevents the condition associated with *Staphylococcus aureus* infection.

In some embodiments, provided is a method for preventing, treating or managing a *S. aureus* infection associated with dialysis treatment, high-risk surgery, pneumonia, ventilator-associated pneumonia (VAP), or reinfection after prior release from a hospital for previous treatment or surgery that includes administering a composition that includes an antibody or antigen-binding fragment thereof that immunospecifically binds to a *Staphylococcus aureus* alpha toxin polypeptide to a subject in need thereof.

Also provided in some embodiments is a method for preventing, treating or managing a condition associated with *Staphylococcus aureus* infection that includes administering a composition that includes an antibody or antigen-binding fragment thereof that immunospecifically binds to a *Staphylococcus aureus* alpha toxin polypeptide to a subject in need thereof, in an amount effective to reduce cell lysis. In certain embodiments, the method prevents a condition associated with *Staphylococcus aureus* infection. In some embodiments, the cell is an erythrocyte from the blood or the lung.

In some embodiments, the antibody or antigen-binding fragment thereof immunospecifically binds to a linear or conformational epitope that comprises one or more residues. In certain embodiments, the composition administered to the subject is according to any one of the compositions described herein.

Provided also in certain embodiments is a method that includes: administering a composition described herein to cells; and detecting the presence, absence or amount of a biological effect associated with the administration of the composition to the cells. Also provided in some embodiments is a method that includes: administering a composition described herein to a subject; and detecting the presence, absence or amount of a biological effect in the subject associated with the administration of the composition. Also provided in certain embodiments is a method that includes: administering a composition described herein to a subject; and monitoring the condition of the subject.

Also provided in some embodiments is a method for neutralizing a *Staphylococcus aureus* alpha toxin polypeptide by administering to a subject in need thereof an effective amount of any one of the compositions described herein to neutralize the toxin polypeptide.

Provided also in certain embodiments is a method of preventing, treating, or managing a condition mediated by a *Staphylococcus aureus* infection in a subject in need thereof, the method including administering to the subject an effective amount of any one of the compositions described herein to prevent, treat or manage the condition. Also provided in some embodiments is a method for treating, preventing or alleviating the symptoms of a disorder mediated by *Staphylococcus aureus* alpha toxin in a subject in need thereof, including administering an effective amount of any one of the compositions described herein to the subject to treat, prevent or alleviate the symptoms.

Provided also in certain embodiments is a method for diagnosing a condition mediated by a *Staphylococcus aureus* alpha toxin in a subject that includes selecting a subject in need of diagnosis and administering to the subject a diagnostically effective dose of any one of the compositions described herein. In some embodiments, the subject is a domestic animal, and in certain embodiments, the subject is a human.

Certain embodiments are described further in the following description, examples, claims and drawings.

BRIEF DESCRIPTION OF THE DRAWINGS

The drawings illustrate embodiments herein and are not limiting. For clarity and ease of illustration, the drawings are not made to scale and, in some instances, various aspects may be shown exaggerated or enlarged to facilitate an understanding of particular embodiments.

FIGS. 3A and 3B illustrate the results of passive immunization with inhibitory anti-*S. aureus* alpha toxin mAbs in a dermonecrosis model. Groups of 5 BALB/c mice were passively immunized with 5 mg/kg of the inhibitory mAbs and then infected with *S. aureus* Wood and lesion size monitored for 6 days. FIG. 3A shows photographs of the lesion size 6 days post infection. FIG. 3B graphically illustrates the reduction in lesion size over the time course of infection. Experimental details and results are described in Example 4.

FIG. 4 illustrates the results of C57BL/6J mice passively immunized with 5, 15 and 45 mg/kg purified 12B8.19, 24-hours prior to infection with *S. aureus* USA300 ($3\times10^8$ cfu).

FIG. 5 illustrates the results of C57BL/6J mice passively immunized with 5, 15 and 45 mg/kg purified 2A3.1, 24-hours prior to infection with *S. aureus* USA300 ($3\times10^8$ cfu).

FIG. 6 illustrates the results of C57BL/6J mice passively immunized with 5, 15 and 45 mg/kg purified 28F6.1, 24-hours prior to infection with *S. aureus* USA300 ($3\times10^8$ cfu).

FIG. 7 illustrates the results of C57BL/6J mice passively immunized with 5, 15 and 45 mg/kg purified 10A7.5, 24-hours prior to infection with *S. aureus* USA300 ($3\times10^8$ cfu). Experimental details and results are described in Example 5.

FIG. 20 shows sequence alignments of alpha toxin and LukF-PV proteins. Alpha toxin shares 25% amino acid sequence identity with LukF-PV (UniProtKB/TrEMBL accession number B1Q018). Amino acid numbering is based on mature proteins. The alignment was performed using the method of Clustal W. The segment aa 248-277 is highlighted by underlining.

FIG. 22 is a ribbon diagram of the LC10 YTE Fab-α-toxin complex. The alpha-toxin molecule is indicated by the ribbon in the top portion of the diagram. The heavy chain is indicated by dark colored ribbon in the bottom portion of the diagram, and the light chain is indicated by the light colored ribbon in the bottom portion of the diagram.

FIG. 26 graphically represents the treatment efficacy of LC10 in a murine pneumonia model. Groups of 10 C57BL/6 mice were infected intradermally with $2 \times 10^8$ *S. aureus* USA300. One hour post-infection, animals were given a single intraperitoneal injection of LC-10 at (A) 15 mg/kg (B) 45 mg/kg. A cohort group of animals received subcutaneous vancomycin (VAN) 1 h post-infection. Additional treatments of VAN were given BID q 12 for a total of 6 treatments. A control group of 10 mice was treated with 15 mg/kg R347 1 h post-infection. Survival was monitored for 7 days.

DETAILED DESCRIPTION

Figure 1A:
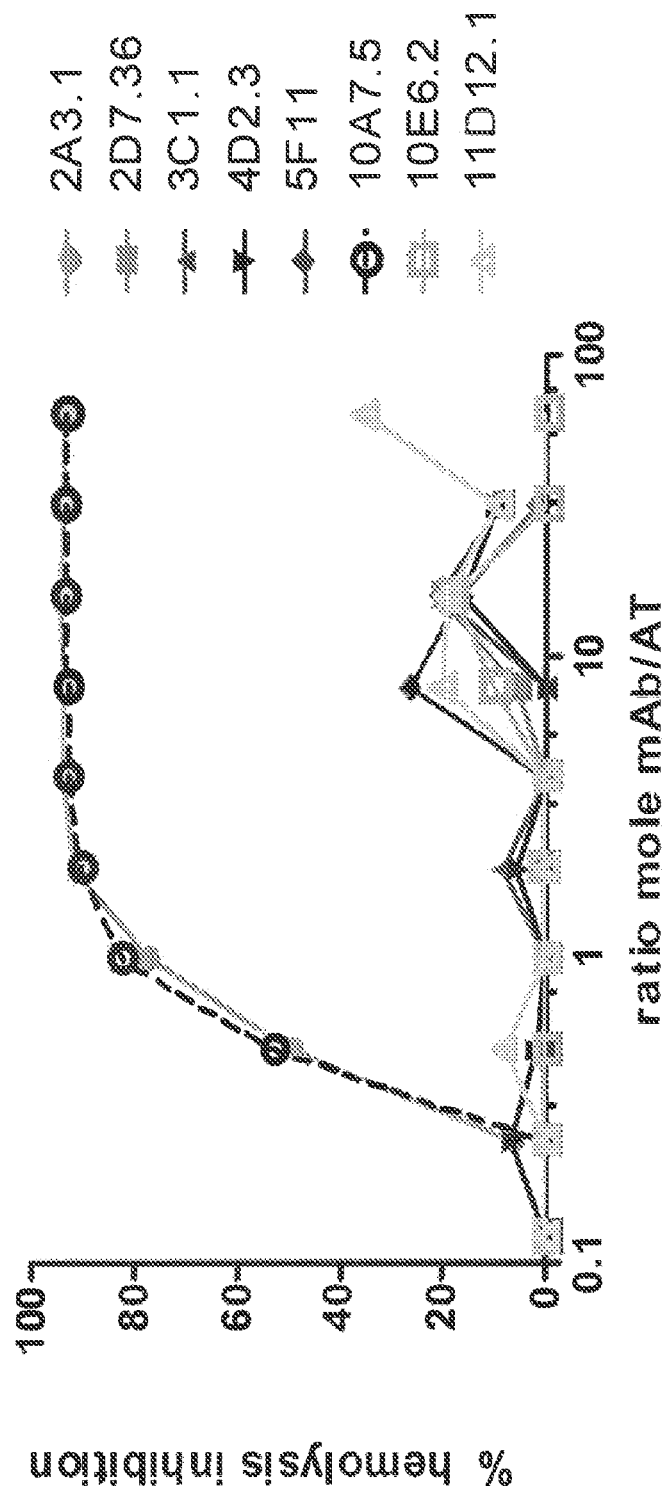
FIGS. 1A and 1B graphically illustrate the percent inhibition of red blood cell lysis by anti-alpha toxin antibodies. Experimental details and results are described in Example 3.

Herein provided are antibodies, including human, humanized and/or chimeric forms, as well as fragments, derivatives/conjugates and compositions thereof that bind to *Staphylococcus aureus* alpha toxin. Such antibodies can be useful for detecting and/or visualizing alpha toxin and therefore may be useful in assays and diagnostic methods. Antibodies described herein also interfere with alpha toxin heptamer formation, thereby inhibiting formation of the active pore forming complex, and therefore can be useful for, therapeutic and prophylactic methods.

*Staphylococcus aureus* is a ubiquitous pathogen, and sometimes is an etiological agent of a variety of conditions, ranging in severity from mild to fatal. *S. aureus* produces a large number of extracellular and cell-associated proteins, many of which are involved in pathogenesis, such as alpha-toxin, beta-toxin, gamma-toxin, delta-toxin, leukocidin, toxic shock syndrome toxin (TSST), enterotoxins, coagulase, protein A, fibrinogen, fibronectin binding protein and the like. Alpha-toxin (e.g., encoded by the hla gene) is one of the virulence factors of *Staphylococcus aureus* and is produced by the majority of pathogenic *S. aureus* strains.

*S. aureus* infections are relatively difficult to treat, and invasive diseases and relapse may occur following antibiotic treatment. Additionally, methicillin resistant *S. aureus* strains have become more prevalent, in hospital settings (e.g., HA-MRSA or healthcare associated) and non-hospital settings (e.g., CA-MRSA or community associated), further complicating treatment of *S. aureus* infections. In many instances, methicillin resistant strains of *S. aureus* are also resistant to one or more other antibiotics including aminoglycosides, tetracycline, chloramphenicol, macrolides and lincosamides.

Alpha toxin is a pore forming toxin and has cytolytic, hemolytic, dermonecrotic and lethal activities in humans as well as in animals. Staphylococcal alpha toxin is secreted as a water-soluble single chain polypeptide of 293 amino acids that is approximately 34 kilodaltons (kDa). Without being limited by theory, it is believed there are two methods of alpha toxin/target cell interaction; (i) alpha toxin binds to specific, high affinity receptors (ADAM 10) on the cell surface of human platelets, monocytes, endothelial cells, white blood cells, alveolar lung cells, macrophages, keratinocytes, fibroblasts, rabbit erythrocytes, and other cells (see e.g., Wilke et al., *Proc. Natl. Acad. Sci.* 107:13473-13478 (2010)), or (ii) alpha toxin interacts non-specifically by adsorption to lipid bilayers. In either mode of toxin/cell interaction, seven alpha toxin monomer molecules oligomerize to form a heptameric trans-membrane channel of 1-2 nm in diameter. Subsequent efflux of potassium and nucleotides and influx of sodium and calcium leads to osmotic lysis and/or multiple secondary actions, including eicosanoid production, secretory processes, contractile dysfunction, apoptosis and release of cytokines. The disruption of cellular activities and lysis of cells by alpha toxin is believed to contribute to the conditions and diseases associated with *S. aureus* infection.

Non-limiting examples of some common conditions caused by *S. aureus* infection include burns, cellulitis, dermonecrosis, eyelid infections, food poisoning, joint infections, pneumonia, skin infections, surgical wound infection, scalded skin syndrome and toxic shock syndrome. In addition, it is a frequent pathogen in foreign body infections, such as intravascular lines, pacemakers, artificial heart valves and joint implants. Some of the conditions or diseases caused by *S. aureus* are described further below. Some or all of the conditions and diseases described below may involve the direct action of alpha toxin as a component of infection or mediator of the condition or disease state, or some or all of the conditions may involve the indirect or secondary action of alpha toxin (e.g., a primary virulence factor causes the main symptom or majority of symptoms associated with the condition, and alpha toxin acts to further advance the disease through its disruption of cellular function and cell lysis activities).

Burns

Burn wounds often are sterile initially. However, moderate and severe burns generally compromise physical and immune barriers to infection (e.g., blistering, cracking or peeling of the skin), causing a loss of fluid and electrolytes and result in local or general physiological dysfunction. Contact of the compromised skin with viable bacteria sometimes can result in mixed colonization at the injury site. Infection may be restricted to the non-viable debris on the burn surface ("eschar"), or the colonization may progress into full skin infection and invade viable tissue below the eschar. More severe infections may reach below the skin, enter into the lymphatic system and/or blood circulation, and develop into septicemia. *S. aureus* typically is found among the pathogens that colonize burn wound infections. *S. aureus* can destroy granulation tissue and produce severe septicemia.

Skin and Soft Tissue Infections

Cellulitis

Cellulitis is an acute infection of the skin that often begins as a superficial infection that can spread below the cutaneous layer. Cellulitis is most commonly caused by a mixed infection of *S. aureus* in conjunction with *S. pyogenes*. Cellulitis can lead to systemic infection. Cellulitis sometimes is one aspect of synergistic bacterial gangrene. Synergistic bacterial gangrene typically is caused by a mixture of *S. aureus* and microaerophilic streptococci. Synergistic bacterial gangrene causes necrosis and treatment is limited to excision of the necrotic tissue. The condition often is fatal.

Dermonecrosis

Dermonecrosis is an infection of the skin and subcutaneous tissues, easily spreading across the fascial plane within the subcutaneous tissue. The condition causes the upper and/or lower layers of skin to become necrotic, and can spread to underlying and surrounding tissues.

Necrotizing Fasciitis

Necrotizing fasciitis is referred to as "flesh-eating disease" or "flesh eating bacteria syndrome". Necrotizing fasciitis can be caused by a polymicrobial infection (e.g., type I, caused by a mixed bacterial infection), or by a monomicrobial infection (e.g., type II, caused by a single pathogenic strain of bacteria). Many types of bacteria can cause necrotizing fasciitis, non-limiting examples of which include; Group A *streptococcus* (e.g., *Streptococcus pyogenes*), *Staphylococcus aureus, Vibrio vulnificus, Clostridium perfringens*, and *Bacteroides fragilis*. Individuals with depressed or compromised immune systems are more likely to suffer from dermonecrosis (e.g., necrotizing fasciitis).

Historically, Group A *streptococcus* was diagnosed as the cause of the majority of cases of Type II dermonecrotic infections. However, since 2001, methicillin-resistant *Staphylococcus aureus* (MRSA) has been observed with increasing frequency as the cause of monomicrobial necrotizing fasciitis. The infection begins locally, sometimes at a site of trauma, which may be severe (such as the result of surgery), minor, or even non-apparent. Patients usually complain of intense pain that may seem in excess given the external appearance of the skin. With progression of the disease, tissue becomes swollen, often within hours. Diarrhea and vomiting are also common symptoms.

Sign of inflammation may not be apparent in the early stages of infection, if the bacteria are deep within the tissue. If the bacteria are not deep, signs of inflammation, such as redness and swollen or hot skin, show very quickly. Skin color may progress to violet, and blisters may form, with subsequent necrosis (e.g., death) of the subcutaneous tissues. Patients with necrotizing fasciitis typically have a fever and appear very ill. Mortality rates have been noted as high as 73 percent if left untreated. Without proper medical assistance, the infection progresses rapidly and eventually leads to death.

Pneumonia

*S. aureus* also has been diagnosed as a cause of Staphylococcal pneumonia. *Staphylococcus* pneumonia causes inflammation and swelling of the lung, which in turn causes fluid to collect in the lung. Fluid collecting in the lung can prevent oxygen from entering the bloodstream. Those with influenza are at risk for developing bacterial pneumonia. *Staphylococcus aureus* is the most common cause of bacterial pneumonia in those already suffering from influenza. Common symptoms of *staphylococcus* pneumonia include coughing, difficulty breathing, and fever. Additional symptoms include fatigue, yellow or bloody mucus, and chest pain that worsens with breathing. Methicillin resistant *S. aureus* (MRSA) is increasingly being diagnosed as the strain identified in staphylococcal pneumonia.

Surgical Wound Infections

Surgical wounds often penetrate far into the body. Infection of such wounds thus pose a grave risk to a patient, if the wound becomes infected. *S. aureus* is frequently a causative agent of infections in surgical wounds. *S. aureus* is unusually adept at invading surgical wounds, sutured wounds can be infected by far fewer *S. aureus* cells then are necessary to cause infection in normal skin. Invasion of surgical wound can lead to severe *S. aureus* septicemia. Invasion of the blood stream by *S. aureus* can lead to seeding and infection of internal organs, particularly heart valves and bone, causing systemic diseases, such as endocarditis and osteomyelitis.

Scalded Skin Syndrome

*S. aureus* is likely a major causative agent of, if not the causative agent, of "scalded skin syndrome", also referred to as "staphylococcal scalded skin syndrome", "toxic epidermal necrosis", "localized bullous impetigo", "Ritter's disease" and "Lyell's disease". Scalded skin syndrome frequently occurs in older children, typically in outbreaks caused by flowering of *S. aureus* strains that produce epidermolytic exotoxins (e.g., exfoliatin A and B, sometimes referred to as scalded skin syndrome toxin), which cause detachment within the epidermal layer. One of the exotoxins is encoded by the bacterial chromosome and the other is encoded by a plasmid. The exotoxins are proteases that cleave desmoglein-1, which normally holds the granulosum and spinosum layers of the skin together.

The bacteria may initially infect only a minor lesion, however, the toxin destroys intercellular connections, spreads epidermal layers and allows the infection to penetrate the outer layer of the skin, producing the desquamation that typifies the disease. Shedding of the outer layer of skin generally reveals normal skin below, but fluid lost in the process can produce severe injury in young children if it is not treated properly.

Toxic Shock Syndrome

Toxic shock syndrome (TSS) is caused by strains of *S. aureus* that produce the so-called "toxic shock syndrome toxin". The disease can be caused by *S. aureus* infection at any site, but is often erroneously viewed exclusively as a disease solely of women who use tampons. The disease involves toxemia and septicemia, and can be fatal.

Symptoms of toxic shock syndrome vary depending on the underlying cause. TSS resulting from infection with the bacteria *Staphylococcus aureus* typically manifests in otherwise healthy individuals with high fever, accompanied by low blood pressure, malaise and confusion, which can rapidly progress to stupor, coma, and multi-organ failure. The characteristic rash, often seen early in the course of illness, resembles a sunburn, and can involve any region of the body, including the lips, mouth, eyes, palms and soles. In patients who survive the initial onslaught of the infection, the rash desquamates, or peels off, after 10-14 days.

As noted above, due to the increase of multi-drug resistant strains of *S. aureus*, an increasing number of antibiotics commonly used to treat *S. aureus* infections, no longer control or eliminate infections of methicillin and multidrug resistant *Staphylococcus aureus*. Antibodies against *S. aureus* alpha toxin described herein can help reduce the severity of infection and also may aid in clearing, preventing (prophylatically) or reducing pathogenic *S. aureus* from an infected host.

Antibodies

As used herein, the terms "antibody," "antibodies" (also known as immunoglobulins) and "antigen-binding fragments," encompass monoclonal antibodies (including full-length monoclonal antibodies), polyclonal antibodies, multispecific antibodies formed from at least two different epitope binding fragments (e.g., bispecific antibodies), human antibodies, humanized antibodies, camelid antibodies, chimeric antibodies, single-chain Fvs (scFv), single-chain antibodies, single domain antibodies, domain antibodies, Fab fragments, F(ab')2 fragments, antibody fragments that exhibit the desired biological activity (e.g., the antigen binding portion), disulfide-linked Fvs (dsFv), and anti-idiotypic (anti-Id) antibodies (including, e.g., anti-Id antibodies to antibodies herein provided), intrabodies, and epitope-binding fragments of any of the above. In particular, antibodies include immunoglobulin molecules and immunologically active fragments of immunoglobulin molecules, i.e., molecules that contain at least one antigen-binding site. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)). Antibodies may be derived from any mammal, including, but not limited to, humans, monkeys, pigs, horses, rabbits, dogs, cats, mice, and the like, or other animals such as birds (e.g., chickens).

Native antibodies generally are heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains (CH). Each light chain has a variable domain at one end (VL) and a constant domain (CL) at its other end. The constant domain of the light chain is aligned with the first constant domain of the heavy chain, and the light chain variable domain is aligned with the variable domain of the heavy chain. Light chains are classified as lambda chains or kappa chains based on the amino acid sequence of the light chain constant region. The variable domain of a kappa light chain may also be denoted herein as VK.

Antibodies provided herein include full length or intact antibody, antibody fragments, native sequence antibody or amino acid variants, human, humanized, post-translationally modified, chimeric or fusion antibodies, immunoconjugates, and functional fragments thereof. The antibodies can be modified in the Fc region, and certain modifications can provide desired effector functions or serum half-life.

Antibodies having one or more biological characteristics (e.g., potency, alpha toxin affinity, effector function, ortholog binding affinity, neutralization, inhibition of alpha toxin heptamer formation, and the like) of the present anti-alpha toxin antibodies and fragments also are contemplated. Anti-alpha toxin antibodies and fragments can be used for diagnosing and/or treating and/or alleviating and/or preventing one or more symptoms of the *Staphylococcus aureus* associated disease in a mammal, as described above.

Provided herein is a composition comprising an anti-alpha toxin antibody or fragment and a carrier. For the purposes of treating *S. aureus*-associated disease, compositions can be administered to a patient in need of such treatment, where the composition can comprise one or more anti-alpha toxin antibodies and/or fragments thereof. Also provided are formulations comprising an anti-alpha toxin antibody or fragment thereof as presented herein and a carrier. In some embodiments, the formulation is a prophylactic or therapeutic formulation comprising a pharmaceutically acceptable carrier.

In certain embodiments, methods provided here are useful for treating a *Staphylococcus aureus* associated and/or an alpha toxin associated disease/condition and/or preventing and/or alleviating one or more symptoms of the disease or condition in a mammal, comprising administering a therapeutically effective amount of an anti-alpha toxin antibody or fragment to the mammal. The antibody prophylactic or therapeutic compositions can be administered short term (acute) or chronic, or intermittently as directed by a physician.

In certain embodiments articles of manufacture comprise at least an anti-alpha toxin antibody or fragment, such as in sterile dosage form and/or in a kit. A kit containing an anti-alpha toxin antibody or fragment can find use, for example, for *S. aureus* cell killing assays, for purification or immunoprecipitation of alpha toxin from cells. For example, for isolation and purification of alpha toxin, a kit can contain an anti-alpha toxin antibody or fragment coupled to beads (e.g., sepharose beads). A kit can contain an antibody for detection and quantification of *S. aureus* and/or alpha toxin in vitro, e.g., in an ELISA or a Western blot. Such an antibody useful for detection may be provided with a label such as a fluorescent or radiolabel.

TERMINOLOGY

It is to be understood that the method provided herein is not limited to specific compositions or process steps, as such may vary. It is noted that, as used in this specification and the appended claims, the singular form "a", "an" and "the" include singular and plural referents unless the context clearly dictates otherwise.

An isolated antibody, or antigen-binding fragment thereof, which specifically binds an alpha toxin polypeptide (e.g., alpha toxin monomer, is referred to herein as an "anti-alpha toxin antibody or fragment" in singular form and as "anti-alpha toxin antibodies and fragments" in plural form). The alpha toxin polypeptides sometimes are referred to as alpha hemolysin. Alpha toxin forms pores in cell membranes after oligomerizing into a heptamer, where the oligomerized polypeptides sometimes are referred to collectively as an "alpha toxin pore", or "alpha toxin heptamer".

Amino acids often are referred to herein by commonly known three letter symbols or by the one-letter symbols recommended by the IUPAC-IUB Biochemical Nomenclature Commission. Nucleotides, likewise, often are referred to by commonly accepted single-letter codes.

The numbering of amino acids in the variable domain, complementarity determining region (CDRs) and framework regions (FR), of an antibody follow, unless otherwise indicated, the Kabat definition as set forth in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insertion (residue 52a according to Kabat) after residue 52 of H2 and inserted residues (e.g., residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. Maximal alignment of framework residues frequently requires the insertion of "spacer" residues in the numbering system, to be used for the Fv region. In addition, the identity of certain individual residues at any given Kabat site number may vary from antibody chain to antibody chain due to interspecies or allelic divergence.

Anti-Alpha Toxin Antibodies and Fragments

In certain embodiments, an anti-alpha toxin antibody or fragment is isolated and/or purified and/or pyrogen-free. The term "purified" as used herein, refers to a molecule of interest, that has been identified and separated and/or recovered from a component of its natural environment. Thus, in some embodiments, an antibody provided is a purified antibody where it has been separated from one or more components of its natural environment. The term "isolated antibody" as used herein refers to an antibody which is substantially free of other antibody molecules having different antigenic specificities (e.g., an isolated antibody that specifically binds to alpha toxin is substantially free of antibodies that specifically bind antigens other than alpha toxin). A bi- or multi-specific antibody molecule is an isolated antibody when substantially free of other antibody molecules. Thus, in some embodiments, antibodies provided are isolated antibodies where they have been separated from antibodies with a different specificity. An isolated antibody may be a monoclonal antibody. An isolated antibody that specifically binds to an epitope, isoform or variant of *S. aureus* alpha toxin may, however, have cross-reactivity to other related antigens, e.g., from other species (e.g., *Staphylococcus* species homologs). An isolated antibody as provided may be substantially free of one or more other cellular materials. In some embodiments, a combination of "isolated" monoclonal antibodies is provided, and pertains to antibodies having different specificities and combined in a defined composition. Methods of production and purification/isolation of an anti-alpha toxin antibody or fragment are described herein in more detail.

Isolated antibodies presented comprise antibody amino acid sequences disclosed herein, which can be encoded by any suitable polynucleotide. Isolated antibodies sometimes are provided in formulated form. In some embodiments, an anti-alpha toxin antibody or fragment binds *S. aureus* alpha toxin and, thereby partially or substantially alters at least one biological activity of the alpha toxin, for example, oligomerization into the active heptamer complex.

Anti-alpha toxin antibody or fragment often immunospecifically binds to one or more epitopes specific to the alpha toxin protein, peptide, subunit, fragment, portion, oligomers or any combination thereof and generally do not specifically bind to other polypeptides. The term "oligomers" or "alpha toxin oligomers" refers to an association of alpha toxin monomers (e.g., 2 monomers, 3 monomers, 4 monomers, 5 monomers, 6 monomers or 7 monomers) to form a functional pore (e.g., 7 alpha toxin monomers). An epitope can comprise at least one antibody binding region that comprises at least one portion of the alpha toxin protein. The term "epitope" as used herein refers to a protein determinant capable of binding to an antibody. Epitopes generally include chemically active surface groupings of molecules such as amino acids and/or sugar side chains and generally have specific three dimensional structural characteristics, as well as specific chemical characteristics (e.g., charge, polarity, basic, acidic, hydrophobicity and the like). Conformational and non-conformational epitopes are distinguished in that the binding to the former but not the latter is lost in the presence of denaturing solvents. In some embodiments, the epitope recognized interferes with formation of the active heptamer (e.g., inhibits oligomerization of alpha toxin monomers into an active heptamer complex), In certain embodiments, an epitope is comprised of at least a portion of the alpha toxin protein, which is involved in formation of an alpha toxin heptamer complex. A specified epitope can comprise any combination of at least one amino acid sequence of at least 3 amino acid residues to the entire specified portion of contiguous amino acids of the alpha toxin protein. In some embodiments, the epitope is at least 4 amino acid residues, at least 5 amino acid residues, at least 6 amino acid residues, at least 7 amino acid residues, at least 8 amino acid residues, at least 9 amino acid residues, at least 10 amino acid residues, at least 11 amino acid residues, at least 12 amino acid residues, at least 13 amino acid residues, at least 14 amino acid residues, or at least 15 amino acid residues to the entire specified portion of contiguous amino acids of the alpha toxin protein. In certain other embodiments, the epitope comprises 1, 2, 3, 4, 5, 6, 7, 8, 9, 10, 11, 12, 13, 14 or 15 contiguous or non-contiguous amino acid residues. In further embodiments, the amino acid residues comprised within the epitope are involved in alpha toxin heptamer complex formation. In certain embodiments, the contact residues comprise T261, T263, N264, K266 and K271. In other embodiments, the contact residues comprise N177, W179, G180, P181, Y182, D183, D185, S186, W187, N188, P189, V190, Y191 and R200 of SEQ ID NO: 39. In further embodiments, the contact residues comprises N177, W179, G180, P181, Y182, D183, D185, S186, W187, N188, P189, V190, Y191, R200, T261, T263, N264, K266 and K271 of SEQ ID NO: 39. In certain embodiments, the portion of the alpha toxin in contact with the antibody or antigen-binding fragment thereof comprises amino acids 261-272 of SEQ ID NO: 39. In other embodiments, the portion of the alpha toxin in contact with the antibody or antigen-binding fragment thereof comprises amino acids 248-277 of SEQ ID NO: 39. In other embodiments, the portion of the alpha toxin in contact with the antibody or antigen-binding fragment thereof comprises amino acids 173-201 and 261-272 of SEQ ID NO: 39.

Thus, in specific embodiments, isolated/purified anti-alpha toxin antibodies and fragments immunospecifically bind to a molecule comprising the amino acid sequence according to SEQ ID NO: 39 and/or to a molecule comprising the amino acid sequence according to SEQ ID NO: 40. In certain embodiments, anti-alpha toxin antibodies and fragments also bind alpha toxin homologs or orthologs from different species, or to variants of the amino acid sequence of SEQ ID NO: 39, where the histidine at position 35 is replaced with leucine, or replaced with other amino acids corresponding to H35 mutations known to one of ordinary skill in the art.

Variable Regions

In certain embodiments, an anti-alpha toxin antibody or fragment is prepared from a parent antibody. In some embodiments, the anti-alpha toxin antibody or fragment is encompassed within the parent antibody. As used herein, the term "parent antibody" refers to an antibody that is encoded by an amino acid sequence used for the preparation of the variant or derivative, defined herein. A parent polypeptide may comprise a native antibody sequence (i.e., a naturally occurring, including a naturally occurring allelic variant) or an antibody sequence with pre-existing amino acid sequence modifications (such as other insertions, deletions and/or substitutions) of a naturally occurring sequence. A parent antibody may be a humanized antibody or a human antibody. In specific embodiments, anti-alpha toxin antibodies and fragments are variants of the parent antibody. As used herein, the term "variant" refers to an anti-alpha toxin antibody or fragment that differs in amino acid sequence from a "parent" anti-alpha toxin antibody or fragment amino acid sequence by virtue of addition, deletion and/or substitution of one or more amino acid residue(s) in the parent antibody sequence.

The antigen-binding portion of an antibody comprises one or more fragments of an antibody that retain the ability to specifically bind to an antigen (e.g., alpha toxin). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; and (vi) an isolated complementarity determining region (CDR). Although the two domains of the Fv fragment, VL and VH, often are coded for by separate genes, they can be joined, using recombinant methods, by a synthetic linker that enables them to be made as a single protein chain in which the VL and VH regions pair to form monovalent molecules (known as single chain Fv (scFv). Such single chain antibodies also are encompassed within the terms "antibody and "antigen-binding portion" of an antibody. These antibody fragments can be obtained using known techniques, and the fragments can be screened for binding activity in the same manner as are intact antibodies. Antigen-binding portions can be produced by recombinant DNA techniques, or by enzymatic or chemical cleavage of intact immunoglobulins.

The present anti-alpha toxin antibodies and fragments comprise at least one antigen binding domain. In some embodiments, an anti-alpha toxin antibody or fragment comprises a VH comprising the amino acid sequence of SEQ ID NO: 20, 22, 24, 26, 28, 41, 43, 45, 47, 49, 51, 53, 55, 57, 79, 59, 61, or 62. In certain embodiments, an anti-alpha toxin antibody or fragment comprises a VL comprising the amino acid sequence of SEQ ID NO: 19, 21, 23, 25, 27, 42, 44, 46, 48, 50, 52, 54, 56, 58, 60 or 63. In yet another embodiment, an anti-alpha toxin antibody or fragment comprises a VH comprising the amino acid sequence of SEQ ID NO: 20, 22, 24, 26, 28, 41, 43, 45, 47, 49, 51, 53, 55, 57, 79, 59, 61, or 62 and a VL comprising the amino acid sequence of SEQ ID NO: 19, 21, 23, 25, 27, 42, 44, 46, 48, 50, 52, 54, 56, 58, 60 or 63. See Example 11, Table 7 for a representation of VH and VL sequences as presented herein which can be present in any combination to form an anti-alpha toxin antibody or fragment, or present in a combination to form a mAb of the invention. In some embodiments, the VH is selected from SEQ ID NO: 20, 22, 24, 26, 28, 41, 43, 45, 47, 49, 51, 53, 55, 57, 79, 59, 61, or 62. In various embodiments, the VL is selected from SEQ ID NO: 19, 21, 23, 25, 27, 42, 44, 46, 48, 50, 52, 54, 56, 58, 60 or 63. Certain VH and VL nucleotide sequences are presented in Example 11, Table 8.

In some embodiments, the isolated antibody or antigen-binding fragment thereof comprises a VH and a VL, where the VH and VL have amino acid sequences represented by SEQ ID NOs: 20 and 19; SEQ ID NOs; 22 and 21; SEQ ID NOs: 24 and 23; SEQ ID NOs: 26 and 25; SEQ ID NOs: 28 and 27; SEQ ID NOs: 41 and 42; SEQ ID NOs: 43 and 44; SEQ ID NOs: 45 and 46; SEQ ID NOs: 47 and 48; SEQ ID NOs: 47 and 48; SEQ ID NOs: 49 and 50; SEQ ID NOs: 51 and 52; SEQ ID NOs: 51 and 52; SEQ ID NOs: 53 and 54; SEQ ID NOs: 55 and 56; SEQ ID NOs: 57 and 58; SEQ ID NOs: 59 and 60; SEQ ID NOs: 61 and 58; SEQ ID NOs: 62 and 58; SEQ ID NOs: 62 and 63; SEQ ID NOs: 79 and 63.

Tables 1-7 of Example 11 provide heavy chain variable regions (VH), light chain variable regions (VL), and complementarity determining regions (CDRs) for certain embodiments of the antibodies and fragments presented herein. In certain embodiments, anti-alpha toxin antibodies and fragments comprise a VH and/or VL that has a given percent identify to at least one of the VH and/or VL sequences disclosed in Table 7. As used herein, the term "percent (%) sequence identity", also including "homology" is defined as the percentage of amino acid residues or nucleotides in a candidate sequence that are identical with the amino acid residues or nucleotides in the reference sequences, such as parent antibody sequence, after aligning the sequences and introducing gaps, if necessary, to achieve the maximum percent sequence identity, and not considering any conservative substitutions as part of the sequence identity. Optimal alignment of the sequences for comparison may be produced, besides manually, by means of local homology algorithms known in the art or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

In some embodiments, an anti-alpha toxin antibody or fragment comprises a VH amino acid sequence comprising at least 65%, 70%, 75%, 80%, 85%, 90%, 95% identity to, or comprising 100% identity to, the amino acid sequence of SEQ ID NOs: 20, 22, 24, 26, 28, 41, 43, 45, 47, 49, 51, 53, 55, 57, 79, 59, 61, or 62. In some embodiments, an anti-alpha toxin antibody or fragment includes a VH amino acid sequence at least 90%, 91%, 92%, 93%, 94%, 95%, 96%, 97%, 98%, 99% identical to, or 100% identical to, the amino acid sequence of SEQ ID NOs: 20, 22, 24, 26, 28, 41, 43, 45, 47, 49, 51, 53, 55, 57, 79, 59, 61, or 62. In certain embodiments an anti-alpha toxin antibody or fragment comprises 1-10 conservative substitutions in the amino acid sequence of SEQ ID NOs: 20, 22, 24, 26, 28, 41, 43, 45, 47, 49, 51, 53, 55, 57, 79, 59, 61, or 62. In certain embodiments, an anti-alpha toxin antibody or fragment comprising a VH amino acid sequence with a given percent identify to SEQ ID NOs: 20, 22, 24, 26, 28, 41, 43, 45, 47, 49, 51, 53, 55, 57, 79, 59, 61, or 62 has one or more characteristics (described in more detail below) selected from the group consisting of:

(a) affinity constant ($K_D$) for alpha toxin of about 13 nM or less;
(b) binds to alpha toxin monomers, but does not inhibit binding of alpha toxin to alpha toxin receptor;
(c) inhibits the formation of alpha toxin oligomers by at least 50%, 60%, 70%, 80%, 90% or 95%;
(d) reduces alpha toxin cytolytic activity by at least 50%, 60%, 70%, 80%, 90% or 95% (e.g., as determined by cell lysis add hemolysis assays);
(e) reduces cell infiltration and pro-inflammatory cytokine release (e.g., in an animal pneumonia model).

In some embodiments an isolated antibody or antigen-binding fragment thereof binds an antigen (e.g., alpha toxin) with an affinity characterized by a disassociation constant ($K_D$) in the range of about 0.01 nM to about 50 nM, 0.05 nM, 0.1 nM, 0.5 nM, 1 nN, 5 nM, 10 nM, 20 nM, 30 nM, or 40 nM.

In certain embodiments, an anti-alpha toxin antibody or fragment comprises a VL amino acid sequence at least 65%, 70%, 75%, 80%, 85%, 90%, 95% identical to, or 100% identical to, the amino acid sequence of SEQ ID NOs: 19, 21, 23, 25, 27, 42, 44, 46, 48, 50, 52, 54, 56, 58, 60 or 63. In some embodiments, an anti-alpha toxin antibody or fragment includes a VL amino acid sequence is at least 90%, 91%, 92%, 93%, 94%, 95%, 96%, 97%, 98%, 99% identical to, or 100% identical to the amino acid sequence of SEQ ID NOs: 19, 21, 23, 25, 27, 42, 44, 46, 48, 50, 52, 54, 56, 58, 60 or 63. In various embodiments the anti-alpha toxin antibody or fragment comprises 1-10 conservative substitutions in the amino acid sequence of SEQ ID NOs: 19, 21, 23, 25, 27, 42, 44, 46, 48, 50, 52, 54, 56, 58, 60 or 63. In certain embodiments, the anti-alpha toxin antibody or fragment comprising a VL amino acid sequence with a given percent identify to SEQ ID NOs: 19, 21, 23, 25, 27, 42, 44, 46, 48, 50, 52, 54, 56, 58, 60 or 63 and has one or more characteristics (described in more detail below) selected from the group consisting of:

(a) affinity constant ($K_D$) for alpha toxin of about 13 nM or less;
(b) binds to alpha toxin monomers, but does not inhibit binding of alpha toxin to alpha toxin receptor;
(c) inhibits the formation of alpha toxin oligomers by at least 50%, 60%, 70%, 80%, 90% or 95%;
(d) reduces alpha toxin cytolytic activity by at least 50%, 60%, 70%, 80%, 90% or 95%; (e.g., as determined by cell lysis add hemolysis assays);
(e) reduces cell infiltration and pro-inflammatory cytokine release (e.g., in animal pneumonia model).

In some embodiments an isolated antibody or antigen-binding fragment thereof binds an antigen (e.g., alpha toxin) with an affinity characterized by a disassociation constant ($K_D$) in the range of about 0.01 nM to about 50 nM, 0.05 nM, 0.1 nM, 0.5 nM, 1 nN, 5 nM, 10 nM, 20 nM, 30 nM, or 40 nM.

In specific embodiments an antibody or antibody fragment immunospecifically binds to alpha toxin and comprises a heavy chain variable domain comprising at least 90% identity to the amino acid sequence of SEQ ID NO: 20, 22, 24, 26, 28, 41, 43, 45, 47, 49, 51, 53, 55, 57, 79, 59, 61, or 62 and comprises a light chain variable domain comprising at least 90% identity to the amino acid sequence of SEQ ID NO: 19, 21, 23, 25, 27, 42, 44, 46, 48, 50, 52, 54, 56, 58, 60 or 63, where the antibody has the activity of inhibiting the binding of one or more alpha toxin monomers to each other (e.g., inhibits oligomerization).

Complementarity Determining Regions

While the variable domain (VH and VL) comprises the antigen-binding region, the variability is not evenly distributed through the variable domains of antibodies. It is concentrated in segments called Complementarity Determining Regions (CDRs), both in the light chain (VL or VK) and the heavy chain (VH) variable domains. The more highly conserved portions of the variable domains are called the framework regions (FR). The variable domains of native heavy and light chains each comprise four FR, largely adopting a β-sheet configuration, connected by three CDRs, which form loops connecting, and in some cases forming part of, the beta-sheet structure. The CDRs in each chain are held together in close proximity by the FR and, with the CDRs from the other chain, contribute to the formation of the antigen-binding site of antibodies (see, Kabat et al., supra). The three CDRs of the heavy chain are designated VH-CDR1, VH CDR2, and VH-CDR-3, and the three CDRs of the light chain are designated VL-CDR1, VL-CDR2, and VI-CDR3. The Kabat numbering system is used herein. As such, VH-CDR1 begins at approximately amino acid 31 (i.e., approximately 9 residues after the first cysteine residue), includes approximately 5-7 amino acids, and ends at the next serine residue. VH-CDR2 begins at the fifteenth residue after the end of CDR-H1, includes approximately 16-19 amino acids, and ends at the next glycine residue. VH-CDR3 begins at approximately the thirtieth amino acid residue after the end of VH-CDR2; includes approximately 13-15 amino acids; and ends at the sequence M-D-V. VL-CDR1 begins at approximately residue 24 (i.e., following a cysteine residue); includes approximately 10-15 residues; and ends with the sequence Y—V—S. VL-CDR2 begins at approximately the sixteenth residue after the end of VL-CDR1 and includes approximately 7 residues. VL-CDR3 begins at approximately the thirty third residue after the end of VH-CDR2; includes approximately 7-11 residues and ends at the sequence T-1-L. Note that CDRs vary considerably from antibody to antibody (and by definition will not exhibit homology with the Kabat consensus sequences).

The present anti-alpha toxin antibodies and fragments comprise at least one antigen binding domain that includes at least one complementarity determining region (CDR1, CDR2 or CDR3). In some embodiments, an anti-alpha toxin antibody or fragment comprises a VH that includes at least one VH CDR (e.g., CDR-H1, CDR-H2 or CDR-H3). In certain embodiments, an anti-alpha toxin antibody or fragment comprises a VL that includes at least one VL CDR (e.g., CDR-L1, CDR-L2 or CDR-L3).

In some embodiments, the isolated antibody or antigen-binding fragment thereof that immunospecifically binds to a *Staphylococcus aureus* alpha toxin polypeptide includes, (a) a VH CDR1 comprising an amino acid sequence identical to, or comprising 1, 2, or 3 amino acid residue substitutions relative to SEQ ID NO: 7, 10, 13 or 69; (b) a VH CDR2 comprising an amino acid sequence identical to, or comprising 1, 2, or 3 amino acid residue substitutions relative to SEQ ID NO: 8, 11, 14, 17, 70 or 75; and (c) a VH CDR3 comprising an amino acid sequence identical to, or comprising 1, 2, or 3 amino acid residue substitutions relative to SEQ ID NO: 9, 12, 15, 18, 16, 65, 66, 67, 71, 72, 76 or 78.

In particular embodiments, the isolated antibody or antigen-binding fragment thereof comprises a VH CDR1, VH CDR2 and VH CDR3 comprising amino acid sequences identical to, or comprising 1, 2, or 3 amino acid residue substitutions in each CDR relative to SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs 7, 8, and 67; SEQ ID NOs: 7, 8 and 78; SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

In some embodiments, the isolated antibody or antigen-binding fragment thereof that immunospecifically binds to a *Staphylococcus aureus* alpha toxin polypeptide includes, (a) a VL CDR1 comprising an amino acid sequence identical to, or comprising 1, 2, or 3 amino acid residue substitutions relative to SEQ ID NO: 1 or 4; (b) a VL CDR2 comprising an amino acid sequence identical to, or comprising 1, 2, or 3 amino acid residue substitutions relative to SEQ ID NO: 2, 5, 73 or 77; and (c) a VL CDR3 comprising an amino acid sequence identical to, or comprising 1, 2, or 3 amino acid residue substitutions relative to SEQ ID NO: 3, 6, 64, 68 or 74.

In particular embodiments, the isolated antibody or antigen-binding fragment thereof comprises a VL CDR1, VL CDR2 and VL CDR3 comprising amino acid sequences identical to, or comprising 1, 2, or 3 amino acid residue substitutions in each CDR relative to SEQ ID NOs: 1, 2 and 3; SEQ ID NOs: 4, 5 and 6; SEQ ID NOs: 1, 2 and 64; SEQ ID NOs: 1, 2 and 68; SEQ ID NOs: 1, 73 and 74; or SEQ ID NOs: 1, 77 and 74.

In some embodiments, the isolated antibody or antigen-binding fragment thereof that immunospecifically binds to a *Staphylococcus aureus* alpha toxin polypeptide comprises a VH CDR1, VH CDR2, VH CDR3, VL CDR1, VL CDR2 and VL CDR3 comprising amino acid sequences identical to, or comprising 1, 2, or 3 amino acid residue substitutions in each CDR relative to: (a) a VH CDR1 comprising the amino acid sequence of SEQ ID NO: 7, 10, 13 or 69; (b) a VH CDR2 comprising the amino acid sequence of SEQ ID NO: 8, 11, 14, 17, 70 or 75; (c) a VH CDR3 comprising the amino acid sequence of SEQ ID NO: 9, 12, 15, 18, 16, 65, 66, 67, 71, 72, 76 or 78; (d) a VL CDR1 comprising the amino acid sequence of SEQ ID NO: 1 or 4; (e) a VL CDR2 comprising the amino acid sequence of SEQ ID NO: 2, 5, 73, or 77; and (f) a VL CDR3 comprising the amino acid sequence of SEQ ID NO: 3, 6, 64, 68 or 74.

In particular embodiments, the isolated antibody or antigen-binding fragment thereof comprises a VH CDR1, VH CDR2, VH CDR3, VL CDR1, VL CDR2, and VL CDR3 comprising amino acid sequences identical to, or comprising 1, 2, or 3 amino acid residue substitutions in each CDR relative to SEQ ID NOs: 7, 8, 9, 1, 2 and 3; SEQ ID NOs: 10, 11, 12, 1, 2 and 3; SEQ ID NOs: 13, 14, 15, 4, 5 and 6; SEQ ID NOs: 7, 17, 18, 1, 2 and 3; SEQ ID NOs: 7, 8, 16, 1, 2 and 64; SEQ ID NOs: 7, 8, 65, 1, 2 and 64; SEQ ID NOs: 7, 8, 66, 1, 2 and 64; SEQ ID NOs: 7, 8, 67, 1, 2 and 64; SEQ ID NOs: 7, 8, 67, 1, 2 and 68; SEQ ID NOs: 7, 8, 78, 1, 2 and 64; SEQ ID NOs: 7, 8, 65, 1, 2 and 68; SEQ ID NOs: 69, 70, 71, 1, 2 and 68; SEQ ID NOs: 7, 8, 72, 1, 73 and 74; SEQ ID NOs: 69, 75, 71, 1, 2 and 68; SEQ ID NOs: 69, 75, 76, 1, 2 and 68; SEQ ID NOs: 69, 75, 76, 1, 77 and 74; SEQ ID NOs: 69, 70, 71, 1, 77 and 74, In some embodiments, provided is a composition that comprises an isolated antibody or antigen-binding fragment thereof that (i) includes a VH chain domain comprising three CDRs and a VL chain domain comprising three CDRs; and (ii) immunospecifically binds to a *Staphylococcus aureus* alpha toxin polypeptide, where the three CDRs of the VH chain domain include (a) a VH CDR1 comprising the amino acid sequence of SEQ ID NO: 7, 10, 13 or 69; (b) a VH CDR2 comprising the amino acid sequence of SEQ ID NO: 8, 11, 14, 17, 70 or 75; and (c) a VH CDR3 comprising the amino acid sequence of SEQ ID NO: 9, 12, 15, 18, 16, 65, 66, 67, 71, 72, 76 or 78. In particular embodiments, the VH CDR1, VH CDR2 and VH CDR3 correspond to SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs 7, 8, and 67; SEQ ID NOs: 7, 8 and 78;

SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

Also provided in certain embodiments is a composition that comprises an isolated antibody or antigen-binding fragment thereof that (i) includes a VH chain domain comprising three CDRs and a VL chain domain comprising three CDRs; and (ii) immunospecifically binds to a *Staphylococcus aureus* alpha toxin polypeptide, where the three CDRs of the VL chain domain include (a) a VL CDR1 comprising the amino acid sequence of SEQ ID NO: 1 or 4; (b) a VL CDR2 comprising the amino acid sequence of SEQ ID NO: 2, 5, 73, or 77; and (c) a VL CDR3 comprising the amino acid sequence of SEQ ID NO: 3, 6, 64, 68 or 74. In particular embodiments, the VL CDR1, VL CDR2 and VL CDR3 correspond to SEQ ID NOs: 1, 2 and 3; SEQ ID NOs: 4, 5 and 6; SEQ ID NOs: 1, 2 and 64; SEQ ID NOs: 1, 2 and 68; SEQ ID NOs: 1, 73 and 74; or SEQ ID NOs: 1, 77 and 74.

In certain embodiments, an anti-alpha toxin antibody or fragment immunospecifically binds *S. aureus* alpha toxin and comprises (a) a VH CDR1 comprising an amino acid sequence identical to, or comprising 1, 2, or 3 amino acid residue substitutions relative to SEQ ID NO: 7, 10, 13 or 69; (b) a VH CDR2 comprising an amino acid sequence identical to, or comprising 1, 2, or 3 amino acid residue substitutions relative to SEQ ID NO: 8, 11, 14, 17, 70 or 75; and (c) a VH CDR3 comprising an amino acid sequence identical to, or comprising 1, 2, or 3 amino acid residue substitutions relative to SEQ ID NO: 9, 12, 15, 18, 16, 65, 66, 67, 71, 72, 76 or 78; (d) a VL CDR1 comprising the amino acid sequence of SEQ ID NO: 1 or 4; (e) a VL CDR2 comprising the amino acid sequence of SEQ ID NO: 2, 5, 73, or 77; and (f) a VL CDR3 comprising the amino acid sequence of SEQ ID NO: 3, 6, 64, 68 or 74 and has one or more characteristics (described in more detail below) selected from the group consisting of:

(a) affinity constant ($K_D$) for alpha toxin of about 13 nM or less;
(b) binds to alpha toxin monomers, but does not inhibit binding of alpha toxin to alpha toxin receptor;
(c) inhibits the formation of alpha toxin oligomers by at least 50%, 60%, 70%, 80%, 90% or 95%;
(d) reduces alpha toxin cytolytic activity by at least 50%, 60%, 70%, 80%, 90% or 95%; (e.g., as determined by cell lysis add hemolysis assays);
(e) reduces cell infiltration and pro-inflammatory cytokine release (e.g., in animal pneumonia model).

In some embodiments an isolated antibody or antigen-binding fragment thereof binds an antigen (e.g., alpha toxin) with an affinity characterized by a disassociation constant ($K_D$) in the range of about 0.01 nM to about 50 nM, 0.05 nM, 0.1 nM, 0.5 nM, 1 nN, 5 nM, 10 nM, 20 nM, 30 nM, or 40 nM.

Example 11, Tables 1-7 provide sequences for VH CDR1, VH CDR2, VH CDR3, VL CDR1, VL CDR2 and VL CDR3 for antibodies of the present invention. Table 9 provides a summary of VH and VL CDRs. These regions can be combined in a variety of combinations as each CDR region can be independently selected for a given antibody. Table 7 illustrates different sequences that can be selected for each region. In certain embodiments VL CDR3 sequences can be present in any combination to form a present anti-alpha toxin antibody or fragment. In certain embodiments, the VH CDR1 is selected from SEQ ID NO: 7, 10, 13 or 69, the VH CDR2 is selected from SEQ ID NO: 8, 11, 14, 17, 70 or 75 and the VH CDR3 is selected from SEQ ID NO: SEQ ID NO: 9, 12, 15, 18, 16, 65, 66, 67, 71, 72, 76 or 78 as depicted in Table 9. In some embodiments, VL CDR1 is selected from SEQ ID NO: 1 or 4, the VL CDR2 is selected from SEQ ID NO: 2, 5, 73, or 77 and the VL CDR3 is selected from SEQ ID NO: 3, 6, 64, 68 or 74 as depicted in Table 9.

VH CDR3 and VL CDR3 domains play a role in the binding specificity/affinity of an antibody for an antigen. (Accordingly, in some embodiments an anti-alpha toxin antibody or fragment or antigen-binding fragment thereof comprises a VH CDR3 comprising an amino acid sequence identical to, or comprising 1, 2, or 3 amino acid residue substitutions relative to, SEQ ID NO: SEQ ID NO: 9, 12, 15, 18, 16, 65, 66, 67, 71, 72, 76 or 78. In various embodiments, an anti-alpha toxin antibody or fragment comprises a VL CDR3 comprising an amino acid sequence identical to, or comprising 1, 2, or 3 amino acid residue substitutions relative to, SEQ ID NO: 3, 6, 64, 68 or 74. The remaining portions of the anti-alpha toxin antibodies and fragments (e.g., CDR1, CDR2, VH, VL, and the like) may comprise specific sequences disclosed herein or known sequences provided the anti-alpha toxin antibodies and fragments immunospecifically bind to *S. aureus* alpha toxin.

In some embodiments, an isolated antibody or antigen-binding fragment thereof immunospecifically binds alpha toxin and comprises a VH CDR3 comprising an amino acid sequence identical to, or comprising 1, 2, or 3 amino acid residue substitutions relative to SEQ ID NO: SEQ ID NO: 9, 12, 15, 18, 16, 65, 66, 67, 71, 72, 76 or 78, where the antibody or antigen binding fragment inhibits alpha toxin oligomerization.

In some embodiments, an isolated antibody or antigen-binding fragment thereof immunospecifically binds alpha toxin and comprises a VL CDR3 comprising an amino acid sequence identical to, or comprising 1, 2, or 3 amino acid residue substitutions relative to SEQ ID NO: 3, 6, 64, 68 or 74, where the antibody or antigen binding fragment inhibits alpha toxin oligomerization.

In some embodiments, an isolated antibody or antigen-binding fragment thereof immunospecifically binds alpha toxin and comprises a VH CDR3 comprising an amino acid sequence identical to, or comprising 1, 2, or 3 amino acid residue substitutions relative to SEQ ID NO: SEQ ID NO: 9, 12, 15, 18, 16, 65, 66, 67, 71, 72, 76 or 78, where the antibody or antigen binding fragment reduces or inhibits the release of cytokines.

In some embodiments, an isolated antibody or antigen-binding fragment thereof immunospecifically binds alpha toxin and comprises a VL CDR3 comprising an amino acid sequence identical to, or comprising 1, 2, or 3 amino acid residue substitutions relative to SEQ ID NO: 3, 6, 64, 68 or 74, where the antibody or antigen binding fragment reduces or inhibits the release of cytokines.

In some embodiments, an isolated antibody or antigen-binding fragment thereof immunospecifically binds alpha toxin and comprises a VH CDR3 comprising an amino acid sequence identical to, or comprising 1, 2, or 3 amino acid residue substitutions relative to SEQ ID NO: SEQ ID NO: 9, 12, 15, 18, 16, 65, 66, 67, 71, 72, 76 or 78, where the antibody or antigen binding fragment alleviates or eliminates dermonecrosis.

In some embodiments, an isolated antibody or antigen-binding fragment thereof immunospecifically binds alpha toxin and comprises a VL CDR3 comprising an amino acid sequence identical to, or comprising 1, 2, or 3 amino acid residue substitutions relative to SEQ ID NO: 3, 6, 64, 68 or 74, where the antibody or antigen binding fragment alleviates or eliminates dermonecrosis.

Anti-alpha toxin antibodies and fragments often comprise one or more amino acid sequences substantially the same as an amino acid sequence described herein. Amino acid sequences that are substantially the same include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Framework Regions

Variable domains of the heavy and light chains each comprise four framework regions (in general FR1, FR2, FR3, FR4 or alternatively FW1, FW2, FW3, FW4), which are the more highly conserved portions of the variable domains. The four framework regions of the heavy chain are here designated VH-FW1, VH-FW2, VH-FW3 and VH-FW4, and the four framework regions of the light chain are here designated VL-FW1, VL-FW2, VL-FW3 and VH-FW4. The Kabat numbering system is used herein, and as such, VH-FW1 begins at position 1 and ends at approximately amino acid 30, VH-FW2 is approximately from amino acid 36 to 49, VH-FW3 is approximately from amino acid 66 to 94 and VH-FW4 is approximately amino acid 103 to 113. VL-FW1 begins at amino acid 1 and ends at approximately amino acid 23, VL-FW2 is approximately from amino acid 35 to 49, VL-FW3 is approximately from amino acid 57 to 88 and VL-FW4 is approximately from amino acid 98 to 107. In certain embodiments the framework regions contain substitutions according to the Kabat numbering system, e.g., insertion at 106A in VL-FW1. In addition to naturally occurring substitutions, one or more alterations (e.g., substitutions) of FR residues also may be introduced in an anti-alpha toxin antibody or fragment. In certain embodiments, these alterations result in an improvement or optimization in the binding affinity of the antibody for anti-alpha toxin. Non-limiting examples of framework region residues that can be modified include those that non-covalently bind antigen directly, interact with/effect the conformation of a CDR, and/or participate in the VL-VH interface.

In certain embodiments a framework region may comprise one or more amino acid changes for the purposes of "germlining". For example, the amino acid sequences of selected antibody heavy and light chains are compared to germline heavy and light chain amino acid sequences and where certain framework residues of the selected VL and/or VH chains differ from the germline configuration (e.g., as a result of somatic mutation of the immunoglobulin genes used to prepare the phage library), it may be desirable to "back mutate" the altered framework residues of the selected antibodies to the germline configuration (i.e., change the framework amino acid sequences of the selected antibodies so that they are the same as the germline framework amino acid sequences). Such "back mutation" (or "germlining") of framework residues can be accomplished by standard molecular biology methods for introducing specific mutations (e.g., site-directed mutagenesis; PCR-mediated mutagenesis, and the like). In some embodiments, variable light and/or heavy chain framework residues are back mutated. In certain embodiments, a variable heavy chain of an isolated antibody or antigen-binding fragment thereof presented is back mutated. In certain embodiments, a variable heavy chain of an isolated antibody or antigen-binding fragment thereof comprises at least one, at least two, at least three, at least four or more back mutations.

In certain embodiments, the VH of an anti-alpha toxin antibody or fragment presented herein may comprise FR1, FR2, FR3 and/or FR4 that has an amino acid sequence identity with the corresponding framework regions (i.e., FR1 of antibody X as compared to FR1 of antibody Y) within SEQ ID NO: 20, 22, 24, 26, 28, 41, 43, 45, 47, 49, 51, 53, 55, 57, 79, 59, 61, or 62 that is from about 65% to about 100%. In some embodiments, an anti-alpha toxin antibody or fragment comprises a VH FR amino acid sequence (FR1, FR2, FR3 and/or FR4) at least 65%, 70%, 75%, 80%, 85%, 90%, 95% identical to, or 100% identical to, the corresponding FR of VH SEQ ID NO: 20, 22, 24, 26, 28, 41, 43, 45, 47, 49, 51, 53, 55, 57, 79, 59, 61, or 62. In certain embodiments an anti-alpha toxin antibody or fragment comprises a VH FR amino acid sequence (FR1, FR2, FR3 and/or FR4) at least 90%, 91%, 92%, 93%, 94%, 95%, 96%, 97%, 98%, 99% identical to, or 100% identical to, the corresponding FR of VH SEQ ID NO: 20, 22, 24, 26, 28, 41, 43, 45, 47, 49, 51, 53, 55, 57, 79, 59, 61, or 62.

In certain embodiments, an anti-alpha toxin antibody or fragment may comprise a VH FR (FR1, FR2, FR3 and/or FR4) comprising an amino acid sequence identical to, or comprising 1, 2 or 3 amino acid substitutions relative to, the corresponding FR of VH SEQ ID NO: 20, 22, 24, 26, 28, 41, 43, 45, 47, 49, 51, 53, 55, 57, 79, 59, 61, or 62. In particular FR1, FR2, FR3 or FR4 of the VH may each have an amino acid sequence identical to or comprising 1, 2 or 3 amino acid substitutions relative to the corresponding FR1, FR2, FR3 or FR4 of VH SEQ ID NO: 20, 22, 24, 26, 28, 41, 43, 45, 47, 49, 51, 53, 55, 57, 79, 59, 61, or 62.

In certain embodiments, the VL of an anti-alpha toxin antibody or fragment herein provided may comprise FR1, FR2, FR3 and/or FR4 that has amino acid sequence identity with the corresponding framework regions (i.e., FR1 of antibody X as compared to FR1 of antibody Y) within the FR of VL SEQ ID NO: 19, 21, 23, 25, 27, 42, 44, 46, 48, 50, 52, 54, 56, 58, 60 or 63 (e.g., from about 65% to about 100% sequence identity). In some embodiments, an anti-alpha toxin antibody or fragment comprises a VL FR amino acid sequence (FR1, FR2, FR3 and/or FR4) at least 65%, 70%, 75%, 80%, 85%, 90%, 95% identical to, or 100% identical to, the corresponding FR of VL SEQ ID NO: 19, 21, 23, 25, 27, 42, 44, 46, 48, 50, 52, 54, 56, 58, 60 or 63. In certain embodiments an anti-alpha toxin antibody or fragment comprises a VL FR amino acid sequence (FR1, FR2, FR3 and/or FR4) at least 90%, 91%, 92%, 93%, 94%, 95%, 96%, 97%, 98%, 99% identical to, or 100% identical to, the corresponding FR of VL SEQ ID NO: 19, 21, 23, 25, 27, 42, 44, 46, 48, 50, 52, 54, 56, 58, 60 or 63.

In certain embodiments, an anti-alpha toxin antibody or fragment comprises a VL FR (FR1, FR2, FR3 and/or FR4) comprising an amino acid sequence identical to, or comprising 1, 2 or 3 amino acid substitutions relative to, the corresponding FR of VL SEQ ID NO: 19, 21, 23, 25, 27, 42, 44, 46, 48, 50, 52, 54, 56, 58, 60 or 63. In particular FR1, FR2, FR3 or FR4 of the VL may each have an amino acid sequence identical to, or comprising 1, 2 or 3 amino acid substitutions relative to, the corresponding FR1, FR2, FR3 or FR4 of VH SEQ ID NO: 19, 21, 23, 25, 27, 42, 44, 46, 48, 50, 52, 54, 56, 58, 60 or 63.

In certain embodiments, an isolated antibody or antigen-binding fragment thereof immunospecifically binds alpha toxin and comprises a VH FR (FR1, FR2, FR3 and/or FR4) comprising an amino acid sequence identical to, or comprising 1, 2 or 3 amino acid substitutions relative to, the corresponding FR of VH SEQ ID NO: 20, 22, 24, 26, 28, 41, 43, 45, 47, 49, 51, 53, 55, 57, 79, 59, 61, or 62 and/or VL FR (FR1, FR2, FR3 and/or FR4) comprising an amino acid sequence identical to, or comprising 1, 2 or 3 amino acid substitutions relative to, the corresponding FR of VL SEQ ID NO: 19, 21, 23, 25, 27, 42, 44, 46, 48, 50, 52, 54, 56, 58, 60 or 63 where the antibody has one or more characteristics (described in more detail below) selected from the group consisting of:

(a) affinity constant ($K_D$) for alpha toxin of about 13 nM or less;
(b) binds to alpha toxin monomers, but does not inhibit binding of alpha toxin to alpha toxin receptor;
(c) inhibits the formation of alpha toxin oligomers by at least 50%, 60%, 70%, 80%, 90% or 95%;
(d) reduces alpha toxin cytolytic activity by at least 50%, 60%, 70%, 80%, 90% or 95%; (e.g., as determined by cell lysis add hemolysis assays);
(e) reduces cell infiltration and pro-inflammatory cytokine release (e.g., in animal pneumonia model).

In some embodiments an isolated antibody or antigen-binding fragment thereof binds an antigen (e.g., alpha toxin) with an affinity characterized by a disassociation constant ($K_D$) in the range of about 0.01 nM to about 50 nM, 0.05 nM, 0.1 nM, 0.5 nM, 1 nN, 5 nM, 10 nM, 20 nM, 30 nM, or 40 nM.

Nucleotide Sequences Encoding Anti-Alpha Toxin Antibodies and Fragments

In addition to the amino acid sequences described above, further provided are nucleotide sequences corresponding to the amino acid sequences and encoding for the human, humanized and/or chimeric antibodies herein disclosed. In some embodiments, polynucleotides comprise a nucleotide sequence encoding an anti-alpha toxin antibody or fragment described herein or fragments thereof. These include, but are not limited to, nucleotide sequences that code for the above referenced amino acid sequences. The nucleotide sequences are provided in Example 11, Table 8. Thus, also provided are polynucleotide sequences encoding VH and VL framework regions including CDRs and FRs of antibodies described herein as well as expression vectors for their efficient expression in cells (e.g., mammalian cells). Methods of making an anti-alpha toxin antibody or fragment using polynucleotides are described hereafter in more detail.

Also included are polynucleotides that hybridize under stringent or lower stringency hybridization conditions, e.g., as defined herein, to polynucleotides that encode an anti-alpha toxin antibody or fragment. The term "stringency" as used herein refers to experimental conditions (e.g., temperature and salt concentration) of a hybridization experiment to denote the degree of homology between two nucleic acids; the higher the stringency, the higher percent homology between the two nucleic acids.

Stringent hybridization conditions include, but are not limited to, hybridization to filter-bound DNA in 6× sodium chloride/sodium citrate (SSC) at about 45 degrees Celsius followed by one or more washes in 0.2×SSC/0.1% SDS at about 50-65 degrees Celsius, highly stringent conditions such as hybridization to filter-bound DNA in 6×SSC at about 45 degrees Celsius followed by one or more washes in 0.1×SSC/0.2% SDS at about 65 degrees Celsius, or any other stringent hybridization conditions known.

In certain embodiments, a nucleic acid or fragment thereof may encode an anti-alpha toxin antibody or fragment and hybridize under stringent conditions to a nucleic acid including a nucleotide sequence that encodes the amino acid sequence of SEQ ID NO: 19, 21, 23, 25, 27, 42, 44, 46, 48, 50, 52, 54, 56, 58, 60 or 63.

In certain embodiments, a polynucleotide sequence may comprise a nucleotide sequence encoding an anti-alpha toxin antibody or fragment at least about 65%, 70%, 75%, 80%, 85%, 90%, 95%, or 100% identical to a nucleotide sequence that encodes the amino acid sequence of SEQ ID NO: 19, 21, 23, 25, 27, 42, 44, 46, 48, 50, 52, 54, 56, 58, 60 or 63. In some embodiments, a polynucleotide sequence may comprise a nucleotide sequence encoding an anti-alpha toxin antibody or fragment at least about 65%, 70%, 75%, 80%, 85%, 90%, 95% or 100% identical to a nucleotide sequence of SEQ ID NO: 30, 31, 32, 33, 34, 35, 36, 37 or 38. In some embodiments, an anti-alpha toxin antibody or fragment includes a nucleotide sequence comprising at least about 90%, 91%, 92%, 93%, 94%, 95%, 96%, 97%, 98%, 99% or 100% identity to a nucleotide sequence that encodes the amino acid sequence of SEQ ID NO: 19, 21, 23, 25, 27, 42, 44, 46, 48, 50, 52, 54, 56, 58, 60 or 63.

In certain embodiments, a polynucleotide sequence may comprise a nucleotide sequence encoding an anti-alpha toxin antibody or fragment at least about 65%, 70%, 75%, 80%, 85%, 90%, 95% or 100% identical to a VH nucleotide sequence that encodes the VH amino acid sequence of SEQ ID NO: 20, 22, 24, 26, 28, 41, 43, 45, 47, 49, 51, 53, 55, 57, 79, 59, 61, or 62. In some embodiments, a polynucleotide sequence may comprise a nucleotide sequence encoding an anti-alpha toxin antibody or fragment at least about 65%, 70%, 75%, 80%, 85%, 90%, 95% or 100% identical to a VH nucleotide sequence of SEQ ID NO: 30, 32, 34, 36 or 38. In some embodiments, an anti-alpha toxin antibody or fragment is encoded by a VH-encoding nucleotide sequence comprising at least about 90%, 91%, 92%, 93%, 94%, 95%, 96%, 97%, 98%, 99% or 100% identity to a nucleotide sequence that encodes the amino acid sequence of SEQ ID NO: 20, 22, 24, 26, 28, 41, 43, 45, 47, 49, 51, 53, 55, 57, 79, 59, 61, or 62.

In certain embodiments, a polynucleotide sequence may comprise a nucleotide sequence encoding an anti-alpha toxin antibody or fragment at least about 65%, 70%, 75%, 80%, 85%, 90%, 95% or 100% identical to a VL nucleotide sequence that encodes the VL amino acid sequence of SEQ ID NO: 19, 21, 23, 25, 27, 42, 44, 46, 48, 50, 52, 54, 56, 58, 60 or 63. In some embodiments, a polynucleotide sequence may comprise a nucleotide sequence encoding an anti-alpha toxin antibody or fragment at least about 65%, 70%, 75%, 80%, 85%, 90%, 95% or 100% identical to a VL nucleotide sequence of SEQ ID NO: 29, 31, 33, 35 or 37. In some embodiments, an anti-alpha toxin antibody or fragment is encoded by a VL-encoding nucleotide sequence comprising at least, 90%, 91%, 92%, 93%, 94%, 95%, 96%, 97%, 98%, 99% or 100% identity to a nucleotide sequence that encodes the amino acid sequence of SEQ ID NO: 19, 21, 23, 25, 27, 42, 44, 46, 48, 50, 52, 54, 56, 58, 60 or 63.

In particular embodiments, a polynucleotide sequence may comprise a nucleotide sequence encoding an anti-alpha toxin antibody or fragment at least about 65%, 70%, 75%, 80%, 85%, 90%, 95% or 100% identical to VH amino acid sequence and a nucleotide sequence encoding an anti-alpha toxin antibody or fragment at least about 65%, 70%, 75%, 80%, 85%, 90%, 95% or 100% identical to VL amino acid sequence, where the VH and VL sequences are represented by SEQ ID NOs: 20 and 19; SEQ ID NOs; 22 and 21; SEQ ID NOs: 24 and 23; SEQ ID NOs: 26 and 25; SEQ ID NOs: 28 and 27; SEQ ID NOs: 41 and 42; SEQ ID NOs: 43 and 44; SEQ ID NOs: 45 and 46; SEQ ID NOs: 47 and 48; SEQ ID NOs: 47 and 48; SEQ ID NOs: 49 and 50; SEQ ID NOs: 51 and 52; SEQ ID NOs: 51 and 52; SEQ ID NOs: 53 and 54; SEQ ID NOs: 55 and 56; SEQ ID NOs: 57 and 58; SEQ ID NOs: 59 and 60; SEQ ID NOs: 61 and 58; SEQ ID NOs: 62 and 58; SEQ ID NOs: 62 and 63; SEQ ID NOs: 79 and 63.

Substantially identical sequences may be polymorphic sequences, i.e., alternative sequences or alleles in a population. An allelic difference may be as small as one base pair. Substantially identical sequences may also comprise mutagenized sequences, including sequences comprising silent mutations. A mutation may comprise one or more residue changes, a deletion of one or more residues, or an insertion of one or more additional residues.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides, which, briefly, involves the synthesis of overlapping oligonucleotides containing portions of the sequence encoding the antibody, annealing and ligating of those oligonucleotides, and then amplification of the ligated oligonucleotides by PCR.

A polynucleotide encoding an antibody may also be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, sometimes polyA+ RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method known in the art.

Once the nucleotide sequence and corresponding amino acid sequence of the antibody is determined, the nucleotide sequence of the antibody may be manipulated using methods known in the art for the manipulation of nucleotide sequences, e.g., recombinant DNA techniques, site directed mutagenesis, PCR, and the like, to generate antibodies having a different amino acid sequence, for example to create amino acid substitutions, deletions, and/or insertions.

As used herein, the term "stringent conditions" refers to conditions for hybridization and washing. Methods for hybridization reaction temperature condition optimization are known to those of skill in the art. Aqueous and non-aqueous methods are described in that reference and either can be used. Non-limiting examples of stringent hybridization conditions are hybridization in 6× sodium chloride/sodium citrate (SSC) at about 45 degrees Celsius, followed by one or more washes in 0.2×SSC, 0.1% SDS at 50 degrees Celsius. Another example of stringent hybridization conditions are hybridization in 6× sodium chloride/sodium citrate (SSC) at about 45 degrees Celsius, followed by one or more washes in 0.2×SSC, 0.1% SDS at 55 degrees Celsius. A further example of stringent hybridization conditions is hybridization in 6× sodium chloride/sodium citrate (SSC) at about 45 degrees Celsius, followed by one or more washes in 0.2×SSC, 0.1% SDS at 60 degrees Celsius. Often, stringent hybridization conditions are hybridization in 6× sodium chloride/sodium citrate (SSC) at about 45 degrees Celsius, followed by one or more washes in 0.2×SSC, 0.1% SDS at 65 degrees Celsius. More often, stringency conditions are 0.5M sodium phosphate, 7% SDS at 65 degrees Celsius, followed by one or more washes at 0.2×SSC, 1% SDS at 65 degrees Celsius. Stringent hybridization temperatures can also be altered (i.e., lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a primer, to a nucleic acid molecule having a sequence complementary to the primer compared to hybridization to a nucleic acid molecule not having a complementary sequence. For example, specific hybridization includes the hybridization of a primer to a target nucleic acid sequence that is complementary to the primer.

In some embodiments primers can include a nucleotide subsequence that may be complementary to a solid phase nucleic acid primer hybridization sequence or substantially complementary to a solid phase nucleic acid primer hybridization sequence (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% identical to the primer hybridization sequence complement when aligned). A primer may contain a nucleotide subsequence not complementary to or not substantially complementary to a solid phase nucleic acid primer hybridization sequence (e.g., at the 3' or 5' end of the nucleotide subsequence in the primer complementary to or substantially complementary to the solid phase primer hybridization sequence).

A primer, in certain embodiments, may contain a modification such as inosines, abasic sites, locked nucleic acids, minor groove binders, duplex stabilizers (e.g., acridine, spermidine), Tm modifiers or any modifier that changes the binding properties of the primers or probes.

A primer, in certain embodiments, may contain a detectable molecule or entity (e.g., a fluorophore, radioisotope, colorimetric agent, particle, enzyme and the like). When desired, the nucleic acid can be modified to include a detectable label using any method known to one of skill in the art. The label may be incorporated as part of the synthesis, or added on prior to using the primer in any of the processes described herein. Incorporation of label may be performed either in liquid phase or on solid phase. In some embodiments the detectable label may be useful for detection of targets. In some embodiments the detectable label may be useful for the quantification target nucleic acids (e.g., determining copy number of a particular sequence or species of nucleic acid). Any detectable label suitable for detection of an interaction or biological activity in a system can be appropriately selected and utilized by the artisan. Examples of detectable labels are fluorescent labels such as fluorescein, rhodamine, and others (e.g., Anantha, et al., Biochemistry (1998) 37:2709 2714; and Qu & Chaires, Methods Enzymol. (2000) 321:353 369); radioactive isotopes (e.g., 125I, 131I, 35S, 31P, 32P, 33P, 14C, 3H, 7Be, 28Mg, 57Co, 65Zn, 67Cu, 68Ge, 82Sr, 83Rb, 95Tc, 96Tc, 103Pd, 109Cd, and 127Xe); light scattering labels (e.g., U.S. Pat. No. 6,214,560, and commercially available from Genicon Sciences Corporation, California); chemiluminescent labels and enzyme substrates (e.g., dioxetanes and acridinium esters), enzymic or protein labels (e.g., green fluorescence protein (GFP) or color variant thereof, luciferase, peroxidase); other chromogenic labels or dyes (e.g., cyanine), and other cofactors or biomolecules such as digoxigenin, strepdavidin, biotin (e.g., members of a binding pair such as biotin and avidin for example), affinity capture moieties and the like. In some embodiments a primer may be labeled with an affinity capture moiety. Also included in detectable labels are those labels useful for mass modification for detection with mass spectrometry (e.g., matrix-assisted laser desorption ionization (MALDI) mass spectrometry and electrospray (ES) mass spectrometry).

A primer also may refer to a polynucleotide sequence that hybridizes to a subsequence of a target nucleic acid or another primer and facilitates the detection of a primer, a target nucleic acid or both, as with molecular beacons, for example. The term "molecular beacon" as used herein refers to detectable molecule, where the detectable property of the molecule is detectable only under certain specific conditions, thereby enabling it to function as a specific and informative signal. Non-limiting examples of detectable properties are, optical properties, electrical properties, magnetic properties, chemical properties and time or speed through an opening of known size.

In some embodiments a molecular beacon can be a single-stranded oligonucleotide capable of forming a stem-loop structure, where the loop sequence may be complementary to a target nucleic acid sequence of interest and is flanked by short complementary arms that can form a stem. The oligonucleotide may be labeled at one end with a fluorophore and at the other end with a quencher molecule. In the stem-loop conformation, energy from the excited fluorophore is transferred to the quencher, through long-range dipole-dipole coupling similar to that seen in fluorescence resonance energy transfer, or FRET, and released as heat instead of light. When the loop sequence is hybridized to a specific target sequence, the two ends of the molecule are separated and the energy from the excited fluorophore is emitted as light, generating a detectable signal. Molecular beacons offer the added advantage that removal of excess probe is unnecessary due to the self-quenching nature of the unhybridized probe. In some embodiments molecular beacon probes can be designed to either discriminate or tolerate mismatches between the loop and target sequences by modulating the relative strengths of the loop-target hybridization and stem formation. As referred to herein, the term "mismatched nucleotide" or a "mismatch" refers to a nucleotide that is not complementary to the target sequence at that position or positions. A probe may have at least one mismatch, but can also have 2, 3, 4, 5, 6 or 7 or more mismatched nucleotides.

Biological Characteristics of Anti-Alpha Toxin Antibodies and Fragments

An antibody may have one or more characteristics identical to or similar to an antibody described herein, and often possesses one or more of the biological characteristics that distinguishes it from other antibodies that bind to the same antigen, alpha toxin. As used here, "biological characteristics" of an antibody refers to any one or more of biochemical, binding and functional characteristics, which can be used to select antibodies for therapeutic, research, and diagnostic uses. For example, anti-alpha toxin antibodies and fragments may be the same or different with respect to epitope binding, targeting, affinity, neutralizing, and inhibition of oligomerization or heptamer pore complex formation, for example.

Biochemical characteristics of an anti-alpha toxin antibody or fragment include, but are not limited to, isoelectric point (pI) and melting temperature (Tm). The binding characteristics of an anti-alpha toxin antibody or fragment include, but are not limited to, binding specificity; dissociation constant ($K_d$), or its inverse, association constant ($K_a$), or its component $k_{on}$ or $k_{off}$ rates; epitope to which it binds; ability to distinguish between various forms and/or preparations of alpha toxin (e.g., recombinant, native, acetylated) and ability to bind soluble and/or immobilized antigen. Functional characteristics of an antibody presented herein include, but are not limited to, inhibition of alpha toxin receptor binding, inhibition of alpha toxin oligomerization, inhibition of gene expression induced by cascade reactions responsive to alpha toxin expression or activity, depletion of cells expressing alpha toxin, growth inhibition of cells expressing alpha toxin, inhibition of the localization of alpha toxin, and protection in one or more *S. aureus*, alpha toxin or *S. aureus* and alpha toxin-related diseases or disorders. Described herein are characteristics of anti-alpha toxin antibodies and fragments and methods for modifying and fine tuning those characteristics. Methods for measuring characteristics of antibodies are known in the art, some of which are detailed hereafter.

Binding Characteristics

As described above, an anti-alpha toxin antibody or fragment immunospecifically bind at least one specified epitope or antigenic determinants of the protein, peptide, subunit, fragment, portion or any combination thereof exclusively or preferentially with respect to other polypeptides. The term "epitope" or "antigenic determinant" as used herein refers to a protein determinant capable of binding to an antibody, where the term "binding" herein often relates to a specific binding. These protein determinants or epitopes often include chemically active surface groupings of molecules such as amino acids or sugar side chains, often having specific three dimensional structural characteristics, and often having specific charge characteristics. Conformational and non-conformational epitopes are distinguished in that the binding to the former but not the latter is lost in the presence of denaturing solvents. The term "discontinuous epitope" as used herein, refers to a conformational epitope on a protein antigen formed from at least two separate regions in the primary sequence of the protein.

In certain embodiments, an anti-alpha toxin antibody or fragment immunospecifically binds to *Staphylococcus aureus* alpha toxin and antigenic fragments associated with alpha toxin oligomerization, thereof. In some embodiments, an anti-alpha toxin antibody or fragment immunospecifically binds to alpha toxin, or at least any three contiguous amino acids of SEQ ID NO: 39 or 40. In some embodiments, the epitope is at least 4 amino acid residues, at least 5 amino acid residues, at least 6 amino acid residues, at least 7 amino acid residues, at least 8 amino acid residues or at least 9 amino acid residues to the entire specified portion of contiguous amino acids of the alpha toxin protein. In certain embodiments, the contact residues comprise T261, T263, N264, K266 and K271. In other embodiments, the contact residues comprise N177, W179, G180, P181, Y182, D183, D185, S186, W187, N188, P189, V190, Y191 and R200 of SEQ ID NO: 39. In further embodiments, the contact residues comprises N177, W179, G180, P181, Y182, D183, D185, S186, W187, N188, P189, V190, Y191, R200, T261, T263, N264, K266 and K271 of SEQ ID NO: 39. In certain embodiments, the portion of the alpha toxin in contact with the antibody or antigen-binding fragment thereof comprises amino acids 261-272 of SEQ ID NO: 39. In other embodiments, the portion of the alpha toxin in contact with the antibody or antigen-binding fragment thereof comprises amino acids 248-277 of SEQ ID NO: 39. In other embodiments, the portion of the alpha toxin in contact with the antibody or antigen-binding fragment thereof comprises amino acids 173-201 and 261-272 of SEQ ID NO: 39.

In various embodiments, an anti-alpha toxin antibody or fragment associated with alpha toxin oligomerization thereof, immunospecifically binds an alpha toxin polypeptide or antigenic fragment thereof, having at least 60%, 65%, 70%, 75%, 80%, 85%, 90%, 95% identity, or 100% identity, to the amino acid sequence of SEQ ID NO: 39 or 40. An anti-alpha toxin antibody or fragment may sometimes immunospecifically binds to an alpha toxin polypeptide or antigenic fragment thereof, having at least 90%, 91%, 92%, 93%, 94%, 95%, 96%, 97%, 98%, 99% identity, or 100% identity, to the amino acid sequence of SEQ ID NO: 39 or 40.

In certain embodiments, an anti-alpha toxin antibody or fragment may bind an epitope conserved across species. In some embodiments, an anti-alpha toxin antibody or fragment binds *S. aureus* alpha toxin and alpha toxin homologs or orthologs from other bacterial species and antigenic fragments thereof. In some embodiments an anti-alpha toxin antibody or fragment may bind to one or more alpha toxin orthologs and or isoforms. In a specific embodiment, an anti-alpha toxin antibody or fragment binds to alpha toxin and antigenic fragments associated with alpha toxin oligomerization thereof from one or more species of bacteria possessing alpha toxin homologs or orthologs. In certain embodiments, anti-alpha toxin antibodies or fragments may bind an epitope within *Staphylococcus* or other closely related bacteria across alpha toxin homologs and/or isoforms and/or conformational variants and/or subtypes.

Interactions between antigens and antibodies often are the same as for other non-covalent protein-protein interactions. In general, four types of binding interactions exist between antigens and antibodies: (i) hydrogen bonds, (ii) dispersion forces, (iii) electrostatic forces between Lewis acids and Lewis bases, and (iv) hydrophobic interactions. Hydrophobic interactions are a significant driving force for antibody-antigen interactions, and are based on repulsion of water by non-polar groups rather than attraction of molecules. However, certain physical forces also contribute to antigen-antibody binding, for example, the fit or complimentary of epitope shapes with different antibody binding sites. Other materials and antigens may cross-react with an antibody, thereby competing for available free antibody.

Measurement of an affinity constant and specificity of binding between antigen and antibody often is an element in determining the efficacy of therapeutic, diagnostic and research methods using anti-alpha toxin antibodies and fragments. "Binding affinity" generally refers to the strength of the sum total of the noncovalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the equilibrium dissociation constant ($K_d$), which is calculated as the ratio koff/kon. Affinity can be measured by common methods known in the art, including those described and exemplified herein (e.g., BiaCore methods). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present technology.

An anti-alpha toxin antibody or fragment sometimes has a binding affinity for an alpha toxin epitope characterized by a dissociation constant ($K_d$) of $1\times10^{-2}$M or less, $1\times10^{-3}$M or less, $1\times10^{-4}$M or less, $1\times10^{-5}$M or less, $1\times10^{-6}$M or less, $1\times10^{-7}$M or less, $1\times10^{-8}$M or less, $1\times10^{-9}$M or less, $1\times10^{-10}$M or less, $1\times10^{-11}$M or less, $1\times10^{-12}$M or less, $1\times10^{-13}$M or less, $1\times10^{-14}$M or less or $1\times10^{-15}$M or less.

For example, the $K_d$ may be from $1\times10^{-15}$M to $1\times10^{-2}$M, from $1\times10^{-14}$M to $1\times10^{-10}$M, from $1\times10^{-9}$M to $1\times10^{-5}$M and from $1\times10^{-4}$M to $1\times10^{-2}$M.

In certain embodiments, an anti-alpha toxin antibodies and fragments is a high-affinity antibody. By "high-affinity antibody" is meant an antibody which binds to an alpha toxin epitope with an affinity less than $10^{-8}$M (e.g., $10^{-9}$M, $10^{-10}$M, and the like).

In certain embodiments, an anti-alpha toxin antibody or fragment is described as having a binding affinity of a specific molarity or better. "Or better" when used herein refers to a stronger binding, represented by a smaller numerical $K_d$ value. For example, an antibody which has an affinity for an antigen of "0.6 nM or better", the antibody's affinity for the antigen is <0.6 nM, i.e., 0.59 nM, 0.58 nM, 0.57 nM and the like, or any value less than 0.6 nM.

In some embodiments, the affinity of an anti-alpha toxin antibody or fragment is described in terms of the association constant ($K_a$), which is calculated as the ratio kon/koff. In this instance the present anti-alpha toxin antibodies and fragments have binding affinities for an alpha toxin epitope that include an association constant ($K_a$) of $1\times10^2 M^{-1}$ or more, $1\times10^3 M^{-1}$ or more, $1\times10 M^{-1}$ or more, $1\times10^5 M^{-1}$ or more, $1\times10^6 M^{-1}$ or more, $1\times10^7 M^{-1}$ or more, $1\times10^8 M^{-1}$ or more, $1\times10^9 M^{-1}$ or more, $1\times10^{10} M^{-1}$ or more $1\times10^{11} M^{-1}$ or more $1\times10^{12} M^{-1}$ or more, $1\times10^{13} M^{-1}$ or more, $1\times10^{14} M^{-1}$ or more or $1\times10^{15} M^{-1}$ or more. For example, the $K_a$ may be from $1\times10^2 M^{-1}$ to $1\times10^7 M^{-1}$, from $1\times10^7 M^{-1}$ to $1\times10^{10} M^{-1}$, and from $1\times10^{10} M^{-1}$ to $1\times10^{10} M^{-1}$.

In certain embodiments the rate at which an anti-alpha toxin antibody or fragment dissociates from an alpha toxin epitope may be relevant. In some embodiments, an anti-alpha toxin antibody or fragment can bind to alpha toxin with a $k_{off}$ of less than $10^{-3}$ s$^{-1}$, less than $5\times10^{-3}$ s$^{-1}$, less than $10^{-4}$ s$^{-1}$, less than $5\times10^{-4}$ s$^{-1}$, or less than $10^{-5}$ s$^{-1}$. In some embodiments the rate at which the anti-alpha toxin antibodies and fragments associate with an alpha toxin epitope may be more relevant than the value of the $K_d$ or the $K_a$. In this instance the present anti-alpha toxin antibodies and fragments bind to alpha toxin with a $k_{on}$ rate of at least $10^{-4}$ M$^{-1}$ s$^{-1}$, at least $5\times10^{-4}$ M$^{-1}$ s$^{-1}$, at least $10^5$ M$^{-1}$ s$^{-1}$, at least $5\times10^5$ M$^{-1}$ s$^{-1}$, at least $10^6$ M$^{-1}$ s$^{-1}$, at least $5\times10^6$ M$^{-1}$ s$^{-1}$, at least $10^7$ M$^{-1}$ s$^{-1}$.

Determination of binding affinity can be measured using the specific techniques described further in the Example section, see Example 1, and methods known in the art. One example of such a method includes measuring the disassociation constant "$K_d$" by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate. To establish conditions for the assay, microtiter plates (Dynex) are coated overnight with 5 µg/ml of a capturing anti-Fab antibody (Cappel Labs) in 50 mM sodium carbonate (H 9.6), and subsequently blocked with 2% (w/v) bovine serum albumin in PBS for two to five hours at room temperature (approximately 23 degrees Celsius). In a non-adsorbent plate (Nunc #269620), 100 pM or 26 pM [125I]-antigen are mixed with serial dilutions of a Fab of interest. The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 µl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays.

In another instance the $K_d$ value may be measured by using surface plasmon resonance assays, which can be carried out, for example, using a BIAcore™-2000 or a BIAcore™-3000 (BIAcore, Inc., Piscataway, N.J.) at 25 degrees Celsius with immobilized antigen CM5 chips at ~10 response units (RU). Briefly, in an example of such a method, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 110 mM sodium acetate, pH 4.8, into 5 µg/microliter (~0.2 uM) before injection at a flow rate of 5 µl/minute to achieve approximately 10 response units (RU) of coupled protein. Following the injection of antigen, IM ethanolamine is injected to block unreacted groups. For kinetics measurements, two-fold serial dilutions of Fab (0.78 nM to 500 nM) are injected in PBS with 0.05% Tween 20 (PBST) at 25 degrees Celsius at a flow rate of approximately 25 µl/min. Association rates (kon) and dissociation rates (koff) are calculated using a simple one-to-one Langmuir binding model (BIAcore Evaluation Software version 3.2) by simultaneously fitting the association and dissociation sensorgram.

If the on-rate exceeds $10^6$ M-1 s-1 by the surface plasmon resonance assay above, then the on-rate can be determined by using a fluorescent quenching technique, for example, that measures the increase or decrease in fluorescence emission intensity (excitation=295 nm; emission=340 nm, 16 nm band-pass) at 25 degrees Celsius of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette. An "on-rate" or "rate of association" or "association rate" or "kon" according to this technology can also be determined with the same surface plasmon resonance technique described above using a BIAcore™-2000 or a BIAcore™-3000 (BIAcore, Inc., Piscataway, N.J.) as described above.

Methods and reagents suitable for determination of binding characteristics of an isolated antibody or antigen-binding fragment thereof presented, or an altered/mutant derivative thereof (discussed below), are known in the art and/or are commercially available. Equipment and software designed for such kinetic analyses are commercially available (e.g., Biacore® A100, and Biacore® 2000 instruments; Biacore International AB, Uppsala, Sweden).

In some embodiments, a binding assay may be performed as direct binding assays or as competition-binding assays. Binding can be detected using standard ELISA or standard Flow Cytometry assays. In a direct binding assay, a candidate antibody is tested for binding to alpha toxin antigen. Competition-binding assay, on the other hand, assess the ability of a candidate antibody to compete with a known anti-alpha toxin antibody or fragment or other compound that binds alpha toxin (e.g., receptor, inhibitor). In general any method that permits the binding of an antibody with alpha toxin that can be detected is encompassed with the scope of the present technology for detecting and measuring the binding characteristics of the antibodies. These methods also can be utilized to screen a panel of antibodies for those providing a desired characteristic.

In certain embodiments an isolated antibody or antigen-binding fragment thereof immunospecifically binds to alpha toxin and has one or more of the characteristics selected from the group consisting of:
(a) affinity constant ($K_D$) for alpha toxin of about 13 nM or less;
(b) binds to alpha toxin monomers, but does not inhibit binding of alpha toxin to alpha toxin receptor;
(c) inhibits the formation of alpha toxin oligomers by at least 50%, 60%, 70%, 80%, 90% or 95%;
(d) reduces alpha toxin cytolytic activity by at least 50%, 60%, 70%, 80%, 90% or 95% (e.g., as determined by cell lysis add hemolysis assays);
(e) reduces cell infiltration and pro-inflammatory cytokine release (e.g., in animal pneumonia model).

In some embodiments an isolated antibody or antigen-binding fragment thereof binds an antigen (e.g., alpha toxin) with an affinity characterized by a disassociation constant ($K_D$) in the range of about 0.01 nM to about 50 nM, 0.05 nM, 0.1 nM, 0.5 nM, 1 nN, 5 nM, 10 nM, 20 nM, 30 nM, or 40 nM.

Functional Characteristics

In certain embodiments, an anti-alpha toxin antibody or fragment alters the biological properties of alpha toxin and/or alpha toxin expressing cells. In some embodiments, an anti-alpha toxin antibody or fragment neutralizes the biological activity of alpha toxin by binding to the polypeptide and inhibiting the assembly of alpha toxin monomers into a transmembrane pore (e.g., alpha toxin heptamer). Neutralization assays can be performed using methods known in the art using, in some circumstances, commercially available reagents. Neutralization of alpha toxin often is measured with an IC50 of $1 \times 10^{-6}$ M or less, $1 \times 10^{-7}$ M or less, $1 \times 10^{-8}$ M or less, $1 \times 10^{-9}$ M or less, $1 \times 10^{-10}$ M or less and $1 \times 10^{-11}$ M or less. In certain embodiments, neutralization occurs when the antibody or antigen binding fragment that immunospecifically binds to *S. aureus* alph toxin is at a concentration as described in Examples 3-6. In certain embodiments, an anti-alpha toxin antibody or fragment neutralizes the ability of alpha toxin to oligomerize and form a transmembrane pore. The term "inhibitory concentration 50%" (abbreviated as "IC50") represents the concentration of an inhibitor (e.g., an anti-alpha toxin antibody or fragment provided herein) that is required for 50% inhibition of a given activity of the molecule the inhibitor targets (e.g., alpha toxin oligomerization to form a transmembrane pore heptamer complex). A lower IC50 value generally corresponds to a more potent inhibitor.

In certain embodiments, an anti-alpha toxin antibody or fragment inhibits one or more biological activities of alpha toxin. The term "inhibition" as used herein, refers to any statistically significant decrease in biological activity, including full blocking of the activity. For example, "inhibition" can refer to a decrease of about 10%, 20%, 30%, 40%, 50%, 60%, 70%, 80%, 90%, or 100% in biological activity. In certain embodiments, an anti-alpha toxin antibody or fragment inhibits one or more biological activities of alpha toxin by at least 10%, 20%, 30%, 40%, 50%, 60%, 70%, 80%, 90%, or 100%.

In some embodiments, an anti-alpha toxin antibody or fragment may deplete alpha toxin secreted by pathogenic *S. aureus*. In some embodiments, an anti-alpha toxin antibody or fragment may achieve at least about 20%, at least about 30%, at least about 40%, at least about 50%, at least about 60%, at least about 70%, at least about 80%, at least about 90%, at least about 95%, or about 100% depletion of alpha toxin secreted by *S. aureus*. In particular embodiments, virtually all detectable secreted alpha toxin is depleted from cells infected with *S. aureus*.

In certain embodiments, an anti-alpha toxin antibody or fragment may inhibit in vitro stimulated alpha toxin activity (e.g., receptor binding, oligomerization) and/or proliferation of cells expressing or secreting alpha toxin. An anti-alpha toxin antibody or fragment sometimes inhibits in vitro alpha toxin activity, *S. aureus* pathogenicity by at least about 10%, at least about 20%, at least about 30%, at least about 40%, at least about 50% or at least about 75%. Methods for measuring cell proliferation, pathogenicity, and alpha hemolysin activity are known in the art.

In certain embodiments, an anti-alpha toxin antibody or fragment may inhibit the expression of one or more inducible genes that responds directly or indirectly to the environment created by *S. aureus* infection and/or alpha toxin expression and function. In specific embodiments, an anti-alpha toxin antibody or fragment inhibits the expression of one or more inducible genes that responds directly or indirectly to the environment created by *S. aureus* infection and/or alpha toxin expression and function by at least 20%, by at least 30%, by at least 40%, by at least 50%, by at least 60%, by at least 70%, by at least 80%, by at least 90%, by at least 100%, by at least 120%, by at least 140%, by at least 160%, by at least 180%, or by at least 200%.

Production of Anti-Alpha Toxin Antibodies and Fragments

The following describes exemplary techniques for the production of antibodies. An alpha toxin antigen used for production of antibodies may be a peptide fragment that, for example, includes a region of the alpha toxin peptide sequence involved in oligomerization. Antibodies against alpha toxin can be generated using native *S. aureus* alpha toxin comprising SEQ ID NO: 39, or mutant alpha toxin comprising SEQ ID NO: 40, a variant, or an antigenic fragment thereof. *S. aureus* cells expressing and secreting alpha toxin can also be used to generate antibodies. Examples of nucleotide and amino acid sequences of alpha toxin are available as provided in Table 10 for example. Alpha toxin can be produced recombinantly in an isolated form from bacterial or eukaryotic cells using standard recombinant DNA methodology. Alpha toxin can be expressed as a tagged (e.g., epitope tag) or other fusion protein (e.g., GST fusion) to facilitate isolation as well as identification in various assays. Antibodies or binding proteins that bind to various tags and fusion sequences are available as elaborated below. Other forms of alpha toxin useful for generating antibodies also can be used.

Various tag polypeptides and their respective antibodies are known in the art. Examples include poly-histidine (poly-his) or poly-histidine-glycine (poly-his-gly) tags; flu HA tag polypeptide and its antibody 12CA5; c-myc tag and 8F9, 3C7, 6E10, G4, B7 and 9E10 antibodies thereto; and Herpes Simplex virus glycoprotein D (gD) tag and its antibody. The FLAG-peptide is recognized by an anti-FLAG M2 monoclonal antibody. Purification of a protein containing the FLAG peptide can be performed by immunoaffinity chromatography using an affinity matrix comprising the anti-FLAG M2 monoclonal antibody covalently attached to agarose. Other tag polypeptides include the KT3 epitope peptide; an α-tubulin epitope peptide; and the T7 gene 10 protein peptide tag.

Polyclonal antibodies to an antigen-of-interest can be produced by various procedures known in the art. For example, an alpha toxin polypeptide or immunogenic fragment thereof can be administered to various host animals including, but not limited to, rabbits, mice, rats, and the like, to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also known in the art.

Polyclonal antibodies can be raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent (reactive group), e.g., activated ester (conjugation through cysteine or lysine residues), glutaraldehyde, succinic anhydride, SOCl2, or R1N=C=NR, where R and R1 are different alkyl groups. Conjugates also can be made in recombinant cell culture as fusion proteins.

Typically animals are immunized against the antigen, immunogenic conjugates, or derivatives by combining an appropriate concentration of antigen or conjugate with adjuvant and injecting the solution at multiple sites. Immunizations can also be performed as described in Example 1 (immunization/hybridoma generation).

Monoclonal antibodies can be prepared using a wide variety of techniques known in the art including the use of hybridoma, recombinant, and phage display technologies, or a combination thereof. The term "monoclonal antibody" as used herein refers to an antibody obtained from a population of substantially homogeneous or isolated antibodies, e.g., the individual antibodies comprising the population are identical except for possible naturally occurring mutations that may be present in minor amounts. Monoclonal antibodies are highly specific, being directed against a single antigenic site or multiple antigenic sites in the case of multispecific engineered antibodies. Furthermore, in contrast to polyclonal antibody preparations which include different antibodies directed against different determinants (epitopes), each monoclonal antibody is directed against the same determinant on the antigen. In addition to their specificity, the monoclonal antibodies are advantageous in that they may be synthesized uncontaminated by other antibodies. The modifier "monoclonal" is not to be construed as requiring production of the antibody by any particular method. Following is a description of representative methods for producing monoclonal antibodies which is not intended to be limiting and may be used to produce, for example, monoclonal mammalian, chimeric, humanized, human, domain, diabodies, vaccibodies, linear and multispecific antibodies.

Methods for producing and screening for specific antibodies using hybridoma technology are routine and known in the art. In the hybridoma method, mice or other appropriate host animals, such as hamster, are immunized as described above to elicit lymphocytes that produce or are capable of producing antibodies that will specifically bind to the antigen used for immunization. Alternatively, lymphocytes may be immunized in vitro. After immunization, lymphocytes are isolated and then fused with a myeloma cell line using a suitable fusing agent or fusion partner, such as polyethylene glycol, to form a hybridoma cell. In certain embodiments, the selected myeloma cells are those that fuse efficiently, support stable high-level production of antibody by the selected antibody-producing cells, and are sensitive to a selective medium that selects against the unfused parental cells. In one aspect, the myeloma cell lines are murine myeloma lines, such as those derived from MOPC-21 and MPC-11 mouse tumors available from the Salk Institute Cell Distribution Center, San Diego, Calif., USA, and SP-2 and derivatives e.g., X63-Ag8-653 cells available from the American Type Culture Collection, Rockville, Md., USA. Human myeloma and mouse-human heteromyeloma cell lines also have been described for the production of human monoclonal antibodies.

Once hybridoma cells that produce antibodies of the desired specificity, affinity, and/or activity are identified, the clones may be subcloned by limiting dilution procedures and grown by standard methods. Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, affinity tags, hydroxylapatite chromatography, gel electrophoresis, dialysis, and the like. Exemplary purification methods are described in more detail below.

Recombinant DNA Techniques

Methods for producing and screening for specific antibodies using recombinant DNA technology are routine and known in the art. DNA encoding monoclonal antibodies may be readily isolated and/or sequenced using conventional procedures (e.g., by using oligonucleotide probes that are capable of binding specifically to genes encoding the heavy and light chains of murine antibodies). Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. As described below for antibodies generated by phage display and humanization of antibodies, DNA or genetic material for recombinant antibodies can be obtained from source(s) other than hybridomas to generate an anti-alpha toxin antibody or fragment.

Recombinant expression of an antibody or variant thereof often requires construction of an expression vector containing a polynucleotide that encodes the antibody. Herein provided are replicable vectors comprising a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule and the variable domain of the antibody may be cloned into such a vector for expression of the entire heavy, the entire light chain, or both the entire heavy and light chains.

Once an expression vector is transferred to a host cell by conventional techniques, the transfected cells then are cultured by conventional techniques to produce an antibody. Thus, provided herein are host cells containing a polynucleotide encoding an isolated antibody or antigen-binding fragment thereof presented or fragments thereof, or a heavy or light chain thereof, or portion thereof, or a single-chain antibody herein, operably linked to a heterologous promoter. In certain embodiments for the expression of double-chained antibodies, vectors encoding both the heavy and light chains may be co-expressed in the host cell for expression of the entire immunoglobulin molecule, as detailed below.

Mammalian cell lines available as hosts for expression of recombinant antibodies are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. In certain embodiments, human cell lines developed by immortalizing human lymphocytes can be used to recombinantly produce monoclonal antibodies. In some embodiments, the human cell line PER.C6. (Crucell, Netherlands) can be used to recombinantly produce monoclonal antibodies.

Additional cell lines that may be used as hosts for expression of recombinant antibodies include, but are not limited to, insect cells (e.g., Sf21/Sf9, Trichoplusia ni Bti-Tn5b1-4) or yeast cells (e.g., S. cerevisiae, Pichia, U.S. Pat. No. 7,326,681; etc), plants cells (US20080066200); and chicken cells.

In certain embodiments, antibodies presented herein are expressed in a cell line with stable expression of the antibody. Stable expression can be used for long-term, high-yield production of recombinant proteins. For example, cell lines which stably express the antibody molecule may be generated. Host cells can be transformed with an appropriately engineered vector comprising expression control elements (e.g., promoter, enhancer, transcription terminators, polyadenylation sites, and the like), and a selectable marker gene. Following the introduction of the foreign DNA, cells may be allowed to grow for 1-2 days in an enriched media, and then are switched to a selective media. The selectable marker in the recombinant plasmid confers resistance to the selection and allows cells that stably integrated the plasmid into their chromosomes to grow and form foci which in turn can be cloned and expanded into cell lines. Methods for producing stable cell lines with a high yield are known in the art and reagents are generally available commercially.

In certain embodiments, antibodies presented herein are expressed in a cell line with transient expression of the antibody. Transient transfection is a process in which the nucleic acid introduced into a cell does not integrate into the genome or chromosomal DNA of that cell. A nucleic acid often is maintained as an extrachromosomal element, e.g., as an episome, in the cell. Transcription processes of the nucleic acid of the episome are not affected and a protein encoded by the nucleic acid of the episome is produced.

The cell line, which can be stable or transiently transfected, is maintained in cell culture medium and conditions known in the art resulting in expression and production of monoclonal antibodies. In certain embodiments, the mammalian cell culture media is based on commercially available media formulations, including, for example, DMEM or Ham's F12. In some embodiments, the cell culture media is modified to support increases in both cell growth and biologic protein expression. As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium may be optimized for a specific cell culture use, including, for example, cell culture growth medium which is formulated to promote cellular growth, or cell culture production medium which is formulated to promote recombinant protein production. The terms nutrient, ingredient, and component are used interchangeably herein to refer to the constituents that make up a cell culture medium.

In various embodiments, the cell lines are maintained using a fed batch method. As used herein, "fed batch method," refers to a method by which a fed batch cell culture is supplied with additional nutrients after first being incubated with a basal medium. For example, a fed batch method may comprise adding supplemental media according to a determined feeding schedule within a given time period. Thus, a "fed batch cell culture" refers to a cell culture where the cells, typically mammalian, and culture medium are supplied to the culturing vessel initially and additional culture nutrients are fed, continuously or in discrete increments, to the culture during culturing, with or without periodic cell and/or product harvest before termination of culture.

The cell culture medium used and the nutrients contained therein are known in the art. In some embodiments, the cell culture medium comprises a basal medium and at least one hydrolysate, e.g., soy-based, hydrolysate, a yeast-based hydrolysate, or a combination of the two types of hydrolysates resulting in a modified basal medium. The additional nutrients may sometimes include only a basal medium, such as a concentrated basal medium, or may include only hydrolysates, or concentrated hydrolysates. Suitable basal media include, but are not limited to Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (see, e.g., CHO protein free medium (Sigma) or EX-CELL™ 325 PF CHO Serum-Free Medium for CHO Cells Protein-Free (SAFC Bioscience), and Iscove's Modified Dulbecco's Medium. Other examples of basal media which may be used in the technology herein include BME Basal Medium; Dulbecco's Modified Eagle Medium (DMEM, powder) (Gibco-Invitrogen (#31600). In certain embodiments, the basal medium may be is serum-free, meaning that the medium contains no serum (e.g., fetal bovine serum (FBS), horse serum, goat serum, or any other animal-derived serum known in the art) or animal protein free media or chemically defined media.

The basal medium may be modified in order to remove certain non-nutritional components found in standard basal medium, such as various inorganic and organic buffers, surfactant(s), and sodium chloride. Removing such components from basal cell medium allows an increased concentration of the remaining nutritional components, and may improve overall cell growth and protein expression. In addition, omitted components may be added back into the cell culture medium containing the modified basal cell medium according to the requirements of the cell culture conditions. In certain embodiments, the cell culture medium contains a modified basal cell medium, and at least one of the following nutrients, an iron source, a recombinant growth factor; a buffer; a surfactant; an osmolarity regulator; an energy source; and non-animal hydrolysates. In addition, the modified basal cell medium may optionally contain amino acids, vitamins, or a combination of both amino acids and vitamins. In some embodiments, the modified basal medium further contains glutamine, e.g., L-glutamine, and/or methotrexate.

In some embodiments, antibody production is conducted in large quantity by a bioreactor process using fed-batch, batch, perfusion or continuous feed bioreactor methods known in the art. Large-scale bioreactors have at least 1000 liters of capacity, sometimes about 1,000 to 100,000 liters of capacity. These bioreactors may use agitator impellers to distribute oxygen and nutrients. Small scale bioreactors refers generally to cell culturing in no more than approximately 100 liters in volumetric capacity, and can range from about 1 liter to about 100 liters. Alternatively, single-use bioreactors (SUB) may be used for either large-scale or small scale culturing.

Temperature, pH, agitation, aeration and inoculum density may vary depending upon the host cells used and the recombinant protein to be expressed. For example, a recombinant protein cell culture may be maintained at a temperature between 30 and 45 degrees Celsius. The pH of the culture medium may be monitored during the culture process such that the pH stays at an optimum level, which may be for certain host cells, within a pH range of 6.0 to 8.0. An impellor driven mixing may be used for such culture methods for agitation. The rotational speed of the impellor may be approximately 50 to 200 cm/sec tip speed, but other airlift or other mixing/aeration systems known in the art may be used, depending on the type of host cell being cultured. Sufficient aeration is provided to maintain a dissolved oxygen concentration of approximately 20% to 80% air saturation in the culture, again, depending upon the selected host cell being cultured. Alternatively, a bioreactor may sparge air or oxygen directly into the culture medium. Other methods of oxygen supply exist, including bubble-free aeration systems employing hollow fiber membrane aerators.

Phage Display Techniques

In some embodiments, monoclonal antibodies or antibody fragments can be isolated from antibody phage libraries generated using techniques as known in the art. In such methods an anti-alpha toxin antibody or fragment can be isolated by screening of a recombinant combinatorial antibody library, sometimes a scFv phage display library, prepared using human VL and VH cDNAs prepared from mRNA derived from human lymphocytes. Methodologies for preparing and screening such libraries are known in the art.

Antibody Purification and Isolation

Once an antibody molecule has been produced by recombinant or hybridoma expression, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies of the present technology or fragments thereof may be fused to heterologous polypeptide sequences (referred to herein as "tags") described above or otherwise known in the art to facilitate purification.

Humanized Antibodies

In certain embodiments, the antibodies of the present technology are humanized antibodies, which are generated using methods known in the art. Humanized antibodies can be chimeric antibodies. Chimeric antibodies are antibodies in which a portion of the heavy and/or light chain is identical with or homologous to corresponding sequences in antibodies derived from a particular species or belonging to a particular antibody class or subclass, while another portion of the chain(s) is identical with or homologous to corresponding sequences in antibodies derived from another species or belonging to another antibody class or subclass, as well as fragments of such antibodies, so long as they exhibit the desired biological activity. Chimeric antibodies of interest herein include "primatized" antibodies comprising variable domain antigen-binding sequences derived from a nonhuman primate (e.g., Old World Monkey, such as baboon, rhesus or cynomolgus monkey) and human constant region sequences.

Human Antibodies

As an alternative to humanization, human antibodies can be generated using methods known in the art. Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. In practice, the use of XenoMouse® strains of mice that have been engineered to contain up to but less than 1000 kb-sized germline configured fragments of the human heavy chain locus and kappa light chain locus. The XenoMouse® strains are available from Amgen, Inc. (Fremont, Calif.).

The production of the XenoMouse® strains of mice and antibodies produced in those mice is known in the art. Essentially, XenoMouse® lines of mice are immunized with an antigen of interest (e.g., alpha toxin), lymphatic cells (such as B-cells) are recovered from the hyper-immunized mice, and the recovered lymphocytes are fused with a myeloid-type cell line to prepare immortal hybridoma cell lines using techniques described above an known in the art. These hybridoma cell lines are screened and selected to identify hybridoma cell lines that produced antibodies specific to the antigen of interest.

In an alternative approach, the minilocus approach, an exogenous Ig locus is mimicked through the inclusion of pieces (individual genes) from the Ig locus. Thus, one or more VH genes, one or more DH genes, one or more JH genes, a mu constant region, and usually a second constant region (e.g., a gamma constant region) are formed into a construct for insertion into an animal.

The generation of human antibodies from mice in which, through microcell fusion, large pieces of chromosomes, or entire chromosomes, have been introduced is known in the art. Additionally, KM™-mice, which are the result of crossbreeding of Kirin's Tc mice with Medarex's minilocus (Humab) mice have been generated. These mice possess the human IgH transchromosome of the Kirin mice and the kappa chain transgene of the Genpharm mice.

Human antibodies can also be derived by in vitro methods. Suitable examples include but are not limited to phage display (MedImmune (formerly CAT), Morphosys, Dyax, Biosite/Medarex, Xoma, Symphogen, Alexion (formerly Proliferon), Affimed) ribosome display (MedImmune (formerly CAT)), yeast display, and the like. The phage display technology can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats. Several sources of V-gene segments can be used for phage display. A diverse array of anti-oxazolone antibodies have been isolated from a small random combinatorial library of V genes derived from the spleens of immunized mice. A repertoire of V genes from unimmunized human donors can be constructed and antibodies to a diverse array of antigens (including self-antigens) can be isolated essentially following the techniques known in the art. As discussed above, human antibodies may also be generated by in vitro activated B cells.

Immunoglobulin genes undergo various modifications during maturation of the immune response, including recombination between V, D and J gene segments, isotype switching, and hypermutation in the variable regions. Recombination and somatic hypermutation are the foundation for generation of antibody diversity and affinity maturation, but they can also generate sequence liabilities that may make commercial production of such immunoglobulins as therapeutic agents difficult or increase the immunogenicity risk of the antibody. In general, mutations in CDR regions are likely to contribute to improved affinity and function, while mutations in framework regions may increase the risk of immunogenicity. This risk can be reduced by reverting framework mutations to germline while ensuring that activity of the antibody is not adversely impacted. The diversification processes may also generate some structural liabilities or these structural liabilities may exist within germline sequences contributing to the heavy and light chain variable domains. Regardless of the source, it may be desirable to remove potential structural liabilities that may result in instability, aggregation, heterogeneity of product, or increased immunogenicity. Examples of undesirable liabilities include unpaired cysteines (which may lead to disulfide bond scrambling, or variable sulfhydryl adduct formation), N-linked glycosylation sites (resulting in heterogeneity of structure and activity), as well as deamidation (e.g., NG, NS), isomerization (DG), oxidation (exposed methionine), and hydrolysis (DP) sites.

Accordingly, in order to reduce the risk of immunogenicity and improve pharmaceutical properties of the antibodies disclosed in Example 11, Tables 1-8 it may be desirable to revert a framework sequence to germline, revert a CDR to germline, and/or remove a structural liability. Thus, in some embodiments, where a particular antibody differs from its respective germline sequence at the amino acid level, the antibody sequence can be mutated back to the germline sequence. Such corrective mutations can occur at one, two, three or more positions, or a combination of any of the mutated positions, using standard molecular biological techniques.

Additional approaches include the Velocimmune® technology (Regeneron Pharmaceuticals). The Velocimmune® technology can be used to generate fully human monoclonal antibodies to targets of therapeutic interest and involves the generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody. See, e.g., U.S. Pat. No. 6,596,541.

Antibody Fragments

In certain embodiments, the present antibodies are antibody fragments or antibodies comprising these fragments. The antibody fragment comprises a portion of the full length antibody, which generally is the antigen binding or variable region thereof. Examples of antibody fragments include Fab, Fab', F(ab')2, Fd and Fv fragments. Diabodies; linear antibodies, single-chain antibody molecules; and multispecific antibodies are antibodies formed from these antibody fragments.

Traditionally, these fragments were derived via proteolytic digestion of intact antibodies using techniques known in the art. However, these fragments can now be produced directly by recombinant host cells. Fab, Fv and scFv antibody fragments can all be expressed in and secreted from E. coli, thus allowing the facile production of large amounts of these fragments. In some embodiments, the antibody fragments can be isolated from the antibody phage libraries discussed above. Alternatively, Fab'-SH fragments can also be directly recovered from E. coli and chemically coupled to form F(ab')2 fragments. According to another approach, F(ab')2 fragments can be isolated directly from recombinant host cell culture. Other techniques for the production of antibody fragments are known. In some embodiments, the antibody of choice is a single-chain Fv fragment (scFv). In certain embodiments, the antibody is not a Fab fragment. Fv and scFv are the only species with intact combining sites that are devoid of constant regions; thus, they are suitable for reduced nonspecific binding during in vivo use. scFv fusion proteins may be constructed to yield fusion of an effector protein at either the amino or the carboxy terminus of an scFv.

In certain embodiments, the present antibodies are domain antibodies, e.g., antibodies containing the small functional binding units of antibodies, corresponding to the variable regions of the heavy (VH) or light (VL) chains of human antibodies. Examples of domain antibodies include, but are not limited to, those available from Domantis that are specific to therapeutic targets. Commercially available libraries of domain antibodies can be used to identify anti-alpha toxin domain antibodies. In certain embodiments, anti-alpha toxin antibodies and fragments comprise a alpha toxin functional binding unit and an Fc gamma receptor functional binding unit.

In certain embodiments herein, the present antibodies are linear antibodies. Linear antibodies comprise a pair of tandem Fd segments (VH-CH1-VH-CH1) which form a pair of antigen-binding regions. Linear antibodies can be bispecific or monospecific.

Certain Amino Acid Sequence Modifications

In addition to the above described human, humanized and/or chimeric antibodies, the present technology also encompasses further modifications and, their variants and fragments thereof, of an anti-alpha toxin antibody or fragment comprising one or more of the following: amino acid residue and/or polypeptide substitution, addition and/or deletion in the variable light (VL) domain and/or variable heavy (VH) domain and/or Fc region, and a post translational modification. Included in these modifications are antibody conjugates where an antibody has been covalently attached to a moiety. Moieties suitable for attachment to the antibodies include but are not limited to, proteins, peptides, drugs, labels, and cytotoxins. These changes to the antibodies may be made to alter or fine tune characteristics (e.g., biochemical, binding and/or functional) of the antibodies as is appropriate for treatment and/or diagnosis of S. aureus associate and/or alpha toxin mediated diseases. Methods for forming conjugates, making amino acid and/or polypeptide changes and post-translational modifications are known in the art, some of which are detailed below. Any combination of deletion, insertion, and substitution can be made to arrive at a final construct, provided that the final construct possesses desired characteristics.

Amino acid changes to antibodies results in sequences that are less than 100% identical to an antibody sequence or parent antibody sequence described herein. In certain embodiments, in this context, the antibodies may have about 25% to about 95% sequence identity to the amino acid sequence of the heavy or light chain variable domain of an anti-alpha toxin antibody or fragment as described herein. Thus, in some embodiments a modified antibody may have an amino acid sequence having at least 2%, 3%, 4%, 55%, 65%, 75%, 80%, 85%, 90%, or 95% A amino acid sequence identity or similarity with the amino acid sequence of either the heavy or light chain variable domain of an anti-alpha toxin antibody or fragment as described herein. In certain embodiments, an altered antibody has an amino acid sequence having at least 25%, 35%, 45%, 55%, 65%, 75%, 80%, 85%, 90%, or 95% amino acid sequence identity or similarity with the amino acid sequence of the heavy or light chain CDR1, CDR2, or CDR3 of an anti-alpha toxin antibody or fragment as described herein. An altered antibody may sometimes have an amino acid sequence having at least 2%, 3%, 4%, 55%, 65%, 75%, 80%, 85%, 90%, or 95% A amino acid sequence identity or similarity with the amino acid sequence of the heavy or light chain FR1, FR2, FR3 or FR4 of an anti-alpha toxin antibody or fragment as described herein.

In certain embodiments, altered antibodies are generated by one or more amino acid alterations (e.g., substitutions, deletion and/or additions) introduced in one or more of the variable regions of the antibody. In various embodiments, the amino acid alterations are introduced in the framework regions. One or more alterations of framework region residues may result in an improvement in the binding affinity of the antibody for the antigen. This may be especially true when these changes are made to humanized antibodies where the framework region may be from a different species than the CDR regions. Examples of framework region residues to modify include those which non-covalently bind antigen directly, interact with/effect the conformation of a CDR, and/or participate in the VL-VH interface. In some embodiments, from about one to about five framework residues may be altered. Sometimes, this may be sufficient to yield an antibody mutant suitable for use in preclinical trials, even where none of the hypervariable region residues have been altered. Normally, however, an altered antibody will comprise additional hypervariable region alteration(s). In certain embodiments, the hypervariable region residues may be changed randomly, especially where the starting binding affinity of an anti-alpha toxin antibody or fragment for the antigen from the second mammalian species is such that such randomly produced antibodies can be readily screened.

One useful procedure for generating altered antibodies is called "alanine scanning mutagenesis". In this method, one or more of the hypervariable region residue(s) are replaced by alanine or polyalanine residue(s) to alter the interaction of the amino acids with alpha toxin. Those hypervariable region residue(s) demonstrating functional sensitivity to the substitutions then are refined by introducing additional or other mutations at or for the sites of substitution. Thus, while the site for introducing an amino acid sequence variation is predetermined, the nature of the mutation per se need not be predetermined. The Ala-mutants produced this way are screened for their biological activity as described herein.

In certain embodiments the substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage. Briefly, several hypervariable region sites (e.g., 6-7 sites) are mutated to generate all possible amino acid substitutions at each site. The antibody mutants thus generated are displayed in a monovalent fashion from filamentous phage particles as fusions to the gene III product of M13 packaged within each particle. The phage-displayed mutants are then screened for their biological activity (e.g., binding affinity) as herein disclosed.

Mutations in antibody sequences may include substitutions, deletions, including internal deletions, additions, including additions yielding fusion proteins, or conservative substitutions of amino acid residues within and/or adjacent to the amino acid sequence, but that result in a "silent" change, in that the change produces a functionally equivalent anti-alpha toxin antibody or fragment. Conservative amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In addition, glycine and proline are residues that can influence chain orientation. Non-conservative substitutions will entail exchanging a member of one of these classes for a member of another class. Furthermore, if desired, non-classical amino acids or chemical amino acid analogs can be introduced as a substitution or addition into the antibody sequence. Non-classical amino acids include, but are not limited to, the D-isomers of the common amino acids, alpha-amino isobutyric acid, 4-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, beta-alanine, fluoro-amino acids, designer amino acids such as beta-methyl amino acids, C-alpha-methyl amino acids, N-alpha-methyl amino acids, and amino acid analogs in general.

In certain embodiments any cysteine residue not involved in maintaining the proper conformation of an anti-alpha toxin antibody or fragment also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

In some embodiments, an antibody can be modified to produce fusion proteins; i.e., the antibody, or a fragment thereof, fused to a heterologous protein, polypeptide or peptide. In various embodiments, the protein fused to the portion of an antibody is an enzyme component of Antibody-Directed Enzyme Prodrug Therapy (ADEPT). Examples of other proteins or polypeptides that can be engineered as a fusion protein with an antibody include, but are not limited to toxins such as ricin, abrin, ribonuclease, DNase I, Staphylococcal enterotoxin-A, pokeweed anti-viral protein, gelonin, diphtheria toxin, *Pseudomonas* exotoxin, and *Pseudomonas* endotoxin. Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes.

Additional fusion proteins may be generated through known techniques of gene-shuffling, motif-shuffling, exon-shuffling, and/or codon-shuffling (collectively referred to as "DNA shuffling"). DNA shuffling may be employed to alter the characteristics of the antibody or fragments thereof (e.g., an antibody or a fragment thereof with higher affinities and lower dissociation rates). An antibody can further be a binding-domain immunoglobulin fusion protein as known in the art.

Variant Fc Regions

The present invention also includes binding members of the invention, and in particular the antibodies of the invention, that have modified IgG constant domains. Antibodies of the human IgG class, which have functional characteristics such as long half-life in serum and the ability to mediate various effector functions are used in certain embodiments of the invention (*Monoclonal Antibodies: Principles and Applications*, Wiley-Liss, Inc., Chapter 1 (1995)). The human IgG class antibody is further classified into the following 4 subclasses: IgG1, IgG2, IgG3 and IgG4. A large number of studies have so far been conducted for ADCC and CDC as effector functions of the IgG class antibody, and it has been reported that among antibodies of the human IgG class, the IgG1 subclass has the highest ADCC activity and CDC activity in humans (*Chemical Immunology*, 65, 88 (1997)).

"Antibody-dependent cell-mediated cytotoxicity" and "ADCC" refer to a cell-mediated reaction in which non-specific cytotoxic cells (e.g., Natural Killer (NK) cells, neutrophils, and macrophages) recognize bound antibody on a target cell and subsequently cause lysis of the target cell. In one embodiment, such cells are human cells. While not wishing to be limited to any particular mechanism of action, these cytotoxic cells that mediate ADCC generally express Fc receptors (FcRs). The primary cells for mediating ADCC, NK cells, express FcγRIII, whereas monocytes express FcγRI, FcγRII, FcγRIII and/or FcγRIV. FcR expression on hematopoietic cells is summarized in Ravetch and Kinet, Annu Rev. Immunol., 9:457-92 (1991). To assess ADCC activity of a molecule, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., Proc. Natl. Acad. Sci. (USA), 95:652-656 (1998).

Complement dependent cytotoxicity" or "CDC" refers to the ability of a molecule to initiate complement activation and lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santaro et al., J. Immunol. Methods, 202:163 (1996), may be performed.

Expression of ADCC activity and CDC activity of the human IgG1 subclass antibodies generally involves binding of the Fc region of the antibody to a receptor for an antibody (hereinafter referred to as "FcγR") existing on the surface of effector cells such as killer cells, natural killer cells or activated macrophages. Various complement components can be bound. Regarding the binding, it has been suggested that several amino acid residues in the hinge region and the second domain of C region (hereinafter referred to as "Cγ2 domain") of the antibody are important (*Eur. J. Immunol.*, 23, 1098 (1993), *Immunology*, 86, 319 (1995), *Chemical Immunology*, 65, 88 (1997)) and that a sugar chain in the Cγ2 domain (*Chemical Immunology*, 65, 88 (1997)) is also important.

"Effector cells" are leukocytes that express one or more FcRs and perform effector functions. The cells express at least FcγRI, FCγRII, FcγRIII and/or FcγRIV and carry out ADCC effector function. Examples of human leukocytes which mediate ADCC include peripheral blood mononuclear cells (PBMC), natural killer (NK) cells, monocytes, cytotoxic T cells and neutrophils. The terms "Fc receptor" or "FcR" are used to describe a receptor that binds to the Fc region of an antibody. In one embodiment, the FcR is a native sequence human FcR. Moreover, in certain embodiments, the FcR is one that binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See, Daëron, Annu Rev. Immunol., 15:203-234 (1997)). FcRs are reviewed in Ravetch and Kinet, Annu Rev. Immunol., 9:457-92 (1991); Capel et al., Immunomethods, 4:25-34 (1994); and de Haas et al., J. Lab. Clin. Med., 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., Immunol., 117:587 (1976) and Kim et al., J. Immunol., 24:249 (1994)).

In certain embodiments, an anti-alpha toxin antibody or fragment comprises an altered Fc region (also referred to herein as "variant Fc region") in which one or more alterations have been made in the Fc region in order to change functional and/or pharmacokinetic properties of the antibodies. Such alterations may result in a decrease or increase of C1q binding and complement dependent cytotoxicity (CDC) or of FcgammaR binding, for IgG. The present technology encompasses the antibodies described herein with variant Fc regions where changes have been made to alter the effector function, providing a desired effect. Accordingly, in some embodiments an anti-alpha toxin antibody or fragment comprises a variant Fc region (i.e., Fc regions that have been altered as discussed below). Anti-alpha toxin antibodies and fragments herein comprising a variant Fc region are also referred to here as "Fc variant antibodies." As used herein native refers to the unmodified parental sequence and the antibody comprising a native Fc region is herein referred to as a "native Fc antibody". In some embodiments, the variant Fc region exhibits a similar level of inducing effector function as compared to the native Fc region. In certain embodiments, the variant Fc region exhibits a higher induction of effector function as compared to the native Fc. In certain embodiments, the variant Fc region exhibits lower induction of effector function as compared to the native Fc. Some specific embodiments of variant Fc regions are detailed herein. Methods for measuring effector function are known in the art.

Effector function of an antibody can be modified through changes in the Fc region, including but not limited to, amino acid substitutions, amino acid additions, amino acid deletions and changes in post translational modifications to Fc amino acids (e.g., glycosylation). Methods described below may be used to alter the effector function of an isolated antibody or antigen binding fragment as described herein, resulting in an antibody or antigen binding fragment having certain properties advantageous for prophylaxis or treatment of a particular Staphylococcal *aureus*-associated disease or condition.

In some embodiments an Fc variant antibody is prepared that has altered binding properties for an Fc ligand (e.g., an Fc receptor, C1q) relative to a native Fc antibody. Examples of binding properties include but are not limited to, binding specificity, equilibrium dissociation constant ($K_d$), dissociation and association rates (koff and kon respectively), binding affinity and/or avidity. It is known in the art that the equilibrium dissociation constant ($K_d$) is defined as koff/kon. In certain aspects, an antibody comprising an Fc variant region with a low $K_d$ may be more desirable to an antibody with a high $K_d$. However, in some instances the value of the kon or koff may be more relevant than the value of the $K_d$. It can be determined which kinetic parameter is more important for a given antibody application.

In some embodiments, Fc variant antibodies exhibit altered binding affinity for one or more Fc receptors including, but not limited to FcRn, FcgammaRI (CD64) including isoforms FcgammaRIA, FcgammaRIB, and FcgammaRIC; FcgammaRII (CD32 including isoforms FcgammaRIIA, FcgammaRIIB, and FcgammaRIIC); and FcgammaRIII (CD16, including isoforms FcgammaRIIIA and FcgammaRIIIB) as compared to an native Fc antibody.

In certain embodiments, an Fc variant antibody has enhanced binding to one or more Fc ligand relative to a native Fc antibody. In certain embodiments, the Fc variant antibody exhibits increased or decreased affinity for an Fc ligand that is at least 2 fold, or at least 3 fold, or at least 5 fold, or at least 7 fold, a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or is between 2 fold and 10 fold, or between 5 fold and 50 fold, or between 25 fold and 100 fold, or between 75 fold and 200 fold, or between 100 and 200 fold, more or less than a native Fc antibody. In various embodiments, Fc variant antibodies exhibit affinities for an Fc ligand that are at least 90%, at least 80%, at least 70%, at least 60%, at least 50%, at least 40%, at least 30%, at least 20%, at least 10%, or at least 5% more or less than an native Fc antibody. In certain embodiments, an Fc variant antibody has increased affinity for an Fc ligand. An Fc variant antibody may sometimes have decreased affinity for an Fc ligand.

In some embodiments, an Fc variant antibody has enhanced binding to the Fc receptor FcgammaRIIIA. In some embodiments, an Fc variant antibody has enhanced binding to the Fc receptor FcgammaRIIB. In certain embodiments, an Fc variant antibody has enhanced binding to both the Fc receptors FcgammaRIIIA and FcgammaRIIB. In certain embodiments, Fc variant antibodies that have enhanced binding to FcgammaRIIIA do not have a concomitant increase in binding the FcgammaRIIB receptor as compared to a native Fc antibody. In certain embodiments, an Fc variant antibody has reduced binding to the Fc receptor FcgammaRIIIA. An Fc variant antibody may sometimes have reduced binding to the Fc receptor FcgammaRIIB. In various embodiments, an Fc variant antibody exhibiting altered affinity for FcgammaRIIIA and/or FcgammaRIIB has enhanced binding to the Fc receptor FcRn. In some embodiments, an Fc variant antibody exhibiting altered affinity for FcgammaRIIIA and/or FcgammaRIIB has altered binding to C1q relative to a native Fc antibody.

In certain embodiments, Fc variant antibodies exhibit affinities for FcgammaRIIIA receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or are between 2 fold and 10 fold, or between 5 fold and 50 fold, or between 25 fold and 100 fold, or between 75 fold and 200 fold, or between 100 and 200 fold, more or less than an native Fc antibody. In various embodiments, Fc variant antibodies exhibit affinities for FcgammaRIIIA that are at least 90%, at least 80%, at least 70%, at least 60%, at least 50%, at least 40%, at least 30%, at least 20%, at least 10%, or at least 5% more or less than an native Fc antibody.

In certain embodiments, Fc variant antibodies exhibit affinities for FcgammaRIIB receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or are between 2 fold and 10 fold, or between 5 fold and 50 fold, or between 25 fold and 100 fold, or between 75 fold and 200 fold, or between 100 and 200 fold, more or less than an native Fc antibody. In certain embodiments, Fc variant antibodies exhibit affinities for FcgammaRIIB that are at least 90%, at least 80%, at least 70%, at least 60%, at least 50%, at least 40%, at least 30%, at least 20%, at least 10%, or at least 5% more or less than an native Fc antibody.

In some embodiments, Fc variant antibodies exhibit increased or decreased affinities to C1q relative to a native Fc antibody. In some embodiments, Fc variant antibodies exhibit affinities for C1q receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or are between 2 fold and 10 fold, or between 5 fold and 50 fold, or between 25 fold and 100 fold, or between 75 fold and 200 fold, or between 100 and 200 fold, more or less than an native Fc antibody. In certain embodiments, Fc variant antibodies exhibit affinities for C1q that are at least 90%, at least 80%, at least 70%, at least 60%, at least 50%, at least 40%, at least 30%, at least 20%, at least 10%, or at least 5% more or less than an native Fc antibody. In various embodiments, an Fc variant antibody exhibiting altered affinity for Ciq has enhanced binding to the Fc receptor FcRn. In yet another specific embodiment, an Fc variant antibody exhibiting altered affinity for C1q has altered binding to FcgammaRIIIA and/or FcgammaRIIB relative to a native Fc antibody.

It is contemplated that Fc variant antibodies are characterized by in vitro functional assays for determining one or more FcgammaR mediated effector cell functions. In certain embodiments, Fc variant antibodies have similar binding properties and effector cell functions in in vivo models (such as those described and disclosed herein) as those in in vitro based assays. The present technology does not exclude Fc variant antibodies that do not exhibit the desired phenotype in in vitro based assays but do exhibit the desired phenotype in vivo.

The serum half-life of proteins comprising Fc regions may be increased by increasing the binding affinity of the Fc region for FcRn. The term "antibody half-life" as used herein means a pharmacokinetic property of an antibody that is a measure of the mean survival time of antibody molecules following their administration. Antibody half-life can be expressed as the time required to eliminate 50 percent of a known quantity of immunoglobulin from the patient's body (or other mammal) or a specific compartment thereof, for example, as measured in serum, i.e., circulating half-life, or in other tissues. Half-life may vary from one immunoglobulin or class of immunoglobulin to another. In general, an increase in antibody half-life results in an increase in mean residence time (MRT) in circulation for the antibody administered.

An increase in half-life allows for the reduction in amount of drug given to a patient as well as reducing the frequency of administration. An increase in half-life can also be beneficial, for example, for preventing a *Staphylococcal aureus*-associated disease or condition, and also for preventing a recurrence of infection that can often occur once a patient has been released from the hospital. To increase the serum half life of the antibody, one may incorporate a salvage receptor binding epitope into the antibody (especially an antibody fragment) as known in the art. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. Antibodies with increased half-lives may also be generated by modifying amino acid residues identified as involved in the interaction between the Fc and the FcRn receptor. In addition, the half-life of an anti-alpha toxin antibody or fragment may be increased by conjugation to PEG or Albumin by techniques widely utilized in the art. In some embodiments antibodies comprising Fc variant regions of an anti-alpha toxin antibody have an increased half-life of about 5%, about 10%, about 15%, about 20%, about 25%, about 30%, about 35%, about 40%, about 45%, about 50%, about 60%, about 65%, about 70%, about 80%, about 85%, about 90%, about 95%, about 100%, about 125%, about 150% or more as compared to an antibody comprising a native Fc region. In some embodiments antibodies comprising Fc variant regions have an increased half-life of about 2 fold, about 3 fold, about 4 fold, about 5 fold, about 10 fold, about 20 fold, about 50 fold or more, or is between 2 fold and 10 fold, or between 5 fold and 25 fold, or between 15 fold and 50 fold, as compared to an antibody comprising a native Fc region.

In some embodiments, the technology presented herein provides Fc variants, where the Fc region comprises a modification (e.g., amino acid substitutions, amino acid insertions, amino acid deletions) at one or more positions selected from the group consisting of 234, 235, 236, 237, 238, 239, 240, 241, 243, 244, 245, 247, 251, 252, 254, 255, 256, 262, 263, 264, 265, 266, 267, 268, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440 and 443 as numbered by the EU index as set forth in Kabat. Optionally, the Fc region may comprise a non naturally occurring amino acid residue at additional and/or alternative positions known in the art.

In a certain embodiments, provided herein is an Fc variant, where the Fc region comprises at least one substitution selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241 L, 241Y, 241E, 241R. 243W, 243L 243Y, 243R, 243Q, 244H, 245A, 247L, 247V, 247G, 251F, 252Y, 254T, 255L, 256E, 256M, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 305I, 313F, 316D, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 339T, 370E, 370N, 378D, 392T, 396L, 416G, 419H, 421K, 440Y and 434W as numbered by the EU index as set forth in Kabat. Optionally, the Fc region may comprise additional and/or alternative non-naturally occurring amino acid residues known in the art.

In various embodiments, provided herein is an Fc variant antibody, where the Fc region comprises at least one modification (e.g., amino acid substitutions, amino acid insertions, amino acid deletions) at one or more positions selected from the group consisting of 234, 235 and 331. In some embodiments, the non-naturally occurring amino acids are selected from the group consisting of 234F, 235F, 235Y, and 331S. Provided herein is an Fc variant, where the Fc region comprises at least one non-naturally occurring amino acid at one or more positions selected from the group consisting of 239, 330 and 332. Some embodiments, the non-naturally occurring amino acids are selected from the group consisting of 239D, 330L and 332E.

In some embodiments, provided herein is an Fc variant antibody, where the Fc region comprises at least one non-naturally occurring amino acid at one or more positions selected from the group consisting of 252, 254, and 256. In certain embodiments, the non-naturally occurring amino acids are selected from the group consisting of 252Y, 254T and 256E, described in U.S. Pat. No. 7,083,784, the contents of which are herein incorporated by reference in its entirety.

In certain embodiments, provided herein is an anti-Staphylococcal alpha toxin antibody having an Fc variant region that increases the serum-half life of the antibody, where the antibody has the following heavy chain and light chain sequences:

```
Heavy Chain: LC10-IgG1-YTE
                                                      (SEQ ID NO: 91)
EVQLVESGGGLVQPGGSLRLSCAASGFTFSSHDMHVVVRQATGKGLEWVSGIGTAGDTYYPDSV

KGRFTISRENAKNSLYLQMNSLRAGDTAVYYCARDRYSPTGHYYGMDVWGQGTTVTVSSASTKG

PSVFPLAPSSKSTSGGTAALGCLVKDYFPEPVTVSWNSGALTSGVHTFPAVLQSSGLYSLSSVVT
```

-continued
```
VPSSSLGTQTYICNVNHKPSNTKVDKRVEPKSCDKTHTCPPCPAPELLGGPSVFLFPPKPKDTLYI

TREPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALHNHYTQKSLSLSPGK.
```

Light Chain: LC10-Kappa (SEQ ID NO: 92)
```
DIQMTQSPSTLSASVGDRVTITCRASQSISSWLAWYQQKPGKAPKLLIYKASSLESGVPSRFSGSG

SGTEFTLTISSLQPDDFATYYCKQYADYWTFGQGTKVEIKRTVAAPSVFIFPPSDEQLKSGTASVV

CLLNNFYPREAKVQWKVDNALQSGNSQESVTEQDSKDSTYSLSSTLTLSKADYEKHKVYACEVT

HQGLSSPVTKSFNRGEC
```

In certain embodiments the effector functions elicited by IgG antibodies strongly depend on the carbohydrate moiety linked to the Fc region of the protein. Thus, glycosylation of the Fc region can be modified to increase or decrease effector function. Accordingly, in some embodiments the Fc regions of anti-alpha toxin antibodies and fragments provided herein comprise altered glycosylation of amino acid residues. In certain embodiments, the altered glycosylation of the amino acid residues results in lowered effector function. In certain embodiments, the altered glycosylation of the amino acid residues results in increased effector function. In some embodiments, the Fc region has reduced fucosylation. In certain embodiments, the Fc region is afucosylated.

In some embodiments, the Fc variants herein may be combined with other known Fc variants as known in the art. Other modifications and/or substitutions and/or additions and/or deletions of the Fc domain can be introduced.

Glycosylation

In addition to the ability of glycosylation to alter the effector function of antibodies, modified glycosylation in the variable region can alter the affinity of the antibody for a target antigen. In some embodiments, the glycosylation pattern in the variable region of the present antibodies is modified. For example, an aglycoslated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. One or more amino acid substitutions can also be made that result in elimination of a glycosylation site present in the Fc region (e.g., Asparagine 297 of IgG). Furthermore, aglycosylated antibodies may be produced in bacterial cells which lack the necessary glycosylation machinery.

Antibody Conjugates

In certain embodiments, the antibodies presented herein are conjugated or covalently attached to a substance using methods known in the art. In some embodiments, the attached substance is a detectable label (also referred to herein as a reporter molecule) or a solid support. Suitable substances for attachment to antibodies include, but are not limited to, an amino acid, a peptide, a protein, a polysaccharide, a nucleoside, a nucleotide, an oligonucleotide, a nucleic acid, a hapten, a drug, a hormone, a lipid, a lipid assembly, a synthetic polymer, a polymeric microparticle, a biological cell, a virus, a fluorophore, a chromophore, a dye, a toxin, a hapten, an enzyme, an antibody, an antibody fragment, a radioisotope, solid matrixes, semi-solid matrixes and combinations thereof. Methods for conjugation or covalently attaching another substance to an antibody are known in the art.

Diagnostic Methods of Use

Alpha toxin is a virulence factor usually found only in pathogenic strains of *S. aureus*. Alpha toxin sometimes binds to a cell surface receptor as part of the formation of active complexes. However, oligomerization and formation of a transmembrane pore (e.g., alpha toxin heptamer) can occur in the absence of binding to a specific receptor. The action of oligomerized alpha toxin in cell dysfunction and lysis (e.g., formation of a transmembrane pore) facilitates colonization of invading *S. aureus* bacteria. Antibodies described herein inhibit the assembly or oligomerization of alpha toxin monomers into a transmembrane pore by recognizing a region on the alpha toxin molecule directly or indirectly involved with alpha toxin monomer-monomer interaction.

In certain embodiments, anti-alpha toxin antibodies and fragments and compositions herein presented may be used in vivo and/or in vitro for diagnosing *S. aureus* strains that produce alpha toxin and/or alpha toxin associated conditions/diseases. This can be achieved, for example, by contacting a sample to be tested, optionally along with a control sample, with the antibody under conditions that allow for formation of a complex between the antibody and alpha toxin. Complex formation is then detected (e.g., using an ELISA). When using a control sample along with the test sample, complex is detected in both samples and any statistically significant difference in the formation of complexes between the samples is indicative of the presence of *S. aureus*, alpha toxin or *S. aureus* and alpha toxin in the test sample.

In some embodiments, the technology herein provides a method of determining the presence of *S. aureus* strains that produce alpha toxin and/or alpha toxin in a sample suspected of containing *S. aureus* and/or other alpha toxin homolog producing bacteria, the method comprising exposing the sample to an anti-alpha toxin antibody or fragment, and determining binding of the antibody to alpha toxin in the sample where binding of the antibody to alpha toxin in the sample is indicative of the presence of the *S. aureus* and/or alpha toxin in the sample. In some embodiments, the sample is a biological sample. In certain embodiments, the biological sample is from a mammal experiencing or suspected of experiencing a *S. aureus* associated disease/disorder.

In certain embodiments, an anti-alpha toxin antibody or fragment may be used to detect the growth of *S. aureus* and/or over-expression of alpha toxin using an in vivo diagnostic assay. In some embodiments, the anti-alpha toxin antibody or fragment is added to a sample where the antibody binds the alpha toxin to be detected and is tagged with a detectable label (e.g., a radioactive isotope or a fluorescent label) and externally scanning the patient for localization of the label.

FISH assays such as the INFORM™ (sold by Ventana, Arizona) or PATHVISION™ (Vysis, Ill.) may be carried out on formalin-fixed, paraffin-embedded tissue to determine the extent (if any) of alpha toxin overexpression in the tissue sample.

In certain embodiments, the anti-alpha toxin antibodies and fragments may be used in a method of detecting alpha toxin in tissue samples, blood or serum (e.g., soluble alpha toxin). In some embodiments, the method comprises contacting a test sample of tissue, blood or serum from a mammal suspected of experiencing an S. aureus alpha toxin mediated disorder with an anti-alpha toxin antibody or fragment presented herein and detecting an increase in alpha toxin in the test sample relative to a control sample of blood or serum from a normal mammal. In some embodiments, the method of detecting is useful as a method of diagnosing a S. aureus and/or alpha toxin mediated disorder associated with an increase in alpha toxin in tissue, blood or serum of a mammal.

Therapeutic Methods of Use

In certain embodiments, an anti-alpha toxin antibody or fragment may be administered for prevention and/or treatment of an alpha toxin mediated condition. Herein presented are methods of preventing, treating, maintaining, ameliorating, and/or inhibiting an alpha toxin-mediated disease or disorder, where the methods comprise administering anti-alpha toxin antibodies and fragments provided herein.

Pathogenic Staphylococcus aureus Alpha Toxin-Mediated Disorders

In certain embodiments, provided are methods of administering and using compositions and antibodies as presented herein to treat and prevent a wide range of pathogenic Staphylococcus aureus mediated conditions/diseases, including both chronic and acute conditions, such as, but not limited to, bacteremia, burns, cellulitis, dermonecrosis, eyelid infections, food poisoning, joint infections, neonatal conjunctivitis, osteomyelitis, pneumonia, skin infections, surgical wound infection, scalded skin syndrome, endocarditis, meningitis, abscess formation and toxic shock syndrome.

Both CA-MRSA and HA-MRSA are resistant to traditional anti-staphylococcal beta-lactam antibiotics, such as cephalexin. CA-MRSA has a greater spectrum of antimicrobial susceptibility, including to sulfa drugs (like co-trimoxazole/trimethoprim-sulfamethoxazole), tetracyclines (like doxycycline and minocycline) and clindamycin, but the drug of choice for treating CA-MRSA is now believed to be vancomycin, according to a Henry Ford Hospital Study. HA-MRSA is resistant even to these antibiotics and often is susceptible only to vancomycin. Newer drugs, such as linezolid (belonging to the newer oxazolidinones class) and daptomycin, are effective against both CA-MRSA and HA-MRSA.

In certain embodiments, the antibody or antigen-binding fragment thereof of the present invention can be used in combination with an antibiotic that corresponds to, for example, beta-lactam antibiotics (such as cephalexin), sulfa drugs (like co-trimoxazole/trimethoprim-sulfamethoxazole), tetracyclines (like doxycycline and minocycline), clindamycin, vancomycin, linezolid, daptomycin, teicoplanin, quinupristin/dalfopristin (synercid), or tigecycline.

Pharmaceutical Formulations

In certain embodiments, an anti-alpha toxin antibody or fragment provided herein may be formulated with a pharmaceutically acceptable carrier as pharmaceutical (therapeutic) compositions, and may be administered by a variety of methods known in the art. The route and/or mode of administration may vary depending upon the desired results. As used herein, the pharmaceutical formulations comprising an anti-alpha toxin antibody or fragment are referred to as formulations of the technology. The term "pharmaceutically acceptable carrier" means one or more non toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co mingled with the antibodies of the present technology, and with each other, in a manner such that there is no interaction which would substantially impair the desired pharmaceutical efficacy.

Therapeutic compositions of the present technology may be formulated for a particular dosage. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the anti-alpha toxin antibody or fragment and the particular therapeutic effect to be achieved, and (b) the limitations inherent in the art of compounding such an anti-alpha toxin antibody or fragment for the treatment of sensitivity in individuals.

Therapeutic compositions of the present technology can be formulated for particular routes of administration, such as oral, nasal, pulmonary, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect.

Therapeutically Effective Dosages

An antibody formulation described herein can be administered at a suitable dosage and dosage regimen, and such dosage and dosage regimen can depend on the disease or condition to be treated. A therapeutically effective dosage can be identified by determining whether a dosage and dosage regimen gives rise to a therapeutic effect or therapeutic end-point Articles of Manufacture and Kits Herein provided is a pharmaceutical pack or kit comprising one or more containers filled with a liquid formulation or lyophilized formulation herein. In some embodiments, a container filled with a liquid formulation herein is a pre-filled syringe. In specific embodiments, the formulations herein comprise anti-alpha toxin antibodies and fragments recombinantly fused or chemically conjugated to another moiety, including but not limited to, a heterologous protein, a heterologous polypeptide, a heterologous peptide, a large molecule, a small molecule, a marker sequence, a diagnostic or detectable agent, a therapeutic moiety, a drug moiety, a radioactive metal ion, a second antibody, and a solid support. In certain embodiments, the formulations herein are formulated in single dose vials as a sterile liquid. A formulation herein is sometimes supplied in a pre-filled syringe.

In certain embodiments, kits comprising anti-alpha toxin antibodies and fragments are also provided that are useful for various purposes, e.g., research and diagnostic including for purification or immunoprecipitation of alpha toxin from cells, detection of alpha toxin, and the like. For isolation and purification of alpha toxin, the kit may contain an anti-alpha toxin antibody or fragment coupled to beads (e.g., sepharose beads). Kits may be provided which contain the antibodies for detection and quantification of alpha toxin in vitro, e.g., in an ELISA or a Western blot. As with the article of manufacture, the kit comprises a container and a label or package insert on or associated with the container. The container holds a composition comprising at least one anti-alpha toxin antibody or fragment as herein disclosed. Additional containers may be included that contain, e.g., diluents and buffers, control antibodies. The label or package insert may provide a description of the composition as well as instructions for the intended in vitro or diagnostic use.

The present technology also encompasses a finished packaged and labeled pharmaceutical product. This article of manufacture includes the appropriate unit dosage form in an appropriate vessel or container such as a glass vial, pre-filled syringe or other container that is hermetically sealed. In some embodiments, the unit dosage form is provided as a sterile particulate free solution comprising an anti-alpha toxin antibody or fragment that is suitable for parenteral administration. In certain embodiments, the unit dosage form is provided as a sterile lyophilized powder comprising an anti-alpha toxin antibody or fragment that is suitable for reconstitution.

In some embodiments, the unit dosage form is suitable for intravenous, intramuscular, intranasal, oral, topical or subcutaneous delivery. Thus, the technology encompasses sterile solutions suitable for each delivery route. The technology further encompasses sterile lyophilized powders that are suitable for reconstitution.

As with any pharmaceutical product, the packaging material and container are designed to protect the stability of the product during storage and shipment. Further, the products herein include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, and other monitoring information.

Specifically, the technology provides an article of manufacture comprising packaging material, such as a box, bottle, tube, vial, container, pre-filled syringe, sprayer, insufflator, intravenous (i.v.) bag, envelope and the like; and at least one unit dosage form of a pharmaceutical agent contained within the packaging material, where the pharmaceutical agent comprises a liquid formulation containing an antibody. The packaging material includes instruction means which indicate how that the antibody can be used to prevent, treat and/or manage one or more symptoms associated with a disease or disorder.

EXAMPLES

The examples set forth below illustrate certain embodiments and do not limit the technology.

Example 1

Materials and Methods

Materials and methods utilized for Example 2 to Example 9 and Example 11 to Example 13 are provided hereafter.

Cloning and Expression of Wt *S. Aureus* AT and Non-Hemolytic Mutant H35L

Genomic DNA from *Staphylococcus aureus* strain ATCC BAA1556 was used to amplify the wild type alpha toxin (AT) gene by PCR. The reaction contained forward primer, atatatgagctcgcagattctgatattaatattaaaacc (SEQ ID NO: 41), reverse primer, atatataagcttaatttgtcatttcttcttttttccc (SEQ ID NO: 42), and approximately 10 ng of genomic DNA in a 50 µl reaction using Herculase II polymerase (Stratagene). The resultant fragment was digested with Sac I and Hind III and ligated into the pCold II DNA vector (TaKaRa), in frame with an N terminal 6×His tag. The H35L mutant was generated by site directed mutagenesis of the wild type gene using a QuikChange II XL site directed mutagenesis kit (Stratagene), according to manufacturer's instructions. The mutagenic primers utilized for the mutagenesis were gataaagaaaatggcatgctcaaaaaagtattttatagttttatc (SEQ ID NO: 43) and gataaaactataaaatacttttttgagcatgccattttctttatc (SEQ ID NO: 44).

The sequences of the wild type AT and $AT_{H35L}$ mutant were confirmed by automated DNA sequencing. Wild type and H35L mutant alpha toxin were expressed in *E. coli* strain BL21. A 50 ml overnight culture grown in LB plus carbenicillin was diluted 1:10 in a 500 ml culture and grown at 37° C. to an $A_{600}$ of about 0.5. The culture was shifted to 15° C. for 30 minutes and then 1 M IPTG was added to achieve a final concentration of about 100 mM. The culture was incubated for an additional 24 hours at 15° C. Cells were harvested by centrifugation.

Purification of Recombinant, his-Tagged Alpha Toxin (rAT-his)

Bacterial cell pellets were thawed on ice and resuspended in Ni-NTA buffer A (20 mM Sodium Phosphate, pH 7.2, 300 mM NaCl). Cells were lysed by microfluidization (Microfluidics Model M-110P) at 20,000 psi and the crude lysate was clarified by centrifugation at 27,000×g for 10 min. at 4° C. Following 0.2 µm-filtration, the supernatant was loaded onto a 5 ml Ni-NTA Superflow column (Qiagen) equilibrated with Ni-NTA Buffer A. rAT-his was eluted with a 300 mM and 500 mM imidazole step gradient, fractions were collected in tubes containing EDTA at a final concentration of 1 mM, and dialyzed into SP buffer A (50 mM Sodium Phosphate, pH 7.0, 25 mM NaCl, 1 mM EDTA). Dialysates were loaded onto a 5 ml HiTrap SP Sepharose FF column (GE Healthcare) in SP Buffer A and rAT-his was eluted with a step gradient to 1 M NaCl. Fractions containing rAT-his were dialyzed into 1×PBS, pH 7.2 with 1 mM EDTA and aliquots were frozen at −80° C.

Purification of Native Alpha Toxin from S. Aureus

Native alpha toxin (nAT) was purified from the S. aureus Wood strain. S. aureus Wood was grown overnight in tryptic soy broth (TSB) at 37° C., with shaking (e.g., about 250 RPM). Culture supernatant was harvested by centrifugation then brought to 75% saturation with solid ammonium sulfate. After stirring for 3 hours at 4° C., the precipitate was captured by centrifugation at 12,000×g for 45 min., resuspended in SP buffer A (25 mM sodium acetate, pH 5.2, 20 mM NaCl, 1 mM EDTA) and dialyzed against SP buffer A overnight at 4° C. with one exchange. Insoluble material was removed by centrifugation at 27,000×g for 30 min. at 4° C. The soluble dialysate was filtered (0.2 µm) and loaded onto a 10 ml SP Sepharose FF column (GE Healthcare) equilibrated with SP buffer A. Bound nAT was eluted with a linear gradient to 300 mM NaCl, followed by steps at 0.5 and 1 M NaCl. Fractions containing nAT were pooled and dialyzed overnight into PBS, pH 7.2 containing 1 mM EDTA. For final processing, the dialysate was loaded onto a HiPrep Sephacryl S-200 High Resolution column (GE Healthcare) at a flow rate of 1.3 ml/min in 1×PBS, pH 7.2 with 1 mM EDTA. Fractions containing nAT were pooled, aliquoted, and frozen at −80° C.

Immunization/Hybridoma Generation

Eight-week old VelocImmune mice received 5 rounds of subcutaneous injections of the $rAT_{H35L}$ at multiple sites following the RIMMS Immunization regime Kilpatrick et al (1997). Mice were immunized over a course of 13 days at intervals of 2-3 days. For each round of immunization, mice were first anesthetized with isofluorane. The immunogen was emulsified in complete or incomplete Freund's adjuvant and TiterMax Gold adjuvant and injected bilaterally at the nape of the neck, axilla, calf and groin. Test bleeds were collected on day 13 and assayed in an antigen ELISA. Mice were given a pre-fusion boost intraperitoneally and sacrificed on day 17. Lymph node lymphocytes and splenocytes were fused to a myeloma partner to generate stable hybridomas.

Neutralization of Hemolytic Activity

Fifty microliters of each B cell hybridoma culture supernatant was mixed with recombinant alpha toxin-His (rAT-his, 0.1 mg/ml final concentration) in 96 well plates, followed by the addition of 50 µl of 5% rabbit red blood cells (RBC) in PBS. Control wells contained RBC and culture media alone with or without AT. Plates were incubated for 1 h at 37° C., and the intact cells pelleted by centrifugation. 50 µl of the supernatants were transferred to a new 96 well plate and the $A_{490}$ measured in a spectrophotometer. Neutralizing activity was calculated relative to lysis with RBC and rAT-his alone and calculated: % inhibition=100×[100−($A_{490}$ nAT+Ab)/($A_{490}$ nAT no Ab)].

Inhibition with the purified mAbs also was tested. Anti-AT mAbs were added to a 96-well plate at about 80 µg/mL in PBS and the samples serially diluted (twofold) in PBS to a final volume of 50 µL. A nonspecific IgG1 (R347) was included as an isotype control. Twenty five microliter of mAb dilutions were mixed with 25 µL of nAT (native alpha toxin) at about 0.1 µg/mL in 96 well round bottom plates, followed by the addition of 50 µL 5% RBC. Inhibition of hemolytic activity was calculated as above.

Expression and Purification of Chimeric Anti-AT mAbs

Clarified murine anti-AT supernatants (approximately 5 L @ 30-50 mg/L) were concentrated by tangential flow filtration. The concentrated supernatants were then passed over five 5 mL Protein G HiTrap HP columns in sequence and the bound IgG was eluted with 50 mM sodium bicarbonate pH 11.0 and neutralized to approximately pH 7.0 with 1M phosphoric acid. The neutralized material was loaded onto a two 1 mL HiTrap Q FF (GE Healthcare) columns in sequence. The IgG containing flow through was collected and dialyzed into PBS pH 7.2.

Neutralization of A549 Lysis

A549 cells were maintained in a 5% $CO_2$ 37° C. incubator in RMPI supplemented with non essential amino acid, glutamine and 10% fetal bovine serum. Cells were washed once with Hank's balanced media, and plated at $10^4$/well under 50 µl in RPMI, 5% FBS, and incubated at 37° C. with 5% $CO_2$ for 20 hr. Anti-AT mAbs were added to a 96-well plate at 80 µg/mL in RPMI and the samples serially diluted (two-fold) in RPMI. An irrelevant IgG1 (R347) was included as an isotype control. In a separate 96-well plate, 30 µl of the diluted antibodies were mixed with 30 µl of nAT (final concentration, 5 µg/ml). Fifty microliters from each well was transferred to the plate containing adherent A549 cells. Control wells of A549 cells with or without nAT were included. Plates were incubated 37° C. with 5% $CO_2$ for 3 h, centrifuged and 50 µl supernatant transferred to a new 96-well plate. Cell lysis was measured as the release of lactate dehydrogenase (LDH) using a Cytotox 96 non radioactive assay kit (Promega) following the manufacturer's protocol. Background LDH was subtracted from each well and the inhibition of LDH release calculated: % inhibition=100×[100−($A_{590}$ nAT+Ab)/($A_{590}$ nAT no Ab)].

Neutralization of THP-1 Lysis

THP-1 cells were maintained in a 5% $CO_2$ 37° C. incubator in RPMI medium (Invitrogen) supplemented with non essential amino acids (Invitrogen), 2 mM glutamine (Invitrogen) and 10% fetal bovine serum (Invitrogen). Anti-AT mAbs were added to a 96-well plate at 80 µg/ml in RPMI and the samples serially diluted (two-fold) in RPMI to a final volume of 50 µL. An irrelevant IgG1 (R347) was included as an isotype control. Twenty five microliters of the mAb dilutions were mixed with 25 µl native alpha toxin (nAT) at 1.5 µg/ml final, followed by the addition of 50 µl of RMPI washed THP-1 cells ($10^6$ cells/ml in RPMI with 10% FBS) in a 96-well plate. Control wells consisted in THP-1 cells with alone or with nAT. Plates were incubated in a 5% $CO_2$ 37° C. incubator for 3 h, centrifuged and 50 µl of the supernatant transferred to a new 96 well plate. Cell lysis was measured as the release of lactate dehydrogenase (LDH) using the Cytotox 96 non radioactive assay kit (Promega) following the manufacturer's instructions. Inhibition of LDH release was calculated as described above.

Cloning of Anti-AT IgG mAbs and Expression as Fully Human mAbs

The mRNA of five hybridoma clones 2A3, 10A7, 12B8, 25E9 and 28F6 were isolated using Dynabeads mRNA Direct Kit (Invitrogen). The first-strand of cDNA was synthesized using SuperScript III (Invitrogen) reverse transcriptase and random heptamer primers. Human Ig $V_L$ (kappa) and $V_H$ were amplified by PCR using an Ig-primer set (Novagen, Catalog #69830). The PCR amplified VL and VH products were cloned into TOPO TA vector (Invitrogen pCR2.1-TOPO) and sequenced. The $V_H$ and $V_L$ (kappa) from each hybridoma were re-amplified by PCR adding restriction enzyme sites for cloning into human IgG.kappa. pOE vector, where $V_L$ was cloned at BssHII/BsiWI site fused with human c-kappa, and $V_H$ was cloned at BsrGI/SalI site fused with human IgG-1 heavy chain constant region. The resulting pOE plasmids were verified by DNA sequencing.

Anti-Alpha Toxin mAb Expression and Purification

Plasmid DNA of the pOE constructs was prepared using Endofree Plasmid Maxi kit (Qiagen). The pOE plasmids were transfected into 293F suspension cells using 293fectin reagent (Invitrogen) in Freestyle 293 expression medium (GIBCO). Days 6 and 9 post transfection, the culture medium was harvested and the IgG purified using a protein A-sepharose column (GE Healthcare). The IgG containing peaks were pooled, dialyzed into PBS, pH 7.4 and stored at −70° C. The purity of the IgG proteins was verified by SDS-PAGE.

Murine Pneumonia Model.

Twenty-four hours prior to infection groups of ten 7-9 wk-old C57BL/6J mice (Harlan) received 0.5 ml of mAb at the concentrations indicated via i.p injection. The animals were then anesthetized with isofluorane, held vertically and 0.05 ml of S. aureus bacterial suspension ($1 \times 10^8$ CFU to $3 \times 10^8$ CFU) in sterile PBS were inoculated into the left and right nostrils. Animals were placed into a cage in a supine position for recovery and were observed twice daily for the time course of study. Animal survival was monitored for a maximum of 6 days.

Alternatively, animals were euthanized by $CO_2$ inhalation 48 h after bacteria infection. A lung and kidney were removed into sterile PBS, homogenized, diluted and plated for bacterial enumeration. Statistical significance of mortality studies was determined using log-rank test. The significance of bacterial recovery from organs was calculated using analysis of variance and Dunnett's post-test.

Murine Model of Dermonecrosis

Groups of five 6-8 weeks old female BALB/c mice (Harlan) were shaved on their back and administered by intraperitoneal injection of 0.5 ml IgG at the concentration indicated on the graph. Twenty-four hours later, the mice were infected by subcutaneous injection of 50 µL of a bacterial suspension ($1 \times 10^8$ S. aureus). The animals were monitored twice daily for signs of infection and the size of the abscess measured at the same time daily. The area of the lesions was calculated using the formula $A = L \times W$. Statistical significance was determined using analysis of variance and Dunnett's post-test.

Receptor Binding Assay

Red blood cell ghosts were prepared by incubating 5 mL of washed and packed rabbit red blood cells (RBC) in 500 mL of lysis buffer (5 mM phosphate, 1 mM EDTA, pH 7.4) o/n at 4° C. with constant stirring. The ghosts were then removed by centrifugation at 15,000×g and washed 3× with lysis buffer. They were then washed in PBS and resuspended in a final volume of 3 mL.

To assess binding of nAT to cell membranes RBC ghosts were diluted to $OD_{600}$ approximately 0.2 in PBS and 50 µL were coated onto ½-well 96 well plates (Costar) and incubated overnight at 4° C. The liquid was then removed from the plates and the wells were blocked with 100 µL of 1% BSA in PBS, pH7.4 for 2 hr at 4° C. and washed 3× with PBS. A 20 molar excess of IgG was mixed with nAT at 3 µg/mL and 50 µL was added to the blocked plates. The plates were incubated at 4° C. fro 2 hr and washed 3× with PBS. Biotin labeled rabbit anti-AT IgG was added to the wells at 1 mg/mL and incubated at 4° C. for 1 hr, washed 3× and incubated with streptavidin peroxidase conjugate (1:30,000, Jackson Immunoresearch). The wells were washed 3× and developed with Sure Blue Reserve (KPL, Inc.). The $A_{450}$ was read using a plate reader (Molecular Devices) and the % AT bound calculated. % AT bound=$100 \times (A_{450} - AT+IgG/A_{450} - AT$ alone)

Oligomerization Assay

Liposomes were generated using a Liposofast Extruder (Avestin, Inc.) and a membrane with a 100 nm pore size. A mixture (5:1:4, molar ratio) of egg yolk phosphatidylcholine (15 mg, Avanti Polar Lipids), egg yolk phosphatidylglycerol (2.9 mg, Avanti Polar Lipids) and cholesterol (5.8 mg, Avanti Polar Lipids) in chloroform was dried at 40 C under stream of nitrogen. The dried lipid film was then rehydrated with 3 mL PBS, pH 7.4 (Invitrogen) and incubated at 37° C. for 30 min. The sample was then vortexed vigorously until it formed an even suspension and then underwent 3 rounds of freeze thaw using a dry ice isopropanol bath and room temperature water. The solution was then passed through the Liposofast extruder 21 times.

AT (0.5 µg) was mixed with purified IgG, 5 µL RBC ghosts and PBS in a final volume of 22 µL and incubated at 37° C. for 45 min. The samples were then solubilized in 5 µL SDS-PAGE sample buffer for 5 min at 37° C. and 10 µL subjected to SDS-PAGE in a 4-12% precast polyacrylamide gel (Invitrogen). The separated proteins were then transferred to nitrocellulose, blocked for 10 min with Blocker Casein in PBS (Thermo Scientific) and probed with rabbit anti-AT IgG (2 µg/mL) for 2 hr at room temperature with constant shaking. The AT bands were detected following a 1 hr incubation with a alkaline phosphatase labeled goat anti-rabbit 2 and developed using BCIP/NBT membrane phosphatase substrate system (KPL, Inc.).

Measurement of Kinetic Rate and Binding Constants ($K_D$)

Kinetic rate constants ($k_{on}$, $k_{off}$) for the binding of the anti-AT IgG antibodies to purified nAT were measured employing an IgG-capture assay format on a BIAcore 3000 instrument (BIAcore, Inc). Briefly, a rat anti-mouse-IgG was immobilized on a CM5 sensor chip according to manufacturer's instructions. The final surface density of the capture reagent on the sensor chip was approximately 2500 response units (RUs), as described herein. A reference flow cell surface was also prepared on this sensor chip using the identical immobilization protocol, and omitting nAT. Anti-AT IgG antibodies were prepared at 20 nM in instrument buffer (HBS-EP buffer containing 0.01 M HEPES, pH 7.4, 0.15 M NaCl, 3 mM EDTA and 0.005% P-20) along with two-fold serial dilutions of the nAT. nAT serial dilutions were made in the range of about 0.78 nM to about 50 nM, in instrument buffer.

A sequential approach was utilized for kinetic measurements. Each anti-AT IgG was first injected over the capture and reference surfaces at a flow rate of 50 µL/min. Once the binding of the captured IgG had stabilized, a single concentration of the nAT protein was injected over both surfaces, at a flow rate of 50 µL/min. The resultant binding response curves was used to determine the association phase data. Following the injection of the nAT, the flow was then switched back to instrument buffer for 10 minutes to permit the collection of dissociation phase data followed by a 1 minute pulse of 10 mM glycine, pH 1.5 to regenerate the IgG capture surface on the chip. Binding responses from duplicate injections of each concentration of nAT were recorded against all anti-AT IgGs.

Additionally, several buffer injections were interspersed throughout the injection series. Select buffer injections were used along with the reference cell responses to correct the raw data sets for injection artifacts and/or non-specific binding interactions commonly referred to as "double-referencing" (D. G. Myszka, Improving biosensor analysis. *J. Mol. Recognit.* 12 (1999), pp. 279-284). Fully corrected binding data was then globally fit to a 1:1 binding model (BIAevaluation 4.1 software, BIAcore, Inc, Uppsala, Sweden) that included a term to correct for mass transport-limited binding, should it be detected. These analyses determined the kinetic rate (on, off) constants, from which the apparent $K_D$ was then calculated as $k_{off}/k_{on}$.

Measurement of Cytokine Levels in *S. Aureus* Infected Lungs

Seven to nine wk-old C57BL/6J mice were treated with 2A3.1hu (fully human 2A3.1) or R347 (45 mg/kg) by intraperitoneal injection 24 h before intranasal infection with $1.5 \times 10^8$ cfu USA300 (BAA-1556, ATCC). Four and twenty-four hours post infection the mice were euthanized and the lungs were flushed 3× with 1 ml of PBS. The bronchoalveolar lavage fluid (BAL) was stored at −70° C. Proinflammatory cytokines were quantified using the 7 pro-inflammatory II mouse cytokine kit (Mesoscale, Gaithersburg, Md.) according to manufacturer's instructions. Cytokine levels were expressed as pg/ml.

Cloning and Expression of GST Fusion Proteins

Gene sequences encoding $AT_{1-50}$ and $AT_{51-293}$ were amplified by PCR from the pColdII AT clone described above. The reactions contained 10 ng of AT-pColdII DNA and 0.1 mg of each forward and reverse primers ($AT_{1-50}$-F, atattggatccgcagattctgatattaatattaaaac (SEQ ID NO: 45) and $AT_{1-50}$-R, atacttctcgagttatttattatgattttatcatcgataaaac (SEQ ID NO: 46); or $AT_{51-203}$-F catagggatccaaactgctagttattagaacgaaag (SEQ ID NO: 47) and $AT_{51-203}$-R, catagctcgagtcaattt-gtcatttcttcttttttcccaatc (SEQ ID NO: 48)), and **PCR polymerase used, (Invitrogen) according to manufacturer's instructions. The resultant PCR fragment was digested with BamHI and XhoI and ligated into the pGex 6P DNA vector (Stratagene) in frame with the N terminal glutathione S transferase (GST) tag. The sequences of the clones were confirmed by automated DNA sequencing.

Expression of the fragments was accomplished with the BL21 (DE3) strain of *E. coli* as host. Several colonies were picked from a plate and inoculated into 100 mL LB+100 µg/mL ampicillin (Sigma Chemical Company) and grown o/n at 37° C. The overnight cultures were diluted 1:100 into 3×1 L cultures of LB+100 µg/mL ampicillin and grown with shaking at approximately 250 RPM to an OD600 of approximately 0.8. Protein expression was then induced by the addition of 1 mM IPTG. Cultures continued incubation for 2 hr at 37° C. with shaking. Bacterial cells were harvested by centrifugation and frozen at −20° C.

Cell pellets were resuspended in 100 mL PBS, pH 7.4 (Invitrogen) and lysed by microfluidization (Microfluidics Model M-110P) at 20,000 psi and the crude lysate was clarified by centrifugation at 27,000×g for 10 min. at 4° C. The resulting supernatant was loaded onto a GSTrap FF column (GE Healthcare) and GST-$AT_{1-50}$ and the soluble fraction of GST-$AT_{51-293}$ were purified following the manufacturer's instructions. The insoluble GST-$AT_{51-293}$ fraction was purified from the insoluble cell pellets. The insoluble material was solubilized for about one hour at room temperature, with gentle rocking, in 3 M guanidine-HCl in 25 mM sodium phosphate, pH 7.4. Solubilized material was diluted 7-fold with refolding buffer A [25 mM Sodium Phosphate, pH 7.4 with 2 M Guanidine-HCl]. GST-$AT_{51-293}$ was refolded by gradual dialysis. An equal volume of refolding buffer B [25 mM Sodium Phosphate, pH 7.4] was added to the dialysis beaker after every 12-15 hours of dialysis at 4° C. for a guanidine concentration of approximately 2, 1, then 0.5 M. GST-$AT_{51-293}$ was then dialyzed against refolding buffer B for 24 hours. The final dialysate was clarified by centrifugation and the soluble fraction purified over a GSTrap column as described above.

Dot Blot Assays

Overlapping peptides spanning amino acid 40 to 293 were chemically synthesized (New England Peptide). Synthesis of $AT_{1-50}$ was attempted but not successful. Alpha toxin (AT), AT peptides and AT fragments (1 µg) were spotted on nitrocellulose and blocked 10 min with Blocker Casein in PBS. The blots were then probed with 2 µg/mL of the individual IgG for 3 hr at room temperature.

The blots were washed and incubated with an alkaline phosphatase conjugated goat anti-mouse or goat anti rabbit IgG (1:1000, Caltag Laboratories) for 1 hr and developed using BCIP/NBT membrane phosphatase substrate system (KPL, Inc).

ELISA Characterization of the Binding of LC10 YTE to Alpha Toxin and LukF-PV

Bacterial lysate containing His-tagged alpha toxin or LukF-PV was coated on the surface of a 96-well plate overnight at 4° C. Plates were washed six times with PBS/0.05% Tween 20 and blocked with 10% Superblock blocking buffer (Pierce, Rockford, Ill.) at 37 C for 1 h. LC10 YTE or mouse anti-His mAb at 2 µg/ml (R&D Systems, Minneapolis, Minn.) was added to the wells and incubated for 1 h at RT. Plates were then washed six times with PBS/0.05% Tween 20. Bound LC10 YTE or mouse anti-His mAb was detected using an anti-human or anti-mouse IgG HRP conjugates (Jackson ImmunoResearch laboratories, Inc. West Grove, Pa.), respectively.

Generation of Chimeric Variants Between Alpha Toxin and LukF-PV

Chimeric variants composed of portions of alpha toxin and LukF-PV were generated to identify the binding region of LC10 YTE on alpha toxin. DNA constructs of six alpha toxin chimeric variants encoding LukF-PV regions at aa 1-51, aa 52-110, aa 111-147, aa 148-205, aa 204-241, or aa 248-293 were generated by gene synthesis. DNA constructs encoding for the other chimeric variants were created by overlapping extension PCR using a pET3d plasmid encoding alpha toxin or LukF-PV (in-house plasmids) as templates. All DNA constructs were then cloned into the pET3d bacterial expression vector (EMD Chemicals Inc, Philadelphia, Pa.) and transformed into *E. coli* strain BL21 (DE3) (Invitrogen, Carlsbad, Calif.). The transformed BL21 (DE3) cells were grown in MagicMedia *E. coli* expression medium (Invitrogen, Carlsbad, Calif.) to express the variant proteins using standard protocols.

Characterization of the Binding Characteristics of LC10 YTE to Chimeric Variants Using ProteOn The binding characteristics of LC10 YTE to alpha toxin/LukF-PV chimeric variants were studied using a ProteOn XPR36 instrument (BioRad, Hercules, Calif.). Standard amine coupling was used to immobilize an anti-alpha toxin polyclonal antibody (In house generated antibody) in 10 mM sodium acetate [pH 5.0] to the surface of a GLC biosensor chip at about 5000 resonance units (RU) for each channel. The alpha toxin/LukF-PV chimeric proteins in bacterial lysate supernatant were injected onto the immobilized GLC surface so as to obtain a capture response of about 200RU, Untransformed bacterial lysate supernatant was also injected under the same conditions as a reference channel. LC10 YTE samples were prepared in phosphate-buffered saline (PBS) (pH 7.4), 0.005% Tween-20, and injected at 90 μL/min for 150 or 180 sec at concentrations typically ranging from 50 nM to 3.125 nM. 600 or 800 sec dissociation time were used. Expression levels of chimeric variants were also monitored following the injection of LC10 YTE as follows: anti-alpha toxin polyclonal antibodies were flowed at 90 µL/min for 150 or 180 sec at concentrations typically ranging from 50 nM to 3.125 nM with a 600 or 800 second dissociation time. The surface was regenerated twice by injecting glycine (10 mM, pH 1.5) at 100 µL/min for 30 sec. All sensorgram data were processed with the ProteOn Manager 3.0.1 software Example 2

Anti-Alpha Toxin mAb Generation

Anti-alpha toxin (AT) monoclonal antibodies (mAbs) were generated in VelocImmune mice which have been genetically engineered to contain an antibody repertoire with fully human variable regions fused to murine constant domain. The resulting antibodies are human:mouse chimeras which are easily converted to fully human IgG by genetically fusing the human variable domain from the chimeric mAb with the constant regions from a cloned human IgG-1. Mice were immunized with a nonhemolytic AT mutant ($AT_{H35L}$), described herein, and hybridomas were generated using standard methods. Initially, greater than 1800 hybridoma supernatants were found to contain IgG that bound recombinant AT (rAT-his) by antigen ELISA. The hybridoma supernatants which exhibited binding to rAT-his were then screened for activity by inhibition of rAT-his mediated lysis of rabbit red blood cells (RBC) in a hemolytic assay, whereby, the pool of functional mAbs was reduced to about 250. The hybridoma supernatants were then normalized for IgG levels and their inhibitory activities compared. Thirteen of the most potent rAT-his inhibitors were selected for limited dilution cloning and utilized for small-scale IgG expression and purification. Following screening of these clones and subsequent biochemical and in vivo characterization, as described below, VH and VL sequences were further optimized to generate additional antibodies, as listed below in Table 7.

Example 3

Inhibition of Cytolytic Activity

Figure 1B:
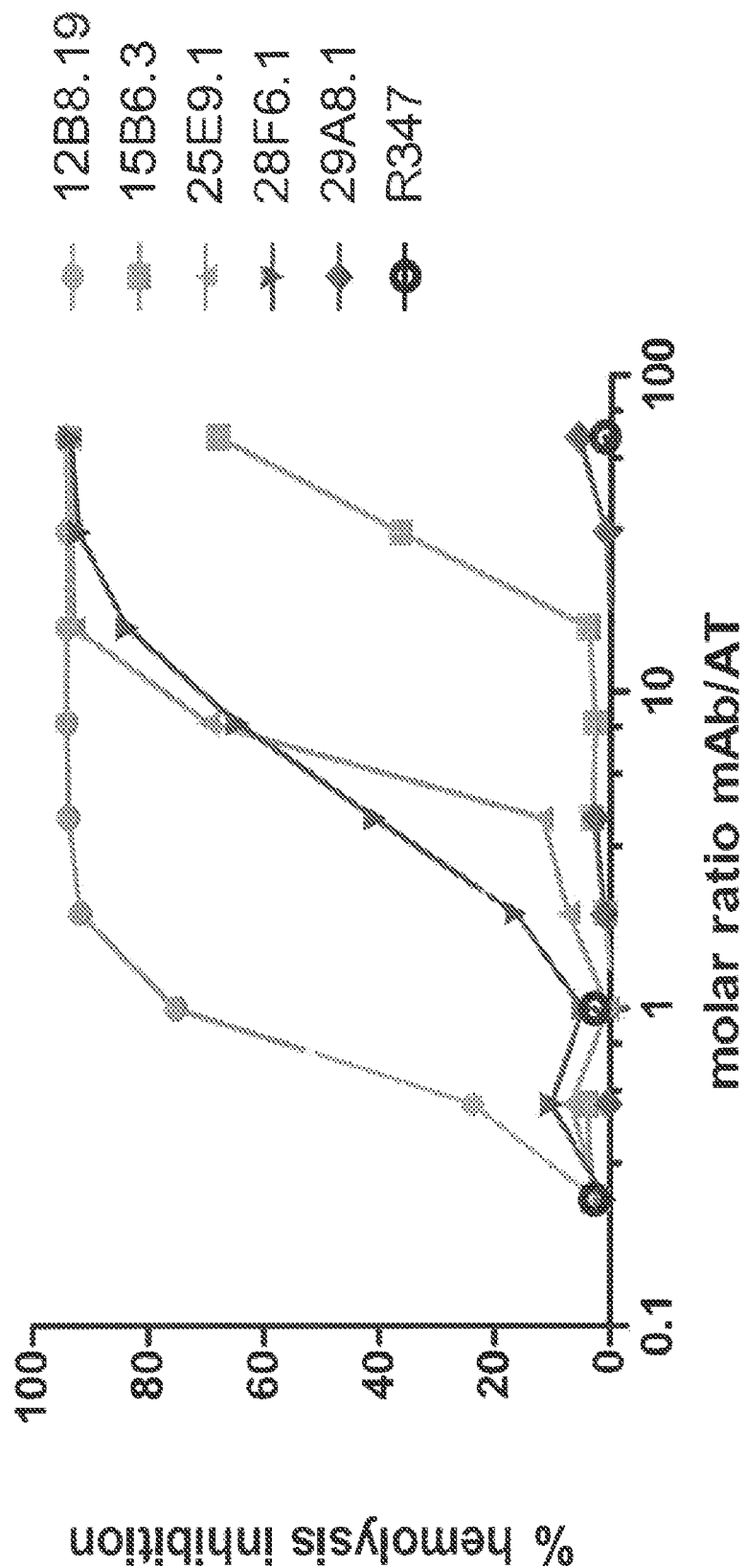

The inhibitory activities of the 13 purified anti-AT IgG were compared in a hemolytic assay. Purified anti-AT mAbs were titrated in a hemolytic assay in the presence of constant quantities of nAT and rabbit red blood cells. The mAbs were each titrated down from about 20 µg/mL in the presence of a constant amount of native AT (nAT) and rabbit red blood cells (RBC). Hemolysis was measured by the hemoglobin release into the supernatant. Percent (%) hemolysis inhibition was calculated as follows: % inhibition=100*[100−($A_{490}$ nAT+Ab)/($A_{490}$ nAT no Ab)]. Representative hemolytic assays demonstrating the thirteen most potent rAT-his inhibitors are shown in FIGS. 1A and 1B. A non-specific IgG control (R347) was included as a negative control.

Only 7 of the 13 purified mAbs (mAbs; 2A3.1, 10A7.5, 11D12.1, 12B8.19, 15B6.3, 25E9.1 and 28F6.1) inhibited nAT mediated RBC lysis (see FIGS. 1A and 1B). Three of the antibodies (2A31., 10A7.5 and 12B8.19) were potent inhibitors and exhibited about 80% inhibition of nAT mediated RBC lysis at a 1:1 (mole IgG:mole AT) ratio. These results suggested that the generated mAbs may inhibit pore formation in rabbit RBCs.

Figure 2A:
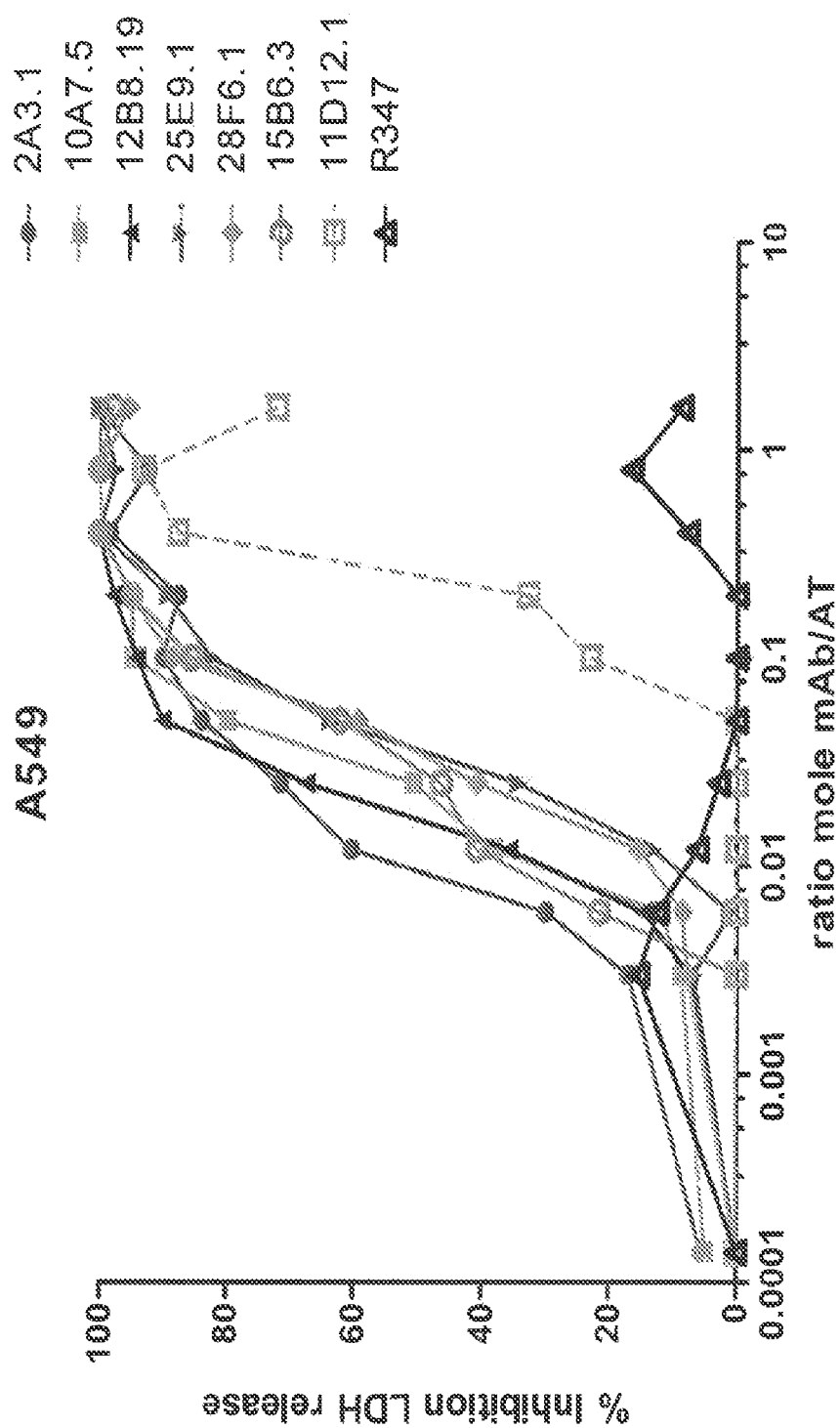
FIGS. 2A and 2B graphically illustrate the percent inhibition of human A549 and THP-1 cell lysis by anti-alpha toxin antibodies. Experimental details and results are described in Example 3.
Figure 2B:
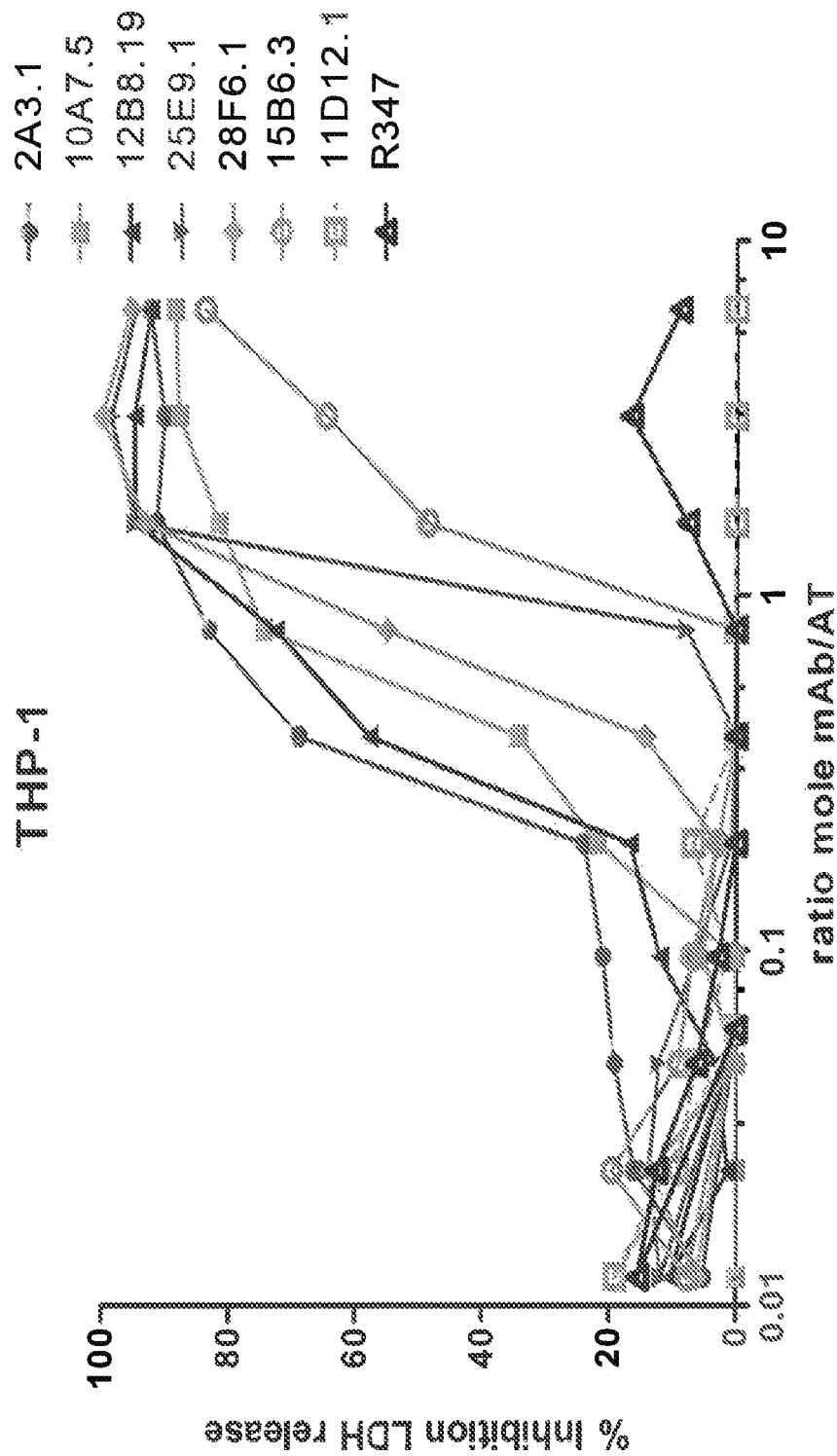

Human erythrocytes do not posses a large number of receptors for AT. Consequently, human RBC are not as sensitive as rabbit RBC to nAT mediated lysis and are likely not a primary target for AT during an infection. Other cell types (e.g., epithelial, lymphocytes, monocytes and macrophages) are more relevant targets for the effects of nAT during a staphylococcal infection. The activity of the purified antibodies was examined in the nAT mediated lysis of the human cell lines, A549 (alveolar epithelial cell line) and THP-1 (monocytic cell line). The monoclonal antibodies (mAbs) were titrated against a constant level of nAT in the presence of either A549 or THP-1 cells. Cell lysis was quantified by release of lactate dehydrogenase (LDH) and the % inhibition of LDH release determined, as described herein. The results are shown graphically in FIGS. 2A and 2B. The mAbs which inhibited rabbit RBC lysis also inhibited nAT mediated lysis of both human A549 and THP-1 cells (see FIGS. 2A and B, respectively) with the exception of 11D12.1 which inhibited lysis of A549 cells and had no effect on nAT mediated lysis of THP-1 cells. The potent anti-AT activity exhibited by these mAbs highlights the potential utility of these antibodies to inhibit AT activity during an infection, thereby limiting the progression of staphylococcal related symptoms and disease.

Example 4

Passive Immunization with Anti-AT mAbs Reduces Dermonecrotic Lesions

Figure 3B:
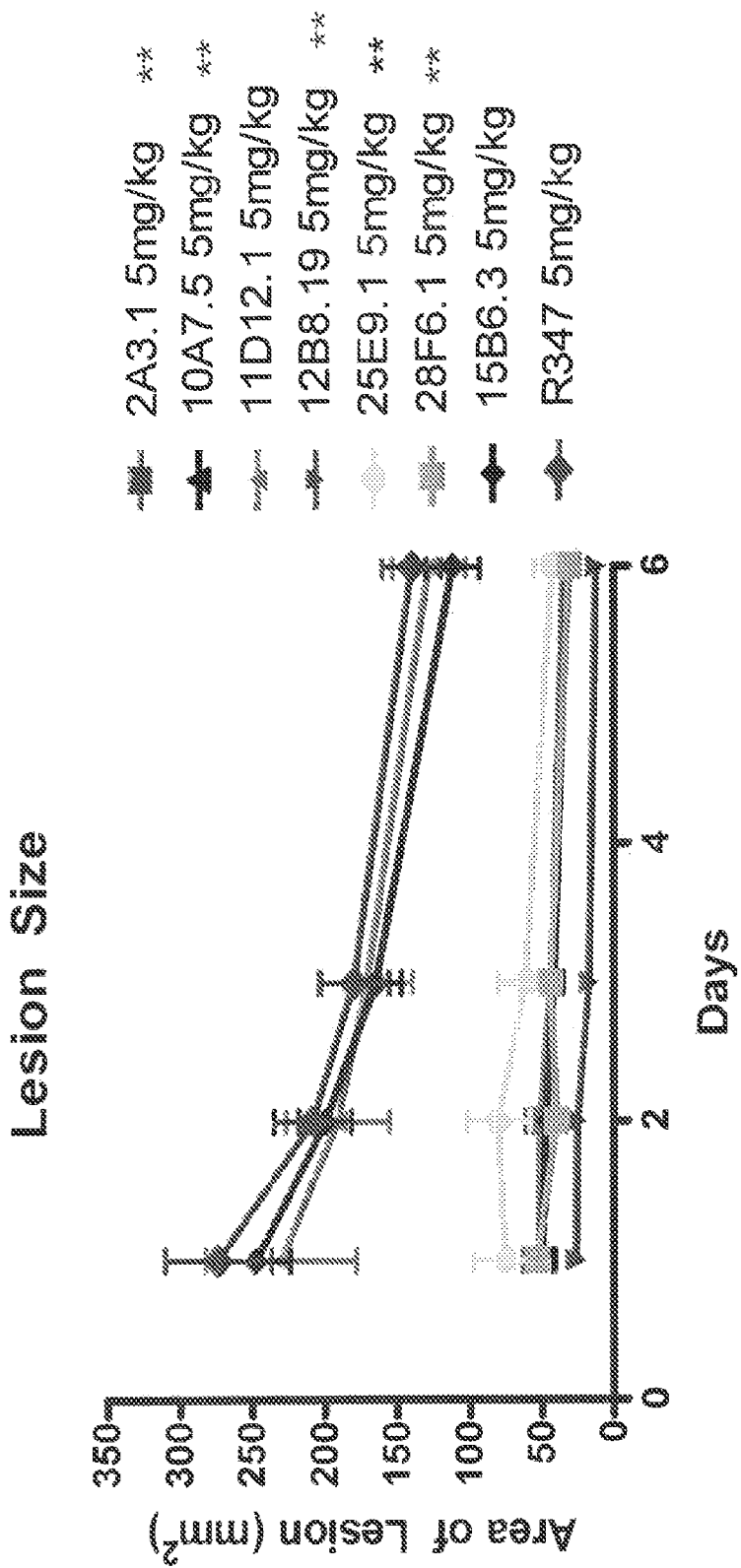
Figure 17:
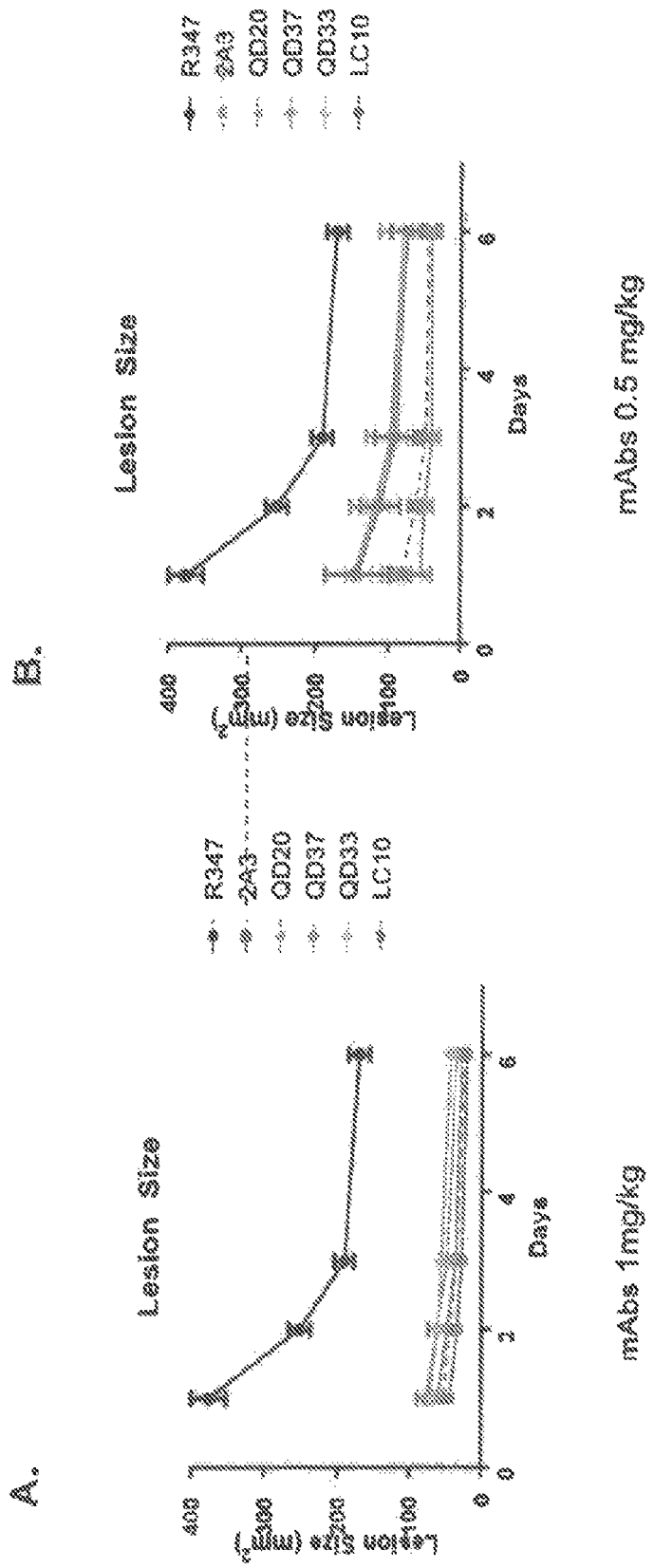
FIGS. 17A and 17B graphically illustrates the reduction in lesion size over the time course of infection after passive immunization with inhibitory anti-*S. aureus* alpha toxin mAbs QD20, QD37, LC10, QD33, 2A3 and the control R347 in a dermonecrosis model. Groups of 5 BALB/c mice were passively immunized with 1 mg/kg (FIG. 17A) and 0.5 mg/kg (FIG. 17B) of the inhibitory mAbs shown and then infected with *S. aureus* Wood and lesion size monitored for 6 days.

S. aureus is a leading cause of skin and soft tissue infections (SSTI) both in the hospital and the community which are oftentimes characterized by inflammation, tissue damage and pus formation. AT may play a role in these infections leading to a hyper inflammatory response and tissue damage and inhibition of AT function would then limit the ability of the bacteria to cause serious disease. To determine the usefulness of the anti-AT mAbs in minimizing, reducing or eliminating the effects of S. aureus infection, groups of 5 mice were injected intraperitoneally (IP) with each of the 7 inhibitory mAbs (e.g., about 5 mg/kg) and an IgG-1 isotype control (R347) control 24 hrs prior to subcutaneous infection with S. aureus Wood. The size of the dermonecrotic lesions were measured daily for 6 days and documented photographically, as shown in FIG. 3A (day 6 shown in FIG. 3A). The 5 most potent in vitro inhibitors of nAT function (2A3.1, 10A7.5, 12B8.19, 25E9.1 and 28F6.1), substantially reduced the lesion size relative to the R347 control whereas the least potent mAbs, in vitro (11D12.1, 15B6.3), did not have a substantial effect on lesion size relative to the control, as shown in FIGS. 3A and 3B. FIG. 3B graphically illustrates the decrease in lesion size over time. 2A3.1, 10A7.5, 12B8.19, 25E9.1 and 28F6.1 are potent inhibitors of AT function in vitro and also exhibit a potent prophylactic effect in a murine model of SSTI. Additional antibodies, LC10, QD20, QD33, and QD37 were also tested in the dermonecrosis model. These monoclonal antibodies were injected intraperitoneally (IP) into five mice per group at 1 and 0.5 mg/kg 24 hours prior to subcutaneous infection with S. aureus Wood as described above. Results are shown in FIGS. 17 A and B.). P-values were calculated using Dunnett's post-test. For the 1 mg/kg experiments, the p-value for the R347 control as compared to the test Abs was p<0.0001. For the 0.5 mg/kg experiments, the p-value for the R347 control as compared to the test Abs was p<0.05.

Example 5

Passive Immunization with Anti-AT mAbs Enhance Survival in Murine Pneumonia

Figure 4:
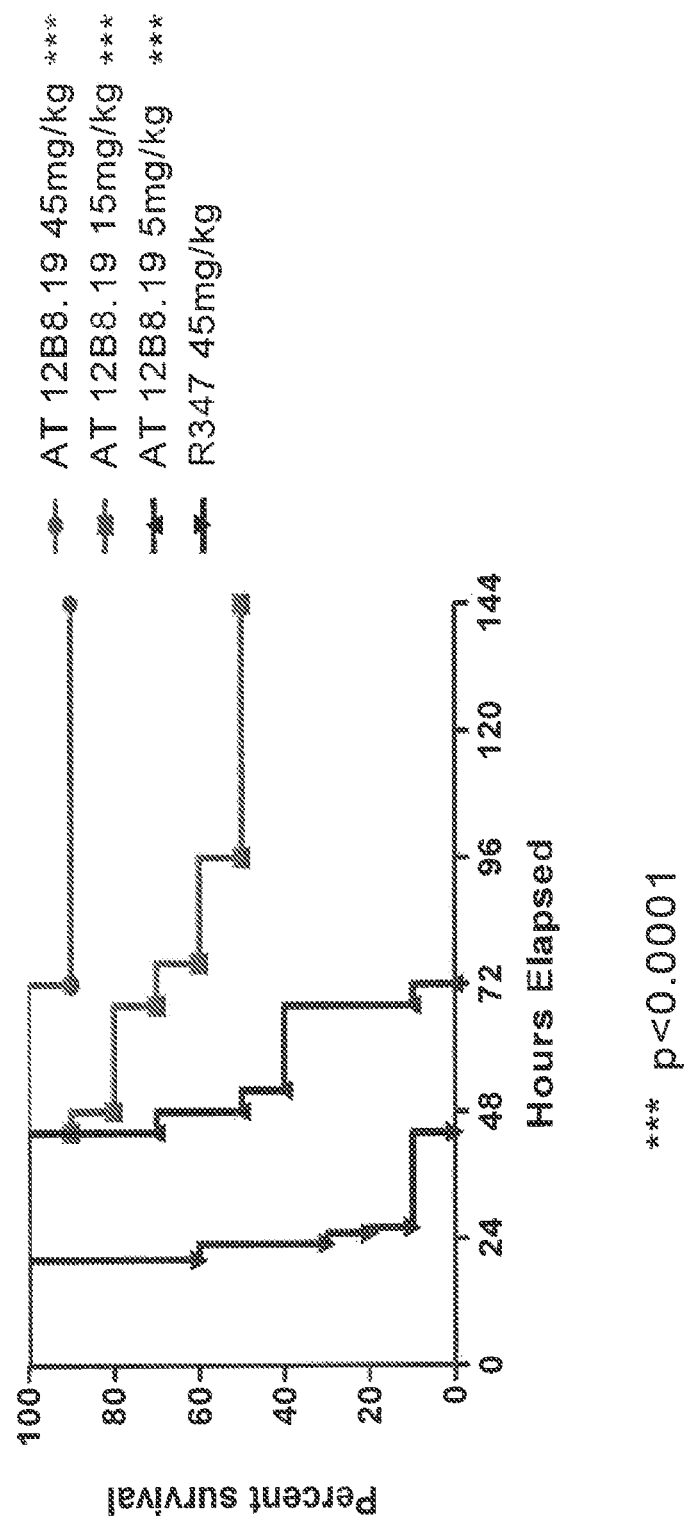
FIGS. 4-7 graphically illustrate the survival of mice passively immunized with various mAbs described herein in a pneumonia model.
Figure 5:
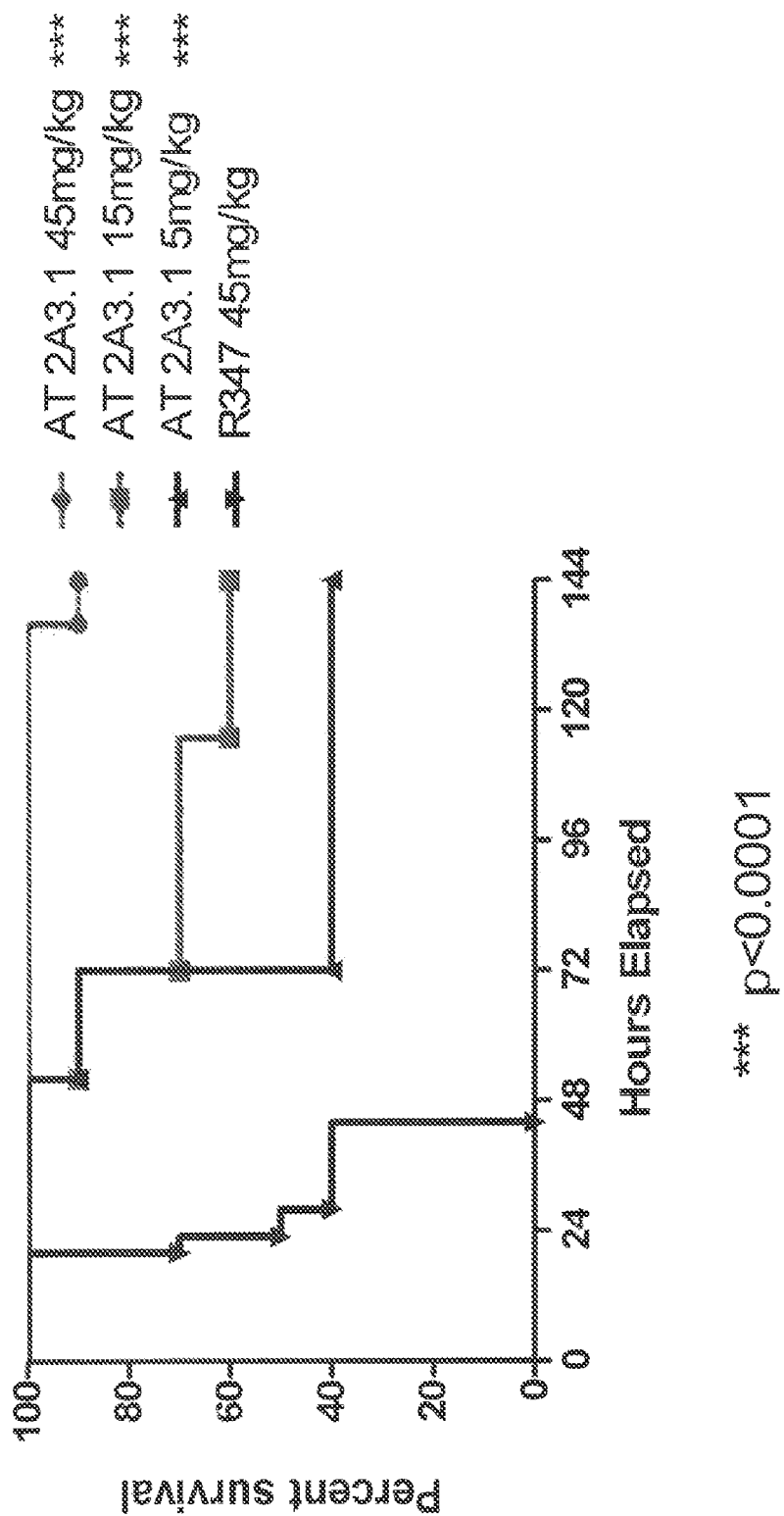
Figure 6:
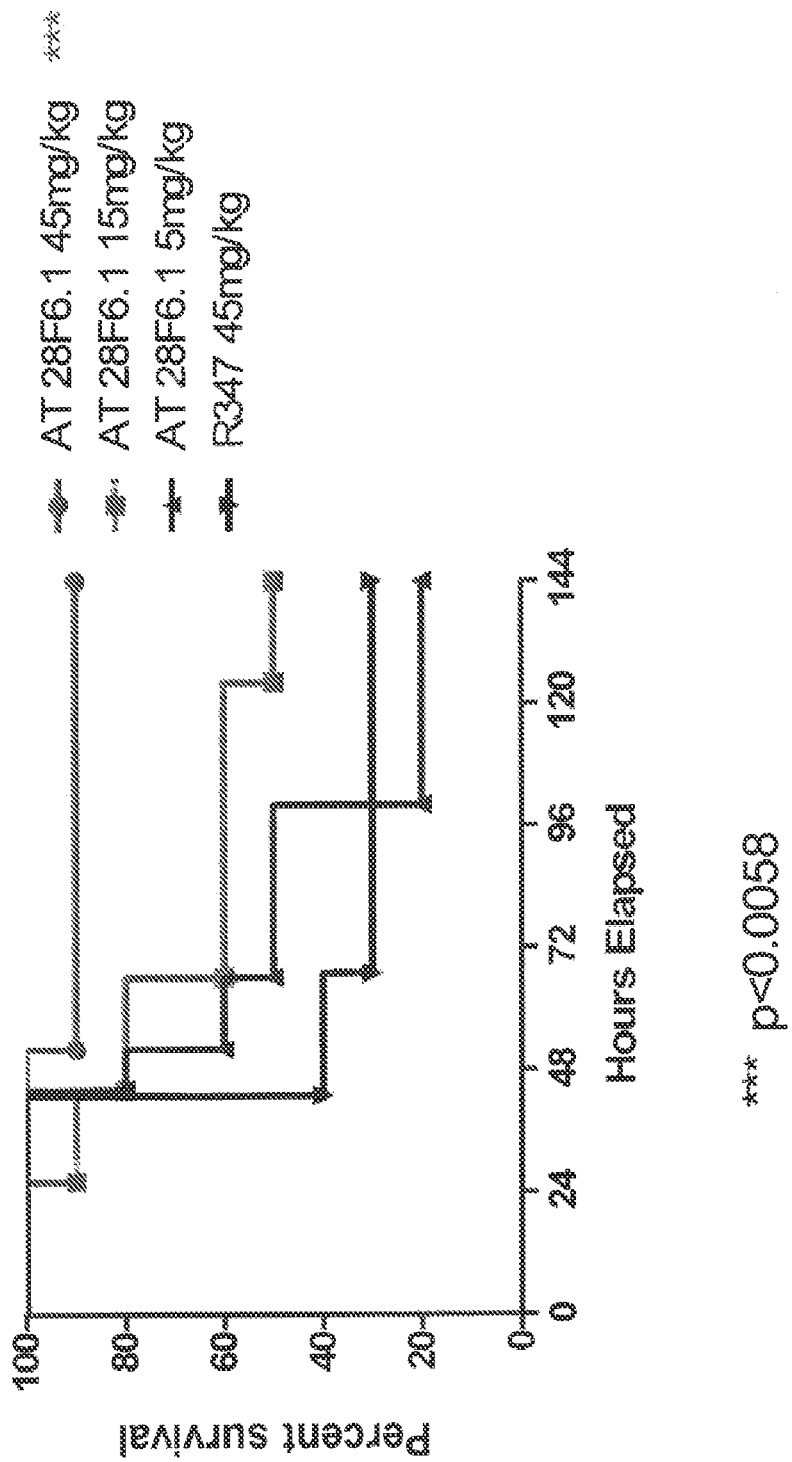
Figure 7:
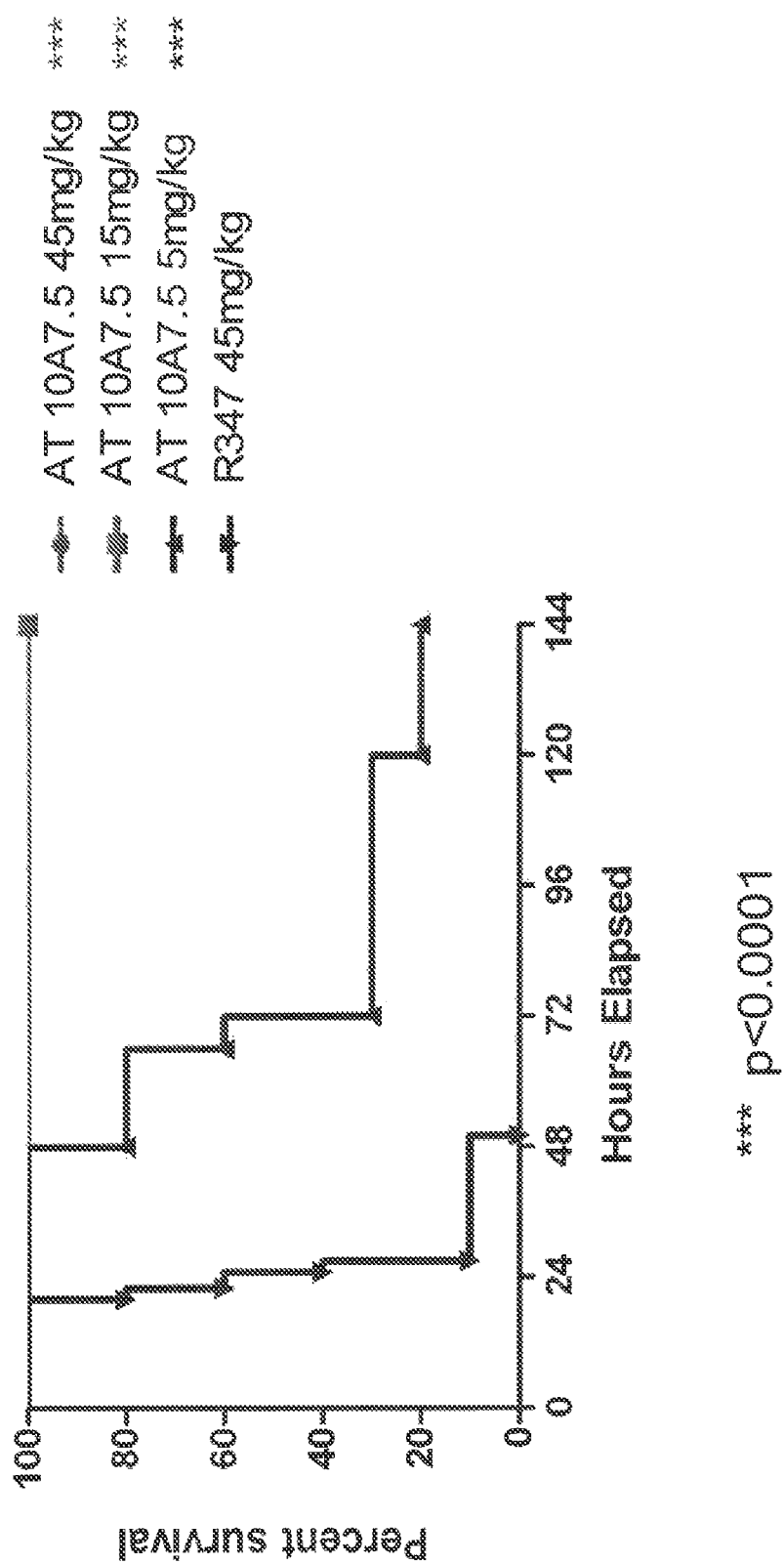

Prophylaxis with the most potent anti-AT mAbs generated was tested in a murine pneumonia model. C57BL/6J mice were passively immunized with about 5 mg/kg, about 15 mg/kg, and about 45 mg/kg of 2A3.1, 10A7.5, 12B8.19 or 28F6.1, twenty-four hours prior to intranasal infection with *S. aureus* USA300 (BAA-1556). Survival was then monitored for 6 days and compared with an isotype control (R347) at 45 mg/kg, as shown in FIGS. 4-7. Statistical significance was calculated using the log-rank test. FIG. 4 graphically illustrates the percent survival over the course of the *S. aureus* infection after passive immunization with various amounts of mAB 12B.19. FIG. 5 graphically illustrates the percent survival over the course of the *S. aureus* infection after passive immunization with various amounts mAB 2A3.1. FIG. 6 graphically illustrates the percent survival over the course of the *S. aureus* infection after passive immunization with various amounts mAB 28F6.1. FIG. 7 graphically illustrates the percent survival over the course of the *S. aureus* infection after passive immunization with various amounts mAB 10A7.5.

All anti-AT antibodies shown resulted in a significant improvement in survival relative to the control, leading to at least 90% survival at the 45 mg/kg dose (see FIGS. 4-7). Alpha toxin is believed to be a key virulence determinant in staphylococcal pneumonia. The results presented herein illustrate that passive administration of potent inhibitory mAbs is a valid approach for disease prevention. Taken together, the animal studies presented herein support a role for AT in staphylococcal disease and provide support for the use of mAbs which inhibit AT function to limit disease severity or even death associated with a *S. aureus* infection.

Figure 8A:
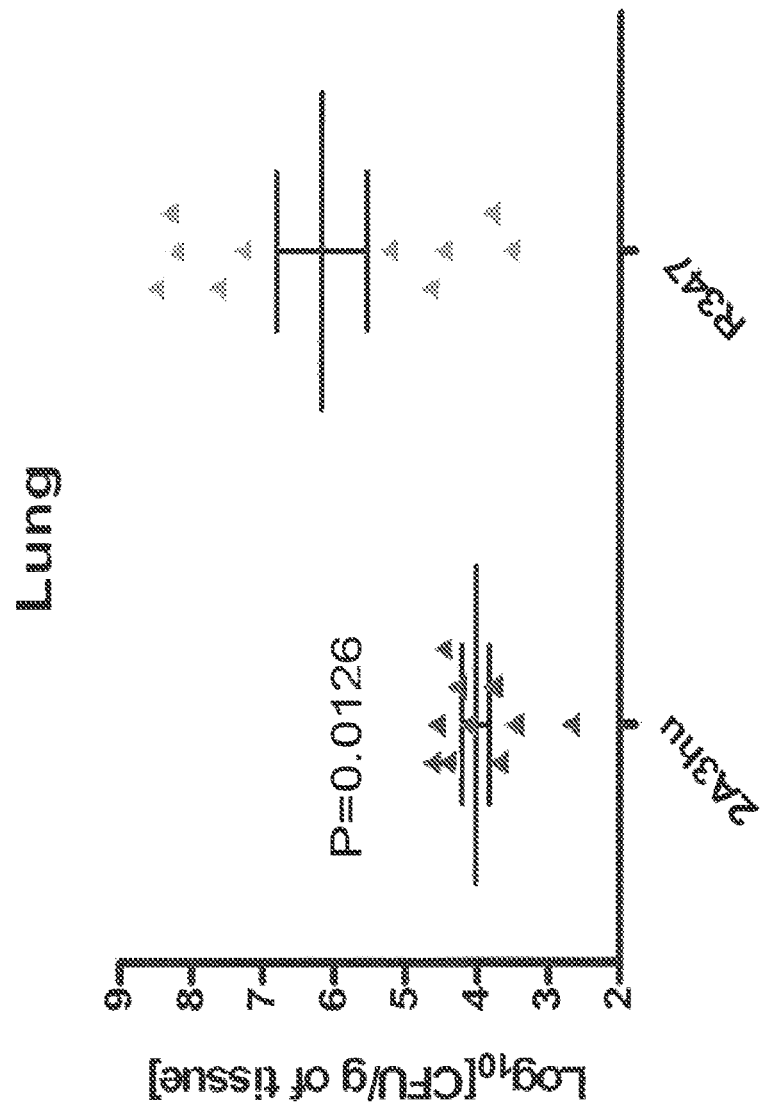
FIGS. 8A and 8B graphically illustrate the distribution of bacteria in lung (FIG. 8A) and kidney (FIG. 8B) in mice passively immunized with a fully human version of mAb 2A3.1 (e.g., 2A3hu) or an isotype control (R347). C57BL/6J mice were passively immunized with 2A3hu (15 mg/kg) 24 hr prior to infection with USA300. Samples also were collected to measure cytokine levels and for histopathological analysis. Experimental details and results are described in Example 5.
Figure 8B:
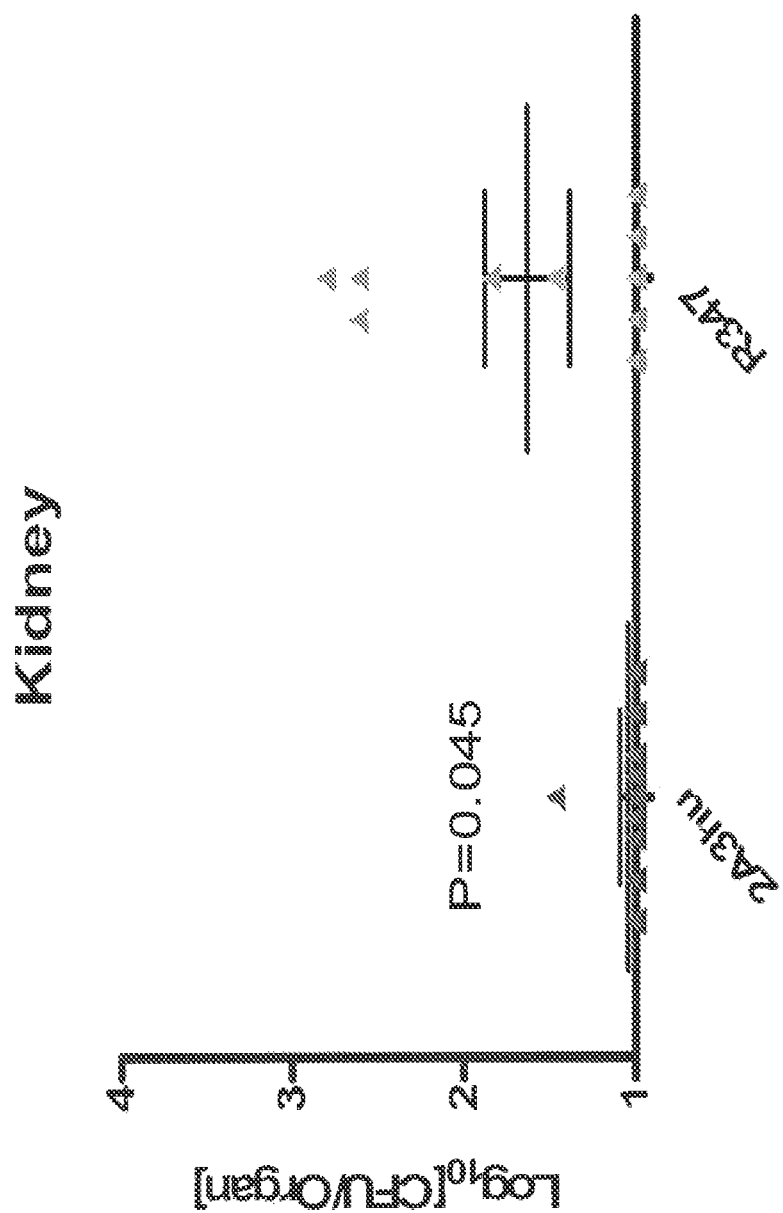

To further characterize the impact of an anti-AT mAb on bacterial numbers during an infection, a fully human version of mAb 2A3.1 (e.g., 2A3hu) was delivered prophylactically to mice 24 hr before intranasal infection with approximately $1.3 \times 10^8$ cfu of *S. aureus* USA300. Forty-eight hours post infection, the mice were euthanized and their lungs and kidney were collected and processed for bacterial enumeration (see FIGS. 8A and 8B). 4 and 24 hours post infection, mice were euthanized and samples taken to measure cytokine production (described below and see FIG. 9) and for histopathological analysis (described below and see FIG. 10). P-values were calculated using Dunnett's post-test. Representative results of bacterial enumeration are presented in FIGS. 8A and 8B. Prophylactic administration of 2A3hu resulted in a significant reduction in bacterial numbers in both the lungs (see FIG. 8A) and kidneys (see FIG. 8B) relative to the R347 control, indicating that the inhibition of AT function may limit disease progression, enhance clearance and also limit systemic spread of the invading organism.

Figure 18:
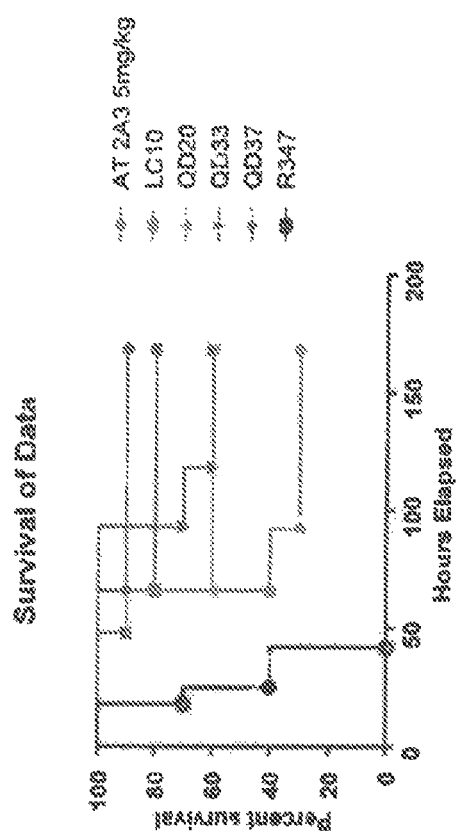
FIG. 18 graphically illustrates the survival of mice passively immunized with the mAbs QD20, QD37, LC10, QD33, 2A3 and the control R347 in a pneumonia model. Mice were passively immunized with 5 mg/kg purified mAb 24-hours prior to infection with *S. aureus* USA300 (~$2 \times 10^8$ cfu).

Additional antibodies, LC10, QD20, QD33, and QD37 were also tested in the pneumonia model. These monoclonal antibodies were injected intraperitoneally (IP) in ten mice per group at 5 mg/kg 24 hours prior to intranasal (IN) infection with approximately $2 \times 10^8$ cfu of *S. aureus* USA300. The results of these experiments are shown in FIG. 18. P-values were calculated using Dunnett's post-test. The p-value for the 2A3 mAb as compared to QD37 was p=0.0072; the p-value for the 2A3 mAb as compared to LC10 was p=0.0523; the p-value for the 2A3 mAb as compared to QD33 was p=0.0521.

Example 6

Inhibition of AT in the Pneumonia Model Reduces Proinflammatory Cytokine Production

*S. aureus* pneumonia infection typically is accompanied by an overproduction of proinflammatory cytokines thought to lead to increased immune cell activation and infiltration, ultimately leading to increased congestion and tissue necrosis (Bubeck Wardenburg, J. 2007). An *S. aureus* AT deletion mutant has been shown to exhibit reduced virulence relative to its isogenic wild-type *S. aureus* in the murine pneumonia model. It was further demonstrated that active and passive immunization against AT reduced the expression of IL-1β, a known mediator of acute lung injury, and protected mice from severe pneumonia (Bubeck Wardenburg, J. 2007; Bubeck Wardenburg, J. 2008). These results suggest that inhibiting AT during *S. aureus* infection may reduce the production of proinflammatory cytokines and thus limit excessive cellular infiltration with the end result being fewer symptoms of pneumonia and enhanced bacterial clearance as seen above.

Figure 9:
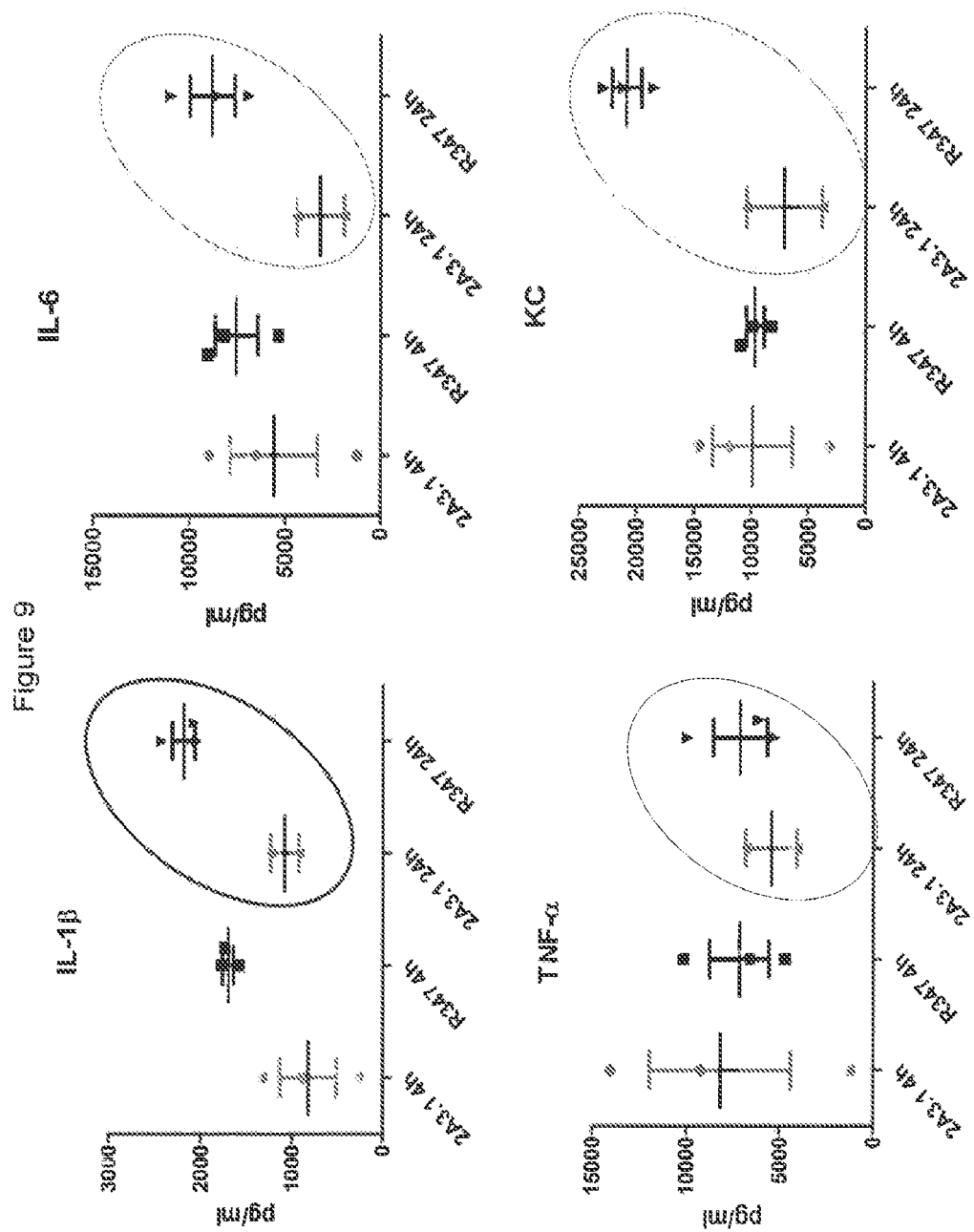
FIG. 9 graphically illustrates the reduction in inflammatory cytokine production following passive immunization with mAb 2A3hu. Circled results are from the 24 hour time point. Experimental details and results are described in Example 6.
Figure 10:
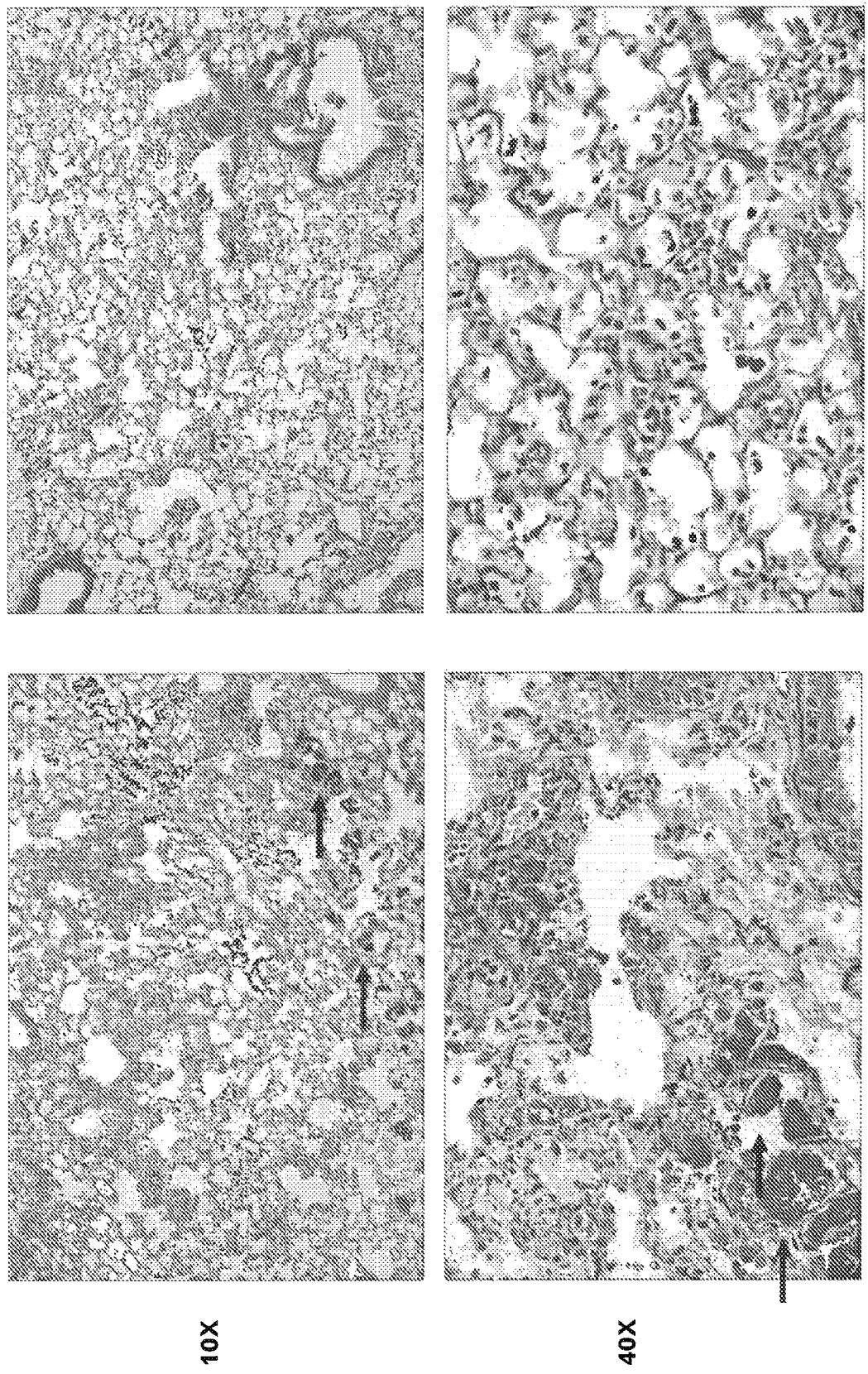
FIG. 10 shows representative photographs of lung histology in mice treated with the R347 control (see top and bottom photographs on left of FIG. 10) or treated with 2A3hu (see top and bottom photographs on right of FIG. 10). Experimental details and results are described in Example 6.

To test this hypothesis, mice were passively immunized with 2A3hu 24 hrs before intranasal infection with approximately $1.3 \times 10^8$ cfu of *S. aureus* USA300. Four and twenty-four hrs post infection the mice were euthanized and half the lung was fixed and prepared for haematoxylin and eosin staining and microscopic examination while bronchoalveolar lavage fluid was collected from the other side and processed to determine cytokine levels. Representative results of cytokine production after passive immunization are shown in FIG. 9. FIG. 10 photographically illustrates the effectiveness of passive immunization with mAbs described herein.

Four hours post infection cytokine levels were similar in R347 and 2A3hu treated mice, however by 24 hrs post infection the levels of IL-6, TNF-α, KC and IL-1β were all reduced in the 2A3hu treated animals, as shown in FIG. 9 (see circled results at 24 hours time point), indicating that prophylactic administration of 2A3hu resulted in reduced levels of cytokines detected, with respect to the control. These data are supported by results from the histopathological examination of the lung in which the R347 treated mice had prominent pulmonary inflammation, necrosis and alveolitis along with the presence of bacterial colonies (see top left and bottom left pictures in FIG. 10). In contrast, the 2A3hu treated animals had limited pulmonary inflammation with no necrosis, alveolitis or bacterial colonies visible (see top right and bottom right pictures in FIG. 10). The protective effect of the anti-AT mAbs in the pneumonia model is associated with a reduced inflammatory response which can limit local tissue damage and promote bacterial clearance.

Example 7

Binding Kinetics and Competition

Affinity measurements were carried out using surface plasmon resonance (SPR), to further characterize the mAbs that exhibited potent inhibitory activity. Purified IgG was captured on a sensor using rat anti-mouse IgG and the chip was exposed to solutions having different concentrations of nAT. Association and dissociation rate constants were measured, from which binding constants were determined. Antibodies 2A3.1, 10A7.5, 25E9.1 and 12B8.19 had similar affinities with $K_D$ values of 601, 504, 337 and 485 pM respectively, whereas 28F6.1 exhibited a $K_D$ value of 13 nM, as shown in the table below. $K_D$ was calculated as $k_{off}/k_{on}$.

| IgG | $k_{on}$ (1/Ms) (xe + 5) | $k_{off}$ (1/s) (xe − 4) | $K_D$ (nM) | Chi$^2$ |
|---|---|---|---|---|
| 2A3.1 | 13.7 | 8.21 | 0.601 | 0.433 |
| 10A7.5 | 6.92 | 3.49 | 0.504 | 0.345 |
| 12B8.19 | 5.75 | 2.78 | 0.485 | 0.288 |
| 25E9.1 | 6.24 | 2.1 | 0.337 | 0.291 |
| 28F6.1 | 0.67 | 8.81 | 13.1 | 0.906 |

Competition experiments also were conducted using SPR, the results of which suggest that antibodies 2A3.1, 10A7.5, 25E9.1 and 12B8.19 likely bind the same or similar epitope.

$IC_{50}$ and $K_d$ value are shown for mAbs QD20, LC10, QD33, QD37 and 2A3GL below

| Ab | $IC_{50}$ (µg/ml) | Kd (nM) |
|---|---|---|
| QD20 | 0.16 | 0.087 |
| LC10 | 0.12 | 0.17 |
| QD33 | 0.09 | 0.33 |
| QD37 | 0.17 | 0.18 |
| 2A3GL | 0.48 | 1.44 |

The $IC_{50}$ was calculated using the RBC hemolytic assay with S. aureus alpha toxin at 0.1 mg/ml Example 8

Inhibitory mAbs Block Formation of SDS-Resistant Heptamer

Figure 11:
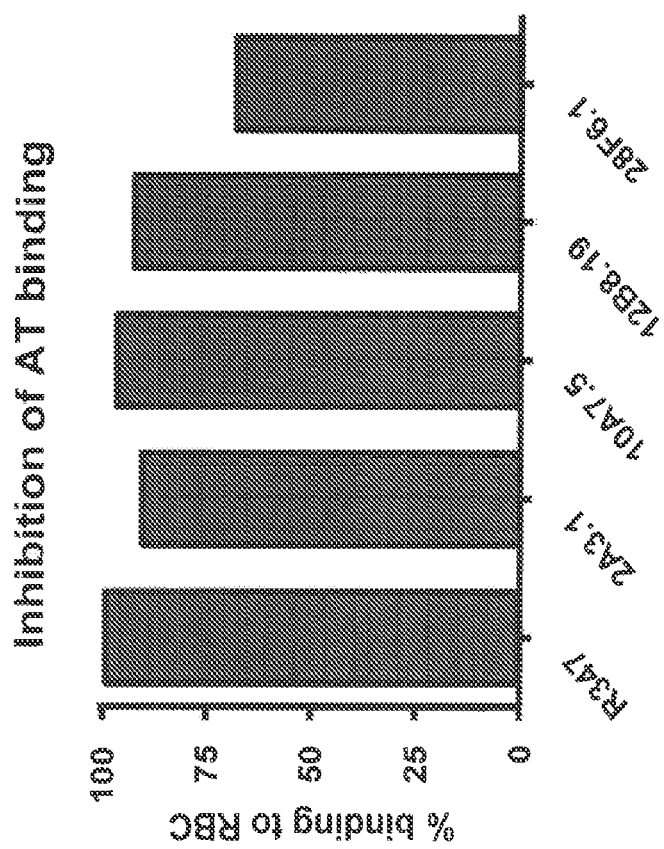
FIG. 11 graphically illustrates that anti-AT (*S. aureus* alpha toxin) mAbs described herein do not inhibit native alpha toxin (nAT) binding to receptors present on rabbit erythrocyte ghosts. Experimental details and results are described in Example 8.

S. aureus alpha toxin (AT) is believed to lyse cells in a multistep process in which a secreted soluble monomeric AT molecule binds to a cell surface receptor, or non-specifically adsorbs to cell membranes, oligomerizes into a heptameric pre-pore on the cell surface and undergoes a conformational change leading to formation of a 14-stranded transmembrane β-barrel that mediates subsequent target cell lysis. The mechanism of inhibition by the mAbs described herein was further characterized to determine at which step the inhibitory mAbs blocked AT function. The ability of these mAbs to prevent binding of AT to rabbit RBC ghosts attached to a 96-well tissue culture plate was examined. 96-well ELISA plates were coated with RBC ghosts and blocked with 2% BSA. The ghosts were then incubated with nAT+/−a 20 molar excess of anti-AT IgG. Binding of nAT was then detected with rabbit anti-AT IgG and % binding calculated; % binding=100×[100−($A_{490}$ nAT+mAb)/($A_{490}$ nAT no mAb)]. At a 20 molar IgG excess, there was no inhibition of nAT binding to rabbit RBC membranes, as shown in FIG. 11, indicating that these inhibitory mAbs were not acting at the step of receptor binding.

Figure 12:
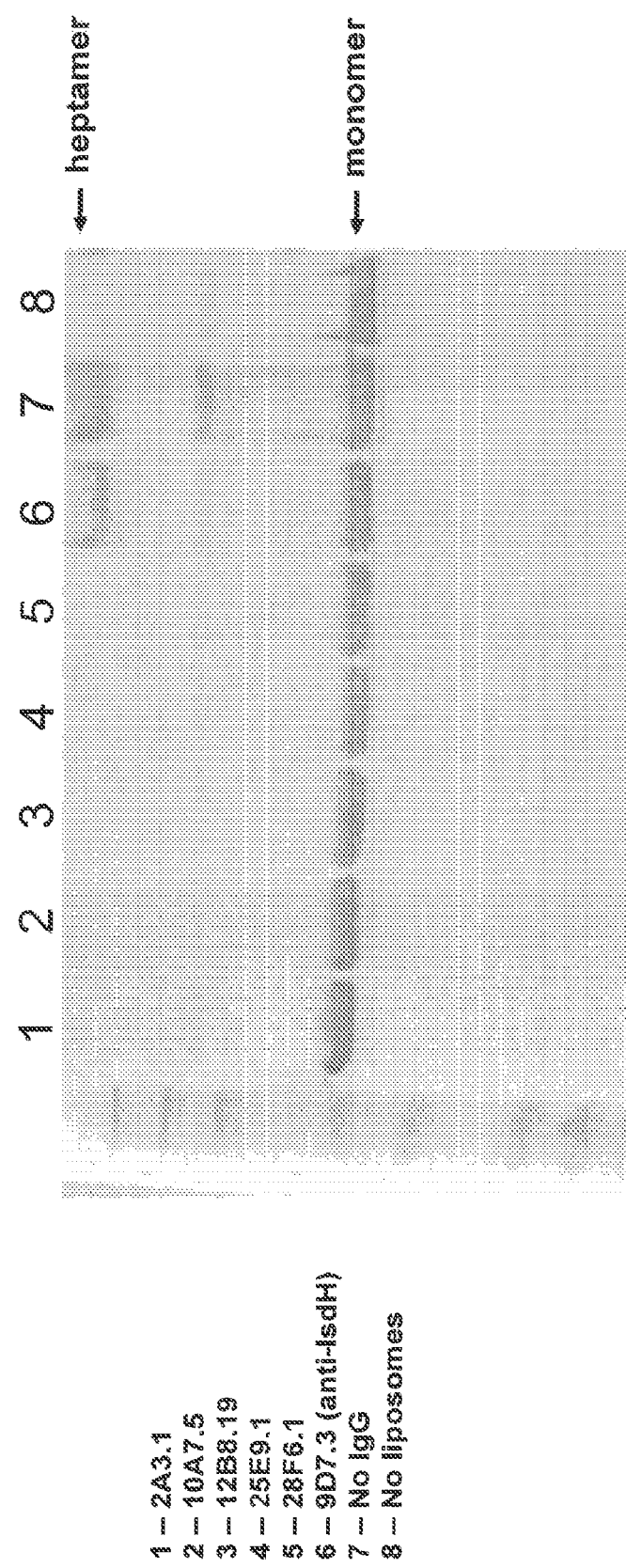
FIG. 12 is a representative western blot illustrating inhibition of heptamer formation by antibodies described herein. Experimental details and results are described in Example 8.
Figures 13A, 13B:
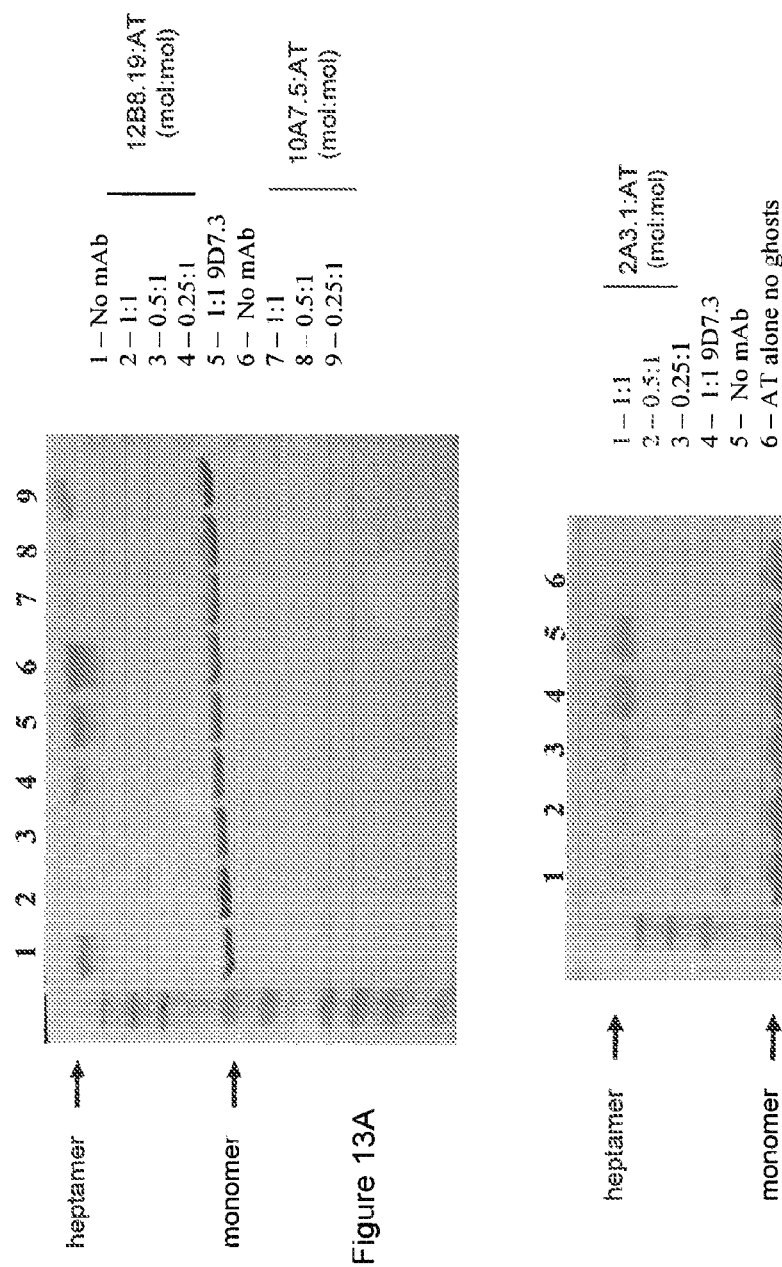
FIGS. 13A and 13B illustrate representative western blots confirming the inhibition of oligomerization by the anti-AT mAbs described herein, and further illustrates that the inhibition can be titrated. Experimental details and results are described in Example 8.

In addition to cell membranes, AT and other pore-forming toxins have been shown to readily assemble and form pores in liposome membranes. Initially, the effect of anti-AT IgG on AT heptamer formation was tested on liposomes. Following incubation of AT with a 10-fold molar excess of liposomes (lipid:AT, wt:wt), in the presence of IgG, heptamer formation was examined by western blot analysis, as shown in FIG. 12. The samples were then solubilized in SDS-PAGE sample buffer at 37 C and heptamer formation was detected by western blot analysis. Presence of the SDS-resistant heptamer is readily apparent at the top of the gel shown in FIG. 12, in lanes 6 and 7 (e.g., mAb9D7.3 and no IgG control lane, respectively). All of the inhibitory mAbs ablated heptamer formation, whereas an irrelevant isotype control (e.g., Lane 6; 9D7.3) had no effect. The inhibition of oligomerization activity was confirmed using mAbs 2A3.1, 10A7.5 and 12B8.19 in an oligomerization assay on rabbit RBC ghosts, as illustrated in the representative western blots shown in FIGS. 13A and 13B. AT was incubated with a titration of IgG prior to incubation with rabbit erythrocyte ghosts and detection of heptamer formation by SDS-PAGE. mAbs 2A3.1, 10A7.5 and 12B8.19 effectively inhibited AT heptamer formation even at a 1:1 IgG:toxin ratio (mole:mole) and the oligomerization inhibition effect was titrated as the mAb levels were reduced (see FIGS. 13A and 13B; appearance of heptamer at molar ratios of 0.5:1 and 0.25:1). These results suggest that mAbs 2A3.1, 10A7.5 and 12B8.19 prevent AT mediated cell lysis through inhibition of SDS-resistant heptamer formation.

Example 9

Conversion to Fully Human IgG

Figure 14:
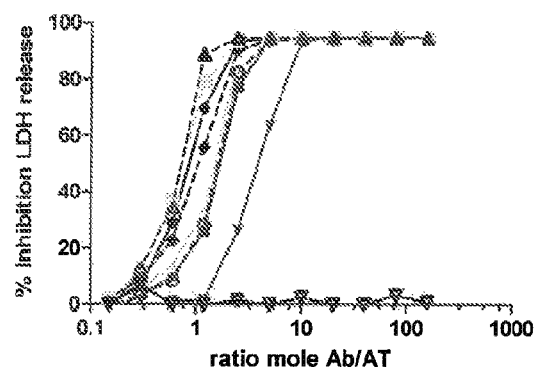
FIGS. 14-16, graphically illustrated the potency of fully human anti-AT antibodies in cell lysis inhibition assays. Fully human versions of the anti-AT IgG antibodies exhibit potency similar to the corresponding chimeric anti-AT IgG antibodies. The inhibitory activity of the fully human IgG antibodies were compared with the chimeric IgG antibodies in rabbit RBC (red blood cell) lysis (FIG. 14), A549 cell lysis (FIG. 15) and THP-1 cell lysis (FIG. 16). Experimental details and results are described in Example 9.
Figure 15:
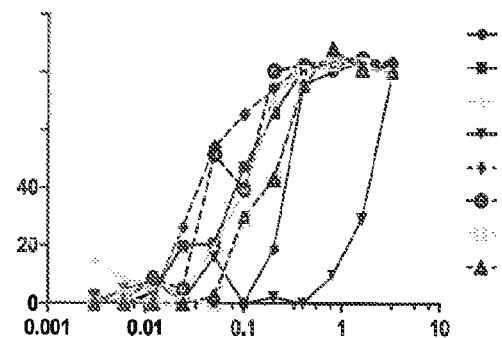
Figure 16:
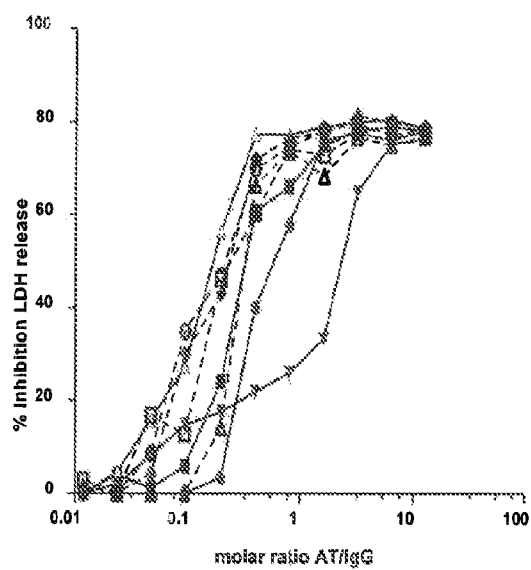

A fully human IgG includes the variable domains of the heavy ($V_H$) and light ($V_L$) chains from the chimeric mAbs described herein, genetically fused to the constant domains of a human IgG-1. The $V_H$ and $V_L$ from each of the chimeric mAbs were cloned, sequenced and fused to human IgG-1 $V_H$ and human kappa constant domains, respectively. The resultant fully human IgG-1s were shown to retain the human variable region responsible and the binding properties of the mAb of interest. The fully human antibodies were expressed, purified and their activity compared with the chimeric mAbs isolated from the VelocImmune mouse hybridomas. The fully human mAbs exhibited similar potency to the original chimeras in inhibition of RBC, A549 and THP-1 cell lysis, with the exception of 25E9.1hu, which became substantially more potent than the original 25E9.1 chimera. FIGS. 14-16 graphically illustrate the inhibition of LDH release, characteristic of cell lysis, in red blood cells (RBC; see FIG. 14), A549 cells (see FIG. 15) and THP-1 cells (see FIG. 16). The increase in potency of the human 25E9.1 mAb (e.g., 25E9.1hu) may have resulted from a mixed cell population in the original hybridoma which contained 2 distinct anti-AT IgG molecules, only one of which may have possessed the activity that inhibited nAT function. Therefore, molarity calculations and activity measurements for the original chimera mAb may not have a direct correlation.

Example 10

Representative Amino Acid and Nucleotide Sequences for Antibodies that Specifically Bind to S. aureus Alpha Toxin

TABLE 1

VL CDR sequences for mAbs 2A3.1, 10A7.5, 12B8.19 and 25E9.1

| SEQ ID NO: | Description | Sequence |
|---|---|---|
| SEQ ID NO: 1 | VL CDR1 | RASQSISSWLA |
| SEQ ID NO: 2 | VL CDR2 | KASSLES |
| SEQ ID NO: 3 | VL CDR3 | QQYNSYWT |

TABLE 2

VL CDR sequences for mAB 28F6.1

| SEQ ID NO: | Description | Sequence |
|---|---|---|
| SEQ ID NO: 4 | mAb 28F6.1 VL CDR1 | RASQGIRNDLG |
| SEQ ID NO: 5 | mAb 28F6.1 VL CDR2 | DASSLQS |
| SEQ ID NO: 6 | mAb 28F6.1 VL CDR3 | LQDYNYPWT |

TABLE 3

VH CDR sequences for mAb 2A3.1

| SEQ ID NO: | Description | Sequence |
|---|---|---|
| SEQ ID NO: 7 | VH CDR1 | SYDMH |
| SEQ ID NO: 8 | VH CDR2 | GIGTAGDTYYPGSVKG |
| SEQ ID NO: 9 | VH CDR3 | DNYSSTGGYYGMDV |

TABLE 4

VH CDR sequences for mAbs 10A7.5 and 12B8.19

| SEQ ID NO: | Description | Sequence |
|---|---|---|
| SEQ ID NO: 10 | VH CDR1 | RYDMH |
| SEQ ID NO: 11 | VH CDR2 | VIGTDGDTYYPGSVKG |
| SEQ ID NO: 12 | VH CDR3 | DRYSSSNHYNGMDV |

TABLE 5

VH CDR sequences for mAb 28F6.1

| SEQ ID NO: | Description | Sequence |
|---|---|---|
| SEQ ID NO: 13 | mAb 28F6.1 VH CDR1 | SYAMT |
| SEQ ID NO: 14 | mAb 28F6.1 VH CDR2 | VISGSGGSTYYADSVKG |
| SEQ ID NO: 15 | mAb 28F6.1 VH CDR3 | DGRQVEDYYYYGMDV |

TABLE 6

VH CDR sequences for mAb 25E9.1

| SEQ ID NO: | Description | Sequence |
|---|---|---|
| SEQ ID NO: 7 | mAb 25E9.1 VH CDR1 | SYDMH |
| SEQ ID NO: 17 | mAb 25E9.1 VH CDR2 | VIDTAGDTYYPGSVKG |
| SEQ ID NO: 18 | mAb 25E9.1 VH CDR3 | DRYSGNFHYNGMDV |

TABLE 7

VL and VH amino acid sequences for anti-alpha toxin mAbs

| Description | VH or VL sequence (with CDRs underlined) | CDR1 | CDR2 | CDR3 |
|---|---|---|---|---|
| mAb 2A3.1 VL | DIQMTQSPSTLSASVGDRVTIT CRASQSISSWLAWYQQKPGKA PKLLIYKASSLESGVPSRFSGSG SGTEFTLTISSLQPDDFATYYCQ QYNSYWTFGQGTKVEIK (SEQ ID NO: 19) | RASQSISS WLA (SEQ ID NO: 1) | KASSLES (SEQ ID NO: 2) | QQYNSYW T (SEQ ID NO: 3) |
| mAb 2A3.1 VH | EVQLVESGGGLVQPGGSLRLSC AASGFTFSSYDMHWVRQATGK GLEWVSGIGTAGDTYYPGSVK GRFTISRENAKNSLYLQLNSLR AGDTAVYFCARDNYSSTGGYY GMDVWGQGTTVTVSS (SEQ ID NO: 20) | SYDMH (SEQ ID NO: 7) | GIGTAGDT YYPGSVKG (SEQ ID NO: 8) | DNYSSTGG YYGMDV (SEQ ID NO: 9) |
| mAb 10A7.5 VL | DIQMTQSPSTLSASVGDRVTIT CRASQSISSWLAWYQQKPGKA PKLLIYKASSLESGVPSRFSGSG SGTEFTLTISSLQPDDFATYYCQ QYNSYWTFGQGTKVEIK (SEQ ID NO: 21) | RASQSISS WLA (SEQ ID NO: 1) | KASSLES (SEQ ID NO: 2) | QQYNSYW T (SEQ ID NO: 3) |
| mAb 10A7.5 VH | EVQLVESGGGLVQPGGSLRLSC AASGFTFSRYDMHWVRQATG KGLEWVSVIGTDGDTYYPGSV KGRFIISRENAKNSLYLEMNSL RAGDTAVYYCARDRYSSSNHY NGMDVWGQGTTVTVSS (SEQ ID NO: 22) | RYDMH (SEQ ID NO: 10) | VIGTDGDT YYPGSVKG (SEQ ID NO: 11) | DRYSSSNH YNGMDV (SEQ ID NO: 12) |
| mAb 12B8.19 VL | DIQMTQSPSTLSASVGDRVTIT CRASQSISSWLAWYQQKPGKA PKVLIYKASSLESGVPSRFSGSG SGTEFTLTISSLQPDDFATYYCQ QYNSYWTFGQGTKVEIK (SEQ ID NO: 23) | RASQSISS WLA (SEQ ID NO: 1) | KASSLES (SEQ ID NO: 2) | QQYNSYW T (SEQ ID NO: 3) |

TABLE 7-continued

VL and VH amino acid sequences for anti-alpha toxin mAbs

| Description | VH or VL sequence (with CDRs underlined) | CDR1 | CDR2 | CDR3 |
|---|---|---|---|---|
| mAb 12B8.19 VH | EVQLVESGGGLVQPGGSLRLSC AASGFTFS<u>RYDMH</u>WVRQATG KGLEWVS<u>VIGTDGDTYYPGSV KG</u>RFIISRENAKNSLYLEMNSL RAGDTAVYYCARD<u>RYSSSNHY NGMDV</u>WGQGTTVTVSS (SEQ ID NO: 24) | RYDMH (SEQ ID NO: 10) | VIGTDGDT YYPGSVKG (SEQ ID NO: 11) | DRYSSSNH YNGMDV (SEQ ID NO: 12) |
| mAb 28F6.1 VL | AIQMTQSPSSLSASVGDRVTITC <u>RASQGIRNDLG</u>WYQQKPGKAP KLLIY<u>DASSLQS</u>GVPSRFSGSGS GTDFTLTISSLQPEDFATYYC<u>LQ DYNYP</u>WTFGQGTKVEIK (SEQ ID NO: 25) | RASQGIRN DLG (SEQ ID NO: 4) | DASSLQS (SEQ ID NO: 5) | LQDYNYP WT (SEQ ID NO: 6) |
| mAb 28F6.1 VH | EVQLLESGGGLVQPGGSLRLSC AASGFTFS<u>SYAMT</u>WVRQAPGK GLEWVS<u>VISGSGGSTYYADSV KG</u>RFTVSRDNSKNTLYLQMNS LRAEDTAVYYCAKD<u>GRQVED YYYYYGMDV</u>WGQGTTVTVSS (SEQ ID NO: 26) | SYAMT (SEQ ID NO: 13) | VISGSGGST YYADSVK G (SEQ ID NO: 14) | DGRQVED YYYYYGM DV (SEQ ID NO: 15) |
| mAb 25E9.1 VL | DIQMTQSPSTLSASVGDRVTIT C<u>RASQSISSWLA</u>WYQQKPGKA PKLLIY<u>KASSLES</u>GVPSRFSGSG SGTEFTLTISSLQPDDFATYYC<u>Q QYNSYW</u>TFGQGTKVEIK (SEQ ID NO: 27) | RASQSISS WLA (SEQ ID NO: 1) | KASSLES (SEQ ID NO: 2) | QQYNSYW T (SEQ ID NO: 3) |
| mAb 25E9.1 VH | EVQLVESGGGLVQPGGSLRLSC TASGFTFS<u>SYDMH</u>WVRQATGK GLEWVS<u>VIDTAGDTYYPGSVK G</u>RFTISRENAKNSLYLQMNSLR AGDTAVYYCVRD<u>RYSGNFHY NGMDV</u>WGQGTTVTVSS (SEQ ID NO: 28) | SYDMH (SEQ ID NO: 7) | VIDTAGDT YYPGSVKG (SEQ ID NO: 17) | DRYSGNFH YNGMDV (SEQ ID NO: 18) |
| mAb QD20 VH | EVQLVESGGGLVQPGGSLRLSC AASGFTFS<u>SYDMH</u>WVRQATGK GLEWVS<u>GIGTAGDTYYPGSVK G</u>RFTISRENAKNSLYLQMNSLR AGDTAVYYCARD<u>RYSPTGHY MGMDV</u>WGQGTTVTVSS (SEQ ID NO: 41) | SYDMH (SEQ ID NO: 7) | GIGTAGDT YYPGSVKG (SEQ ID NO: 8) | DRYSPTGH YMGMDV (SEQ ID NO: 16) |
| mAb QD20 VL | DIQMTQSPSTLSASVGDRVTIT C<u>RASQSISSWLA</u>WYQQKPGKA PKLLIY<u>KASSLES</u>GVPSRFSGSG SGTEFTLTISSLQPDDFATYYC<u>Q QYDTYW</u>TFGQGTKVEIK (SEQ ID NO: 42) | RASQSISS WLA (SEQ ID NO: 1) | KASSLES (SEQ ID NO: 2) | QQYDTYW T (SEQ ID NO: 64) |
| mAb QD33 VH | EVQLVESGGGLVQPGGSLRLSC AASGFTFS<u>SYDMH</u>WVRQATGK GLEWVS<u>GIGTAGDTYYPGSVK G</u>RFTISRENAKNSLYLQMNSLR AGDTAVYYCARD<u>RYSRTGHY MGMDV</u>WGQGTTVTVSS (SEQ ID NO: 43) | SYDMH (SEQ ID NO: 7) | GIGTAGDT YYPGSVKG (SEQ ID NO: 8) | DRYSRTGH YMGMDV (SEQ ID NO: 65) |
| mAb QD33 VL | DIQMTQSPSTLSASVGDRVTIT C<u>RASQSISSWLA</u>WYQQKPGKA PKLLIY<u>KASSLES</u>GVPSRFSGSG SGTEFTLTISSLQPDDFATYYC<u>Q QYDTYW</u>TFGQGTKVEIK (SEQ ID NO: 44) | RASQSISS WLA (SEQ ID NO: 1) | KASSLES (SEQ ID NO: 2) | QQYDTYW T (SEQ ID NO: 64) |
| mAb QD37 VH | EVQLVESGGGLVQPGGSLRLSC AASGFTFS<u>SYDMH</u>WVRQATGK GLEWVS<u>GIGTAGDTYYPGSVK G</u>RFTISRENAKNSLYLQMNSLR AGDTAVYYCARD<u>RYSRTGHY MGMSL</u>WGQGTTVTVSS (SEQ ID NO: 45) | SYDMH (SEQ ID NO: 7) | GIGTAGDT YYPGSVKG (SEQ ID NO: 8) | DRYSRTGH YMGMSL (SEQ ID NO: 66) |

TABLE 7 -continued

VL and VH amino acid sequences for anti-alpha toxin mAbs

| Description | VH or VL sequence (with CDRs underlined) | CDR1 | CDR2 | CDR3 |
|---|---|---|---|---|
| mAb QD37 VL | DIQMTQSPSTLSASVGDRVTIT CRASQSISSWLAWYQQKPGKA PKLLIYKASSLESGVPSRFSGSG SGTEFTLTISSLQPDDFATYYCQ QYDTYWTFGQGTKVEIK (SEQ ID NO: 46) | RASQSISS WLA (SEQ ID NO: 1) | KASSLES WLA (SEQ ID NO: 2) | QQYDTYW T (SEQ ID NO: 64) |
| mAb QD3 VH | EVQLVESGGGLVQPGGSLRLSC AASGFTFSSYDMHWVRQATGK GLEWVSGIGTAGDTYYPGSVK GRFTISRENAKNSLYLQMNSLR AGDTAVYYCARDNYSRTGHY MGMDVWGQGTTVTSS (SEQ ID NO: 47) | SYDMH (SEQ ID NO: 7) | GIGTAGDT YYPGSVKG (SEQ ID NO: 8) | DNYSRTGH YMGMDV (SEQ ID NO: 67) |
| mAb QD3 VL | DIQMTQSPSTLSASVGDRVTIT CRASQSISSWLAWYQQKPGKA PKLLIYKASSLESGVPSRFSGSG SGTEFTLTISSLQPDDFATYYCK QYADYWTFGQGTKVEIK (SEQ ID NO: 48) | RASQSISS WLA (SEQ ID NO: 1) | KASSLES WLA (SEQ ID NO: 2) | KQYADYW T (SEQ ID NO: 68) |
| mAb QD4 VH | EVQLVESGGGLVQPGGSLRLSC AASGFTFSSYDMHWVRQATGK GLEWVSGIGTAGDTYYPGSVK GRFTISRENAKNSLYLQMNSLR AGDTAVYYCARDNYSRTGHY MGMDVWGQGTTVTSS (SEQ ID NO: 49) | SYDMH (SEQ ID NO: 7) | GIGTAGDT YYPGSVKG (SEQ ID NO: 8) | DNYSRTGH YMGMDV (SEQ ID NO: 67) |
| mAb QD4 VL | DIQMTQSPSTLSASVGDRVTIT CRASQSISSWLAWYQQKPGKA PKLLIYKASSLESGVPSRFSGSG SGTEFTLTISSLQPDDFATYYCQ QYDTYWTFGQGTKVEIK (SEQ ID NO: 50) | RASQSISS WLA (SEQ ID NO: 1) | KASSLES WLA (SEQ ID NO: 2) | QQYDTYW T (SEQ ID NO: 64) |
| mAb QD23 VH | EVQLVESGGGLVQPGGSLRLSC AASGFTFSSYDMHWVRQATGK GLEWVSGIGTAGDTYYPGSVK GRFTISRENAKNSLYLQMNSLR AGDTAVYYCARDRYSPTGHY MGMSLWGQGTTVTSS (SEQ ID NO: 51) | SYDMH (SEQ ID NO: 7) | GIGTAGDT YYPGSVKG (SEQ ID NO: 8) | DRYSPTGH YMGMSL (SEQ ID NO: 78) |
| mAb QD23 VL | DIQMTQSPSTLSASVGDRVTIT CRASQSISSWLAWYQQKPGKA PKLLIYKASSLESGVPSRFSGSG SGTEFTLTISSLQPDDFATYYCQ QYDTYWTFGQGTKVEIK (SEQ ID NO: 52) | RASQSISS WLA (SEQ ID NO: 1) | KASSLES WLA (SEQ ID NO: 2) | QQYDTYW T (SEQ ID NO: 64) |
| mAb QD32 VH | EVQLVESGGGLVQPGGSLRLSC AASGFTFSSYDMHWVRQATGK GLEWVSGIGTAGDTYYPGSVK GRFTISRENAKNSLYLQMNSLR AGDTAVYYCARDRYSRTGHY MGMDVWGQGTTVTSS (SEQ ID NO: 53) | SYDMH (SEQ ID NO: 7) | GIGTAGDT YYPGSVKG (SEQ ID NO: 8) | DRYSRTGH YMGMDV (SEQ ID NO: 65) |
| mAb QD32 VL | DIQMTQSPSTLSASVGDRVTIT CRASQSISSWLAWYQQKPGKA PKLLIYKASSLESGVPSRFSGSG SGTEFTLTISSLQPDDFATYYCK QYADYWTFGQGTKVEIK (SEQ ID NO: 54) | RASQSISS WLA (SEQ ID NO: 1) | KASSLES WLA (SEQ ID NO: 2) | KQYADYW T (SEQ ID NO: 68) |
| mAb 2A3GL VH | EVQLVESGGGLVQPGGSLRLSC AASGFTFSSYDMHWVRQATGK GLEWVSGIGTAGDTYYPGSVK GRFTISRENAKNSLYLQMNSLR AGDTAVYYCARDNYSSTGGY YGMDVWGQGTTVTSS (SEQ ID NO: 55) | SYDMH (SEQ ID NO: 7) | GIGTAGDT YYPGSVKG (SEQ ID NO: 8) | DNYSSTGG YYGMDV (SEQ ID NO: 9) |

TABLE 7 -continued

VL and VH amino acid sequences for anti-alpha toxin mAbs

| Description | VH or VL sequence (with CDRs underlined) | CDR1 | CDR2 | CDR3 |
|---|---|---|---|---|
| mAb 2A3GL VL | DIQMTQSPSTLSASVGDRVTIT CRASQSISSWLAWYQQKPGKA PKLLIYKASSLESGVPSRFSGSG SGTEFTLTISSLQPDDFATYYCQ QYNSYWTFGQGTKVEIK (SEQ ID NO: 56) | RASQSISS WLA (SEQ ID NO: 1) | KASSLES (SEQ ID NO: 2) | QQYNSYW T (SEQ ID NO: 3) |
| mAb LC10 VH | EVQLVESGGGLVQPGGSLRLSC AASGFTFSSHDMHWVRQATGK GLEWVSGIGTAGDTYYPDSVK GRFTISRENAKNSLYLQMNSLR AGDTAVYYCARDRYSPTGHYY GMDVWGQGTTVTVSS (SEQ ID NO: 57) | SHDMH (SEQ ID NO: 69) | GIGTAGDT YYPDSVKG (SEQ ID NO: 70) | DRYSPTGH YYGMDV (SEQ ID NO: 71) |
| mAb LC10 VL | DIQMTQSPSTLSASVGDRVTIT CRASQSISSWLAWYQQKPGKA PKLLIYKASSLESGVPSRFSGSG SGTEFTLTISSLQPDDFATYYCK QYADYWTFGQGTKVEIK (SEQ ID NO: 58) | RASQSISS WLA (SEQ ID NO: 2) | KASSLES (SEQ ID NO: 68) | KQYADYW T (SEQ ID NO: 1) |
| mAb TVES VH | EVQLVESGGGLVQPGGSLRLSC AASGFTFSSYDMHWVRQATGK GLEWVSGIGTAGDTYYPGSVK GRFTISRENAKNSLYLQMNSLR AGDTAVYYCARDNYSPTGGY YGMDVWGQGTTVTVSS (SEQ ID NO: 59) | SYDMH (SEQ ID NO: 7) | GIGTAGDT YYPGSVKG (SEQ ID NO: 8) | DNYSPTGG YYGMDV (SEQ ID NO: 72) |
| mAb TVES VL | DIQMTQSPSTLSASVGDRVTIT CRASQSISSWLAWYQQKPGKA PKLLIYKASSLKSGVPSRFSGSG SGTEFTLTISSLQPDDFATYYCQ QYESYWTFGQGTKVEIK (SEQ ID NO: 60) | RASQSISS WLA (SEQ ID NO: 73) | KASSLKS (SEQ ID NO: 74) | QQYESYW T (SEQ ID NO: 1) |
| mAb 3H7KAD VH | EVQLVESGGGLVQPGGSLRLSC AASGFTFSSHDMHWVRQATGK GLEWVSGIGTRGDTYYPDSVK GRFTISRENAKNSLYLQMNSLR AGDTAVYYCARDRYSPTGHYY GMDVWGQGTTVTVSS (SEQ ID NO: 61) | SHDMH (SEQ ID NO: 69) | GIGTRGDT YYPDSVKG (SEQ ID NO: 75) | DRYSPTGH YYGMDV (SEQ ID NO: 71) |
| mAb 3H7KAD VL | DIQMTQSPSTLSASVGDRVTIT CRASQSISSWLAWYQQKPGKA PKLLIYKASSLESGVPSRFSGSG SGTEFTLTISSLQPDDFATYYCK QYADYWTFGQGTKVEIK (SEQ ID NO: 58) | RASQSISS WLA (SEQ ID NO: 2) | KASSLES (SEQ ID NO: 2) | KQYADYW T (SEQ ID NO: 68) |
| mAb LC9 VH | EVQLVESGGGLVQPGGSLRLSC AASGFTFSSHDMHWVRQATGK GLEWVSGIGTRGDTYYPDSVK GRFTISRENAKNSLYLQMNSLR AGDTAVYYCARDKYSPTGHY YGMDVWGQGTTVTVSS (SEQ ID NO: 62) | SHDMH (SEQ ID NO: 69) | GIGTRGDT YYPDSVKG (SEQ ID NO: 75) | DKYSPTGH YYGMDV (SEQ ID NO: 76) |
| mAb LC9 VL | DIQMTQSPSTLSASVGDRVTIT CRASQSISSWLAWYQQKPGKA PKLLIYKASSLESGVPSRFSGSG SGTEFTLTISSLQPDDFATYYCK QYADYWTFGQGTKVEIK (SEQ ID NO: 58) | RASQSISS WLA | KASSLES (SEQ ID NO: 2) | KQYADYW T (SEQ ID NO: 68) |
| mAb LC4 VH | EVQLVESGGGLVQPGGSLRLSC AASGFTFSSHDMHWVRQATGK GLEWVSGIGTRGDTYYPDSVK GRFTISRENAKNSLYLQMNSLR AGDTAVYYCARDKYSPTGHY YGMDVWGQGTTVTVSS (SEQ ID NO: 62) | SHDMH (SEQ ID NO: 69) | GIGTRGDT YYPDSVKG (SEQ ID NO: 75) | DKYSPTGH YYGMDV (SEQ ID NO: 76) |

TABLE 7 -continued

VL and VH amino acid sequences for anti-alpha toxin mAbs

| Description | VH or VL sequence (with CDRs underlined) | CDR1 | CDR2 | CDR3 |
|---|---|---|---|---|
| mAb LC4 VL | DIQMTQSPSTLSASVGDRVTIT CRASQSISSWLAWYQQKPGKA PKLLIYKASSLVKGVPSRFSGS GSGTEFTLTISSLQPDDFATYYC QQYESYWTFGQGTKVEIK (SEQ ID NO: 63) | RASQSISS WLA (SEQ ID NO: 1) | KASSLVK (SEQ ID NO: 77) | QQYESYW T (SEQ ID NO: 74) |
| mAb LC5 VH | EVQLVESGGGLVQPGGSLRLSC AASGFTFSSHDMHWVRQATGK GLEWVSGIGTAGDTYYPDSVK GRFTISRENAKNSLYLQMNSLR AGDTAVYYCARDRYSPTGHYY GMDVWGQGTTVTVSS (SEQ ID NO: 79) | SHDMH (SEQ ID NO: 69) | GIGTAGDT YYPDSVKG (SEQ ID NO: 70) | DRYSPTGH YYGMDV (SEQ ID NO: 71) |
| mAb LC5 VL | DIQMTQSPSTLSASVGDRVTIT CRASQSISSWLAWYQQKPGKA PKLLIYKASSLVKGVPSRFSGS GSGTEFTLTISSLQPDDFATYYC QQYESYWTFGQGTKVEIK (SEQ ID NO: 63) | RASQSISS WLA (SEQ ID NO: 1) | KASSLVK (SEQ ID NO: 77) | QQYESYW T (SEQ ID NO: 74) |

TABLE 8

VL and VH nucleotide sequences for anti-alpha toxin mAbs

| SEQ ID NO: | Description | Sequence |
|---|---|---|
| SEQ ID NO: 29 | mAb 2A3.1 VL nucleotide sequence | GACATCCAGATGACCCAGTCTCCTTCCA CCCTGTCTGCATCTGTAGGAGACAGAGT CACCATCACTTGCCGGGCCAGTCAGAGT ATTAGTAGCTGGTTGGCCTGGTATCAGC AGAAACCAGGGAAAGCCCCTAAACTCCT GATCTATAAGGCGTCTAGTTTAGAAAGTG GGGTCCCATCAAGGTTCAGCGGCAGTGG ATCTGGGACAGAATTCACTCTCACCATCA GCAGCCTGCAGCCTGATGATTTTGCAAC TTATTACTGCCAACAGTATAATAGTTATTG GACGTTCGGCCAAGGGACCAAGGTGGA AATCAAA |
| SEQ ID NO: 30 | mAb 2A3.1 VH nucleotide sequence | GAGGTGCAGCTGGTGGAGTCTGGGGGA GGCTTGGTACAGCCTGGGGGGTCCCTG AGACTCTCCTGTGCAGCCTCTGGATTCA CCTTCAGTAGCTACGACATGCACTGGGT CCGCCAAGCTACAGGAAAAGGTCTGGAG TGGGTCTCAGGTATTGGCACTGCTGGTG ACACATATTATCCAGGCTCCGTGAAGGG CCGATTCACCATCTCCAGAGAAAATGCC AAGAACTCCTTGTATCTTCAATTGAACAG CCTGAGAGCCGGGGACACGGCTGTGTA CTTCTGTGCAAGAGACAATTATAGCAGCA CCGGGGGGTACTACGGTATGGACGTCTG GGGCCAAGGGACCACGGTCACCGTCTC CTCA |
| SEQ ID NO: 31 | mAb 10A7.5 VL nucleotide sequence | GACATCCAGATGACCCAGTCTCCTTCCA CCCTGTCTGCATCTGTAGGAGACAGAGT CACCATCACTTGCCGGGCCAGTCAGAGT ATTAGTAGCTGGTTGGCCTGGTATCAGC AGAAACCAGGGAAAGCCCCTAAACTCCT GATCTATAAGGCGTCTAGTTTAGAAAGTG GGGTCCCATCAAGGTTCAGCGGCAGTGG ATCTGGGACAGAATTCACTCTCACCATCA GCAGCCTGCAGCCTGATGATTTTGCAAC TTATTACTGCCAACAGTATAATAGTTATTG GACGTTCGGCCAAGGGACCAAGGTGGA AATCAAA |

TABLE 8 -continued

VL and VH nucleotide sequences for anti-alpha toxin mAbs

| SEQ ID NO: | Description | Sequence |
| --- | --- | --- |
| SEQ ID NO: 32 | mAb 10A7.5 VH nucleotide sequence | GAGGTGCAGCTGGTGGAGTCTGGGGGA GGCTTGGTACAGCCTGGGGGGTCCCTG AGACTCTCCTGTGCAGCCTCTGGATTCA CCTTCAGTAGGTACGACATGCACTGGGT CCGCCAAGCTACAGGAAAAGGTCTGGAG TGGGTCTCAGTTATTGGTACTGATGGTGA CACATACTATCCAGGCTCCGTGAAGGGC CGATTCATCATCTCCAGAGAAAATGCCAA GAACTCCTTGTATCTTGAAATGAACAGCC TGAGAGCCGGGGACACGGCTGTGTATTA CTGTGCAAGAGATCGGTATAGCAGCTCG AACCACTACAACGGTATGGACGTCTGGG GCCAAGGGACCACGGTCACCGTCTCCTC A |
| SEQ ID NO: 33 | mAb 12B8.19 VL nucleotide sequence | GACATCCAGATGACCCAGTCTCCTTCCA CCCTGTCTGCATCTGTAGGAGACAGAGT CACCATCACTTGCCGGGCCAGTCAGAGT ATTAGTAGCTGGTTGGCCTGGTATCAGC AGAAACCAGGGAAAGCCCCTAAGGTCCT GATCTATAAGGCGTCTAGTTTAGAAAGTG GGGTCCCATCAAGGTTCAGCGGCAGTGG ATCTGGGACAGAATTCACTCTCACCATCA GCAGCCTGCAGCCTGATGATTTTGCAAC TTATTACTGCCAACAGTATAATAGTTATTG GACGTTCGGCCAAGGGACCAAGGTGGA AATCAAA |
| SEQ ID NO: 34 | mAb 12B8.19 VH nucleotide sequence | GAGGTGCAGCTGGTGGAGTCTGGGGGA GGCTTGGTACAGCCTGGGGGGTCCCTG AGACTCTCCTGTGCAGCCTCTGGATTCA CCTTCAGTAGGTACGACATGCACTGGGT CCGCCAAGCTACAGGAAAAGGTCTGGAG TGGGTCTCAGTTATTGGTACTGATGGTGA CACATACTATCCAGGCTCCGTGAAGGGC CGATTCATCATCTCCAGAGAAAATGCCAA GAACTCCTTGTATCTTGAAATGAACAGCC TGAGAGCCGGGGACACGGCTGTGTATTA CTGTGCAAGAGATCGGTATAGCAGCTCG AACCACTACAACGGTATGGACGTCTGGG GCCAAGGGACCACGGTCACCGTCTCCTC A |
| SEQ ID NO: 35 | mAb 28F6.1 VL nucleotide sequence | GCCATCCAGATGACCCAGTCTCCATCCT CCCTGTCTGCATCTGTAGGAGACAGAGT CACCATCACTTGCCGGGCAAGTCAGGGC ATTAGAAATGATTTAGGCTGGTATCAGCA GAAACCAGGGAAAGCCCCTAAGCTCCTG ATCTATGATGCATCCAGTTTACAAAGTGG GGTCCCATCAAGGTTCAGCGGCAGTGGA TCTGGCACAGATTTCACTCTCACCATCAG CAGCCTGCAGCCTGAAGATTTTGCAACTT ATTACTGTCTACAAGATTACAATTACCCG TGGACGTTCGGCCAAGGGACCAAGGTG GAAATCAAA |
| SEQ ID NO: 36 | mAb 28F6.1 VH nucleotide sequence | GAGGTGCAGCTGTTGGAGTCTGGGGGA GGCTTGGTACAGCCTGGGGGGTCCCTG AGACTCTCCTGTGCAGCCTCTGGATTCA CCTTTAGCAGCTATGCCATGACCTGGGT CCGCCAGGCTCCAGGGAAGGGGCTGGA ATGGGTCTCAGTTATTAGTGGTAGTGGT GGTAGCACATACTACGCAGACTCCGTGA AGGGCCGGTTCACCGTCTCCAGAGACAA TTCCAAGAACACGCTGTATCTGCAAATGA ACAGCCTGAGAGCCGAGGACACGGCCG TATATTACTGTGCGAAAGATGGGAGGCA GGTCGAGGATTACTACTACTACTACGGTA TGGACGTCTGGGGCCAAGGGACCACGG TCACCGTCTCCTCA |
| SEQ ID NO: 37 | mAb 25E9.1 VL nucleotide sequence | GACATCCAGATGACCCAGTCTCCTTCCA CCCTGTCTGCATCTGTAGGAGACAGAGT CACCATCACTTGCCGGGCCAGTCAGAGT ATTAGTAGCTGGTTGGCCTGGTATCAGC AGAAACCAGGGAAAGCCCCTAAGCTCCT |

TABLE 8 -continued

VL and VH nucleotide sequences for anti-alpha toxin mAbs

| SEQ ID NO: | Description | Sequence |
|---|---|---|
| | | GATCTATAAGGCGTCTAGTTTAGAAAGTG GGGTCCCATCAAGGTTCAGCGGCAGTGG ATCTGGGACAGAATTCACTCTCACCATCA GCAGCCTGCAGCCTGATGATTTTGCAAC TTATTACTGCCAACAGTATAATAGTTATTG GACGTTCGGCCAAGGGACCAAGGTGGA AATCAAA |
| SEQ ID NO: 38 | mAb 25E9.1 VH nucleotide sequence | GAGGTGCAGCTGGTGGAGTCTGGGGGA GGCTTGGTACAGCCTGGGGGGTCCCTG AGACTCTCCTGTACAGCCTCTGGATTCAC CTTCAGTAGTTACGACATGCACTGGGTC CGCCAAGCTACAGGAAAAGGTCTGGAGT GGGTCTCAGTTATTGATACTGCTGGTGA CACATACTATCCAGGCTCCGTGAAGGGC CGATTCACCATCTCCAGAGAAATGCCAA GAACTCCTTGTATCTTCAAATGAACAGCC TGAGAGCCGGGGACACGGCTGTGTATTA CTGTGTAAGAGATAGGTATAGTGGGAAC TTCCACTACAACGGTATGGACGTCTGGG GCCAAGGGACCACGGTCACCGTCTCCTC A |

TABLE 9

VL and VH CDR summary table

| Description | SEQ ID NOs |
|---|---|
| VL CDR 1 | 1, 4 |
| VL CDR 2 | 2, 5, 73, 77 |
| VL CDR 3 | 3, 6, 64, 68, 74 |
| VH CDR 1 | 7, 10, 13, 69 |
| VH CDR 2 | 8, 11, 14, 17, 70, 75 |
| VH CDR 3 | 9, 12, 15, 18, 16, 65, 66, 67, 71, 72, 76, 78 |

"Structural characterization of the alpha-hemolysin monomer from *Staphylococcus aureus*." *Proteins* 75(1): 118-26 (2009)) and 25% sequence identity with alpha toxin (FIG. 20). A series of chimeric variants were constructed by systematically replacing 50 alpha toxin amino acids (aa) with their corresponding LukF-PV counterparts. Shorter regions within select 50 aa segments of interest were also replaced (Table 11). A ProteOn instrument was employed to analyze the binding affinity of LC10 YTE to these variants. The binding results of LC10 YTE to the variants are summarized in Table 11.

TABLE 10

Alpha Toxin Amino Acid Sequences

| *Staphylococcus aureus* alpha toxin | adsdiniktgttdigsnttvktgdlvtydkengmhkkvfysfiddknhnkkllvirtkgtiaggyrvyseega nksglawpsafkvqlqlpdnevaqisdyyprnsidtkeymstltygfngnvtgddtgkiggliganvsigh tlkyvqpdfktilesptdkkvgwkvifnnmvnqnwgpydrdswnpvygnqlfmktrngsmkaadnfld pnkasslssgfspdfatvitmdrkaskqqtnidviyervrddyqlhwtstnwkgtntkdkwtdrsseryki dwekeemtn (SEQ ID NO: 39) |
|---|---|
| *S. aureus* alpha toxin H35L mutant | adsdiniktgttdigsnttvktgdlvtydkengmlkkvfysfiddknhnkkllvirtkgtiagqyrvyseegan ksglawpsafkvqlqlpdnevaqisdyyprnsidtkeymstltygfngnvtgddtgkiggliganvsightl kyvqpdfktilesptdkkvgwkvifnnmvnqnwgpydrdswnpvygnqlfmktrngsmkaadnfldp nkasslssgfspdfatvitmdrkaskqqtnidviyervrddyqlhwtstnwkgtntkdkwtdrsserykid wekeemtn (SEQ ID NO: 40) |

Example 11

Mapping of Anti-Staphylococcal Alpha Toxin Antibodies Binding Regions

Figure 19:
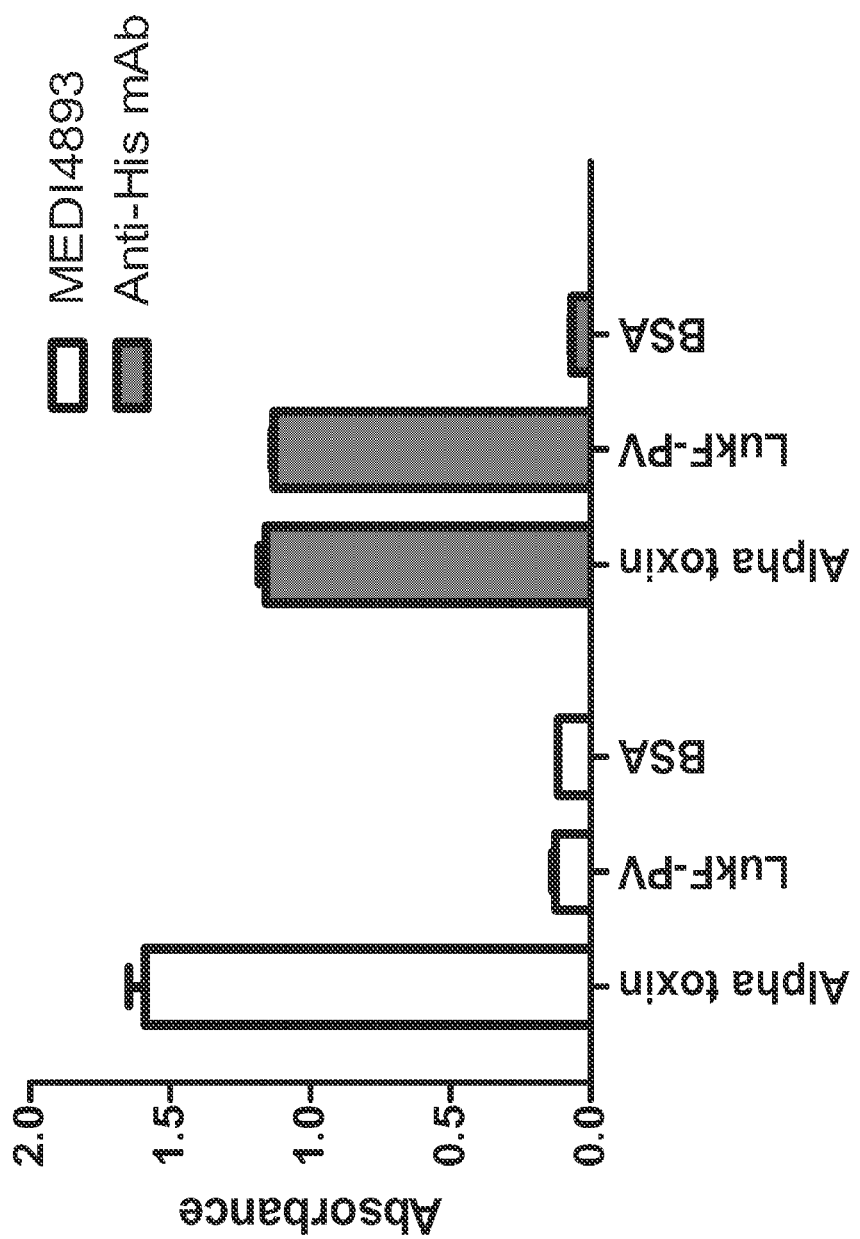
FIG. 19 graphically depicts the ELISA characterization of the binding of LC10 YTE to alpha toxin and LukF-PV. Bacterial lysate containing His-tagged alpha toxin or LukF-PV was coated on the surface of a 96-well. LC10 YTE or mouse anti-His mAb was added to the coated wells and incubated for 1 h. The expression levels of alpha toxin and LukF-PV were similar as shown by the binding signals of anti-His mAb, while LC10 YTE only bound significantly to alpha toxin and not LukF-PV.

Chimeric variants, composed of portions of alpha toxin and LukF-PV, were constructed to identify the fragment of alpha toxin to which an antibody corresponding to mAb LC10 containing an Fc variant (LC10 YTE) binds. LukF-PV was chosen as the chimeric partner because it is not recognized by LC10 YTE (FIG. 19), but shares high structural similarity (Gouaux, E., M. Hobaugh, et al. "alpha-Hemolysin, gamma-hemolysin, and leukocidin from *Staphylococcus aureus*: distant in sequence but similar in structure." Protein Sci 6(12): 2631-5 (1997); Meesters, C., A. Brack, et al.

TABLE 11

Binding profiles of LC10 YTE to alpha toxin/LukF-PV chimeric variants

| Chimeric variants | Regions of alpha toxin replaced with LukF-PV counterparts | Expression levels monitored by anti-alpha toxin polyclonal antibody | Binding affinity of MEDI4893 |
|---|---|---|---|
| Alpha toxin | N/A | Good* | ~100 pM |
| LukF-PV | N/A | N/A | No binding |
| KO_1-51 | aa 1-51 | Low** | ~100 pM |
| KO_52-110 | aa 52-110 | Low | No binding |
| KO_111-147 | aa 111-147 | Good | ~100 pM |
| KO_148-205 | aa 148-205 | Good | ~100 pM |

TABLE 11-continued

Binding profiles of LC10 YTE to alpha toxin/LukF-PV chimeric variants

| Chimeric variants | Regions of alpha toxin replaced with LukF-PV counterparts | Expression levels monitored by anti-alpha toxin poly-clonal antibody | Binding affinity of MEDI4893 |
|---|---|---|---|
| KO_204-241 | aa 204-241 | Low | No binding |
| KO_248-293 | aa 248-293 | Low | No binding |
| KO_52-62 | aa 52-62 | Good | ~100 pM |
| KO_63-72 | aa 63-72 | Good | ~100 pM |
| KO_73-81 | aa 73-81 | No expression | N/A |
| KO_82-90 | aa 82-90 | Good | ~100 pM |
| KO_91-100 | aa 91-100 | Good | ~100 pM |
| KO_101-110 | aa 101-110 | Good | No binding |
| KO_204-231 | aa 204-231 | Good | No binding |
| KO_204-213 | aa 204-213 | Good | ~100 pM |
| KO_214-223 | aa 214-223 | Good | ~100 pM |
| KO_224-231 | aa 224-231 | Good | No binding |
| KO_232-247 | aa 232-247 | Good | ~100 pM |
| KO_248-277 | aa 248-277 | Good | ~1100 pM (KD dropped 10 times) |
| KO_278-293 | aa 278-293 | Good | ~100 pM |

*The binding signals of anti-alpha toxin poly at 50 nM were above 100RUs.
**The binding signals of anti-alpha toxin poly at 50 nM were below 100RUs.

All chimeric constructs could be expressed at some level with the exception of KO_73-81, (Table 11). LC10 YTE did not bind to variants encoding for LukF-PV in place of aa 101-110 of alpha toxin (KO_52-110 and KO_101-110) or aa 224-231 (KO_204-241, KO_204-231 and KO_224-231). Binding of LC10 YTE was significantly impaired or completely disrupted when replacing aa 248-277 (KO_248-277) or its larger segment aa 248-293 (KO_248-293), respectively.

In certain instances, an apparent lack of binding to LC10 YTE, can be explained by individual alpha toxin/LukF-PV variants exhibiting an incorrect folding. An overall inability to correctly fold may also account for the apparent lack of expression of KO 73-81. In addition, the amino acid sequence homology between alpha toxin and LukF-PV varies substantially at different regions. For example, the segment corresponding to aa 179-193 of alpha toxin shares 67% identity with LukF-PV, while the entire sequence shares 25% identity. Thus, although no effect on LC10 YTE binding was seen when swapping regions of high sequence homology, these regions could potentially contain additional sequences to which the LC10 YTE antibody binds.

The results from the mutagenesis analysis above indicate that replacement of any of the three regions of aa 101-110, aa 224-231, and 248-293 of alpha toxin with LukF-PV residues impaired LC10 YTE binding, while replacing the remaining aa regions had no significant impact.

Figure 21:
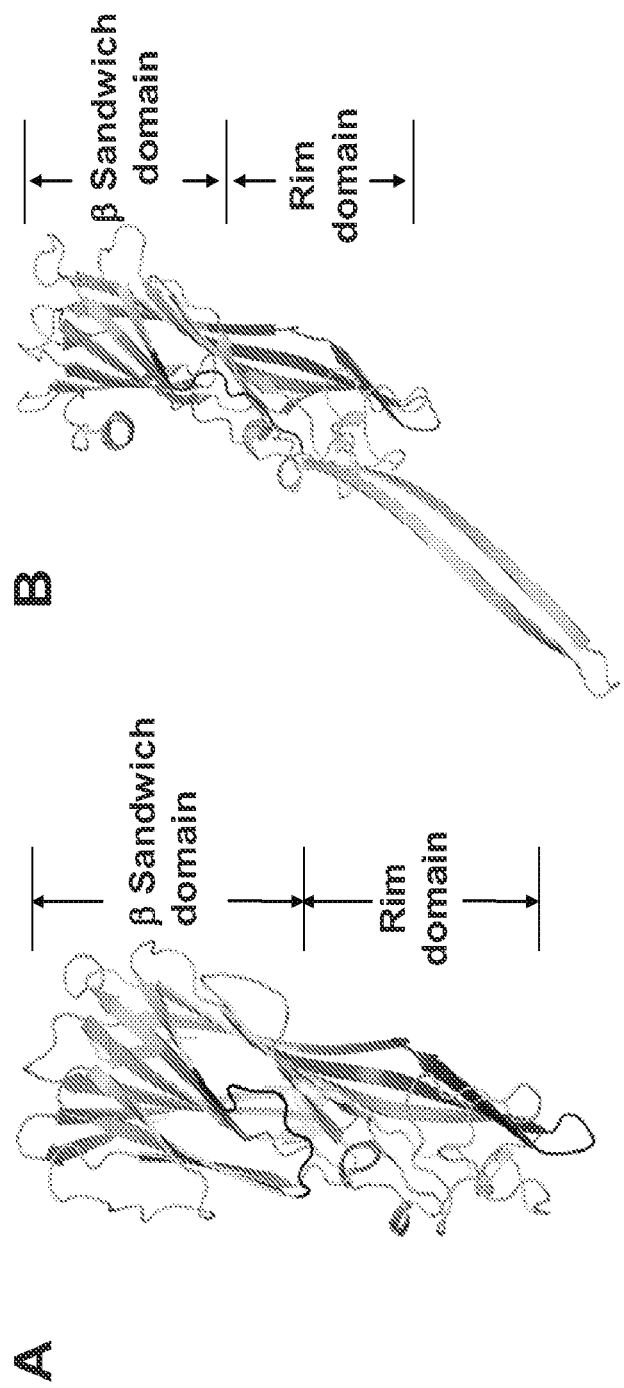
FIG. 21 depicts cartoon representations of alpha toxin structures. A) Cartoon representation of the modeled structure of a soluble monomer of alpha toxin. The modeled monomer structure of alpha toxin was built with Maestro 9.1 (Schrodinger Inc) using the crystal structure of LukF-PV as the template (Protein Data Bank entry 1PVL) (Pedelacq, Maveyraud et al. 1999). B) Cartoon representation of the crystal structure of an alpha toxin protomer from a hexamer (Protein Data Bank entry 7AHL) (Song, Hobaugh et al. 1996). aa 101-110 are shown in blue, aa 224-231 in orange and aa 248-277 in red.

These three regions represent two different locations in the three dimensional structure of alpha toxin. Segments corresponding to aa 101-110 and 224-231 are in spatial proximity and localized on one side of a Beta-sandwich domain, whereas the segment corresponding to aa 248-277 is mainly located on the "Rim" domain (Song, L., M. R. Hobaugh, et al., "Structure of staphylococcal alpha-hemolysin, a heptameric transmembrane pore." Science 274(5294): 1859-66 (1996)) (FIG. 21).

The segment corresponding to aa 248-277 showed impact on binding and also contained the X-ray structural contact residues identified as comprising aa 261-272 (in which T263, N264, and K266 are actual contacting residues) (FIG. 20). In addition, the crystal structure revealed another segment corresponding to aa 173-201 in which D183, W187, and N188 are actual contacting residues (FIG. 20). The chimeric variant that contained this particular segment (KO_148-205) still exhibited good binding to LC10 YTE. This is likely attributable to this particular region's high sequence homology (52% identity and 63% similarity) between alpha toxin and LukF-PV. The amino acids around the contacting residues (aa 179-193) share even higher homology (67% identity), while, in contrast, the entire sequence shares only 25% identity.

Using the mutagenesis-based approach, the segment corresponding to aa 248-277 was identified as important for the binding for LC10 YTE. This was further confirmed by structural analysis of the LC10 YTE/alpha toxin complex structure. Structural analysis also revealed certain contact residues within the aa 248-277 fragment that are present within aa 261-272.

As discussed above, X-ray crystallography experiments to determine the contact resides of the LC10 YTE mAb were conducted. Purified α-toxin (residues 1 through 293) and LC10 YTE Fab were separately concentrated. Nearly equimolar amounts of these proteins were mixed together and the solution was subjected to Gel-Filtration chromatography on Sephadex S75 (GE Healthcare) column. The eluted peak contained both protein molecules bound to each other. Further concentration and crystallization yielded crystals that diffracted to 2.5 Å.

The structure of the complex was solved using the molecular replacement method. The previously determined Fab structure (D25) with a removed complementarity determining regions was used as a template for LC10 YTE Fab. The monomer of the α-toxin molecule derived from a heptameric complex (PDB Id. 7AHL) with some truncations was used as a template for the α-toxin molecule. The sequence of the alpha-toxin molecule used for crystallographic research corresponds to that of SEQ ID NO: 39. Two complexes per asymmetric unit of the LC10 YTE-α-toxin complex were identified using a Phaser program from the CCP4 suite of programs. The model of the structure was further refined using a Refmac program from the CCP4 suite of programs. Manual building and iterative model improvements were performed using the specific crystallographic program "O".

Figure 22:
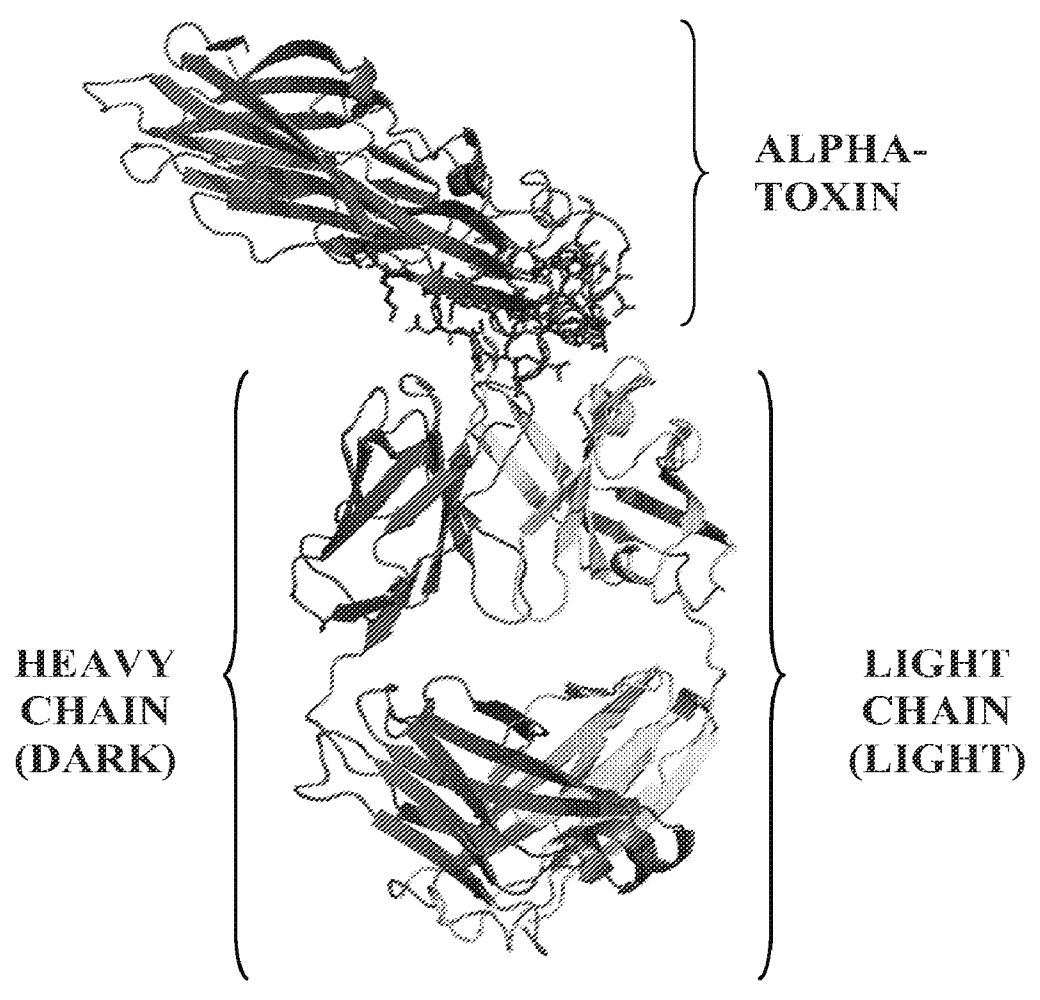

Both heavy and light chains of the Fab were found to be in contact with the α-toxin molecule (FIG. 22). In particular, the crystallography studies determined contact residues within the alpha-toxin molecule that corresponded to the following for both heavy and light chains: N177, W179, G180, P181, Y182, D183, D185, S186, W187, N188, P189, V190, Y191 and R200. In addition, the light chain was determined to have contacts with T261, T263, N264, K266 and K271. Paratopes were identified as: LC-W32 (CDR1), K50 (CDR2), Y91, A92, N93, Y94, W95 (CDR3); HC-D33 (CDR1), T53, A54, D56, Y58 (CDR2), D98, Y100, P102, T103, G104, H105, Y106 (CDR3).

Figure 23:
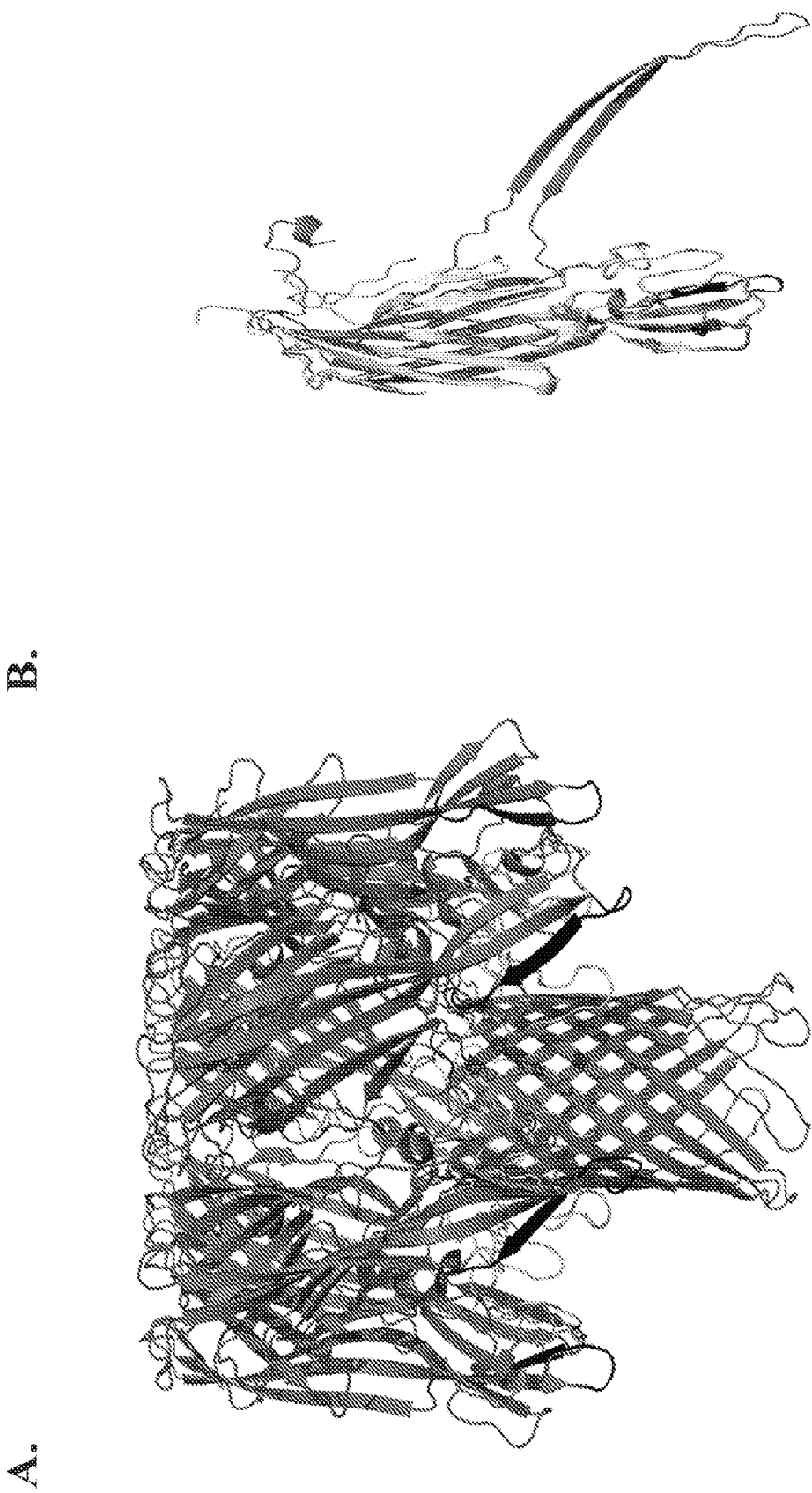
FIG. 23 is a cartoon representation of the heptameric and monomeric states of the α-toxin molecule. a. A mushroom-like heptameric assembly of the α-toxin molecule that creates a pore on the surface of the host cell. The grey and black colored regions correspond to LC10 YTE contact residues that are shielded in the model. The contact residues being present in the shielded positions are consistent LC10 blocking heptamer formation. b. Superimposed structures of α-toxin molecules before (light grey) and after (dark grey) pore formation.

Molecular modeling incorporating the structural data from the crystallographic analysis revealed that most of the α-toxin structure remained unchanged during the transition from the monomeric state to the heptameric state. However, a critical binding region (where contact residues were identified as T261, T263, N264, K266 and K271) was shown to correspond to a portion of the α-toxin molecule that participates in heptamer formation. It is this critical region that is compactly folded when the α-toxin molecule is in a monomeric state, that extends as a loop prior to insertion into a host cell membrane (FIG. 23b), and ultimately forms the stalk of the mushroom-like structure after assembly into the heptameric state (FIG. 23a). In the heptameric state, this region, as shown in FIG. 24a, would be predicted to be shielded from binding by the LC10 YTE antibody molecule.

Example 12

Therapeutic Efficacy of Anti-Staphylococcal Alpha Toxin Antibodies

Figure 24:
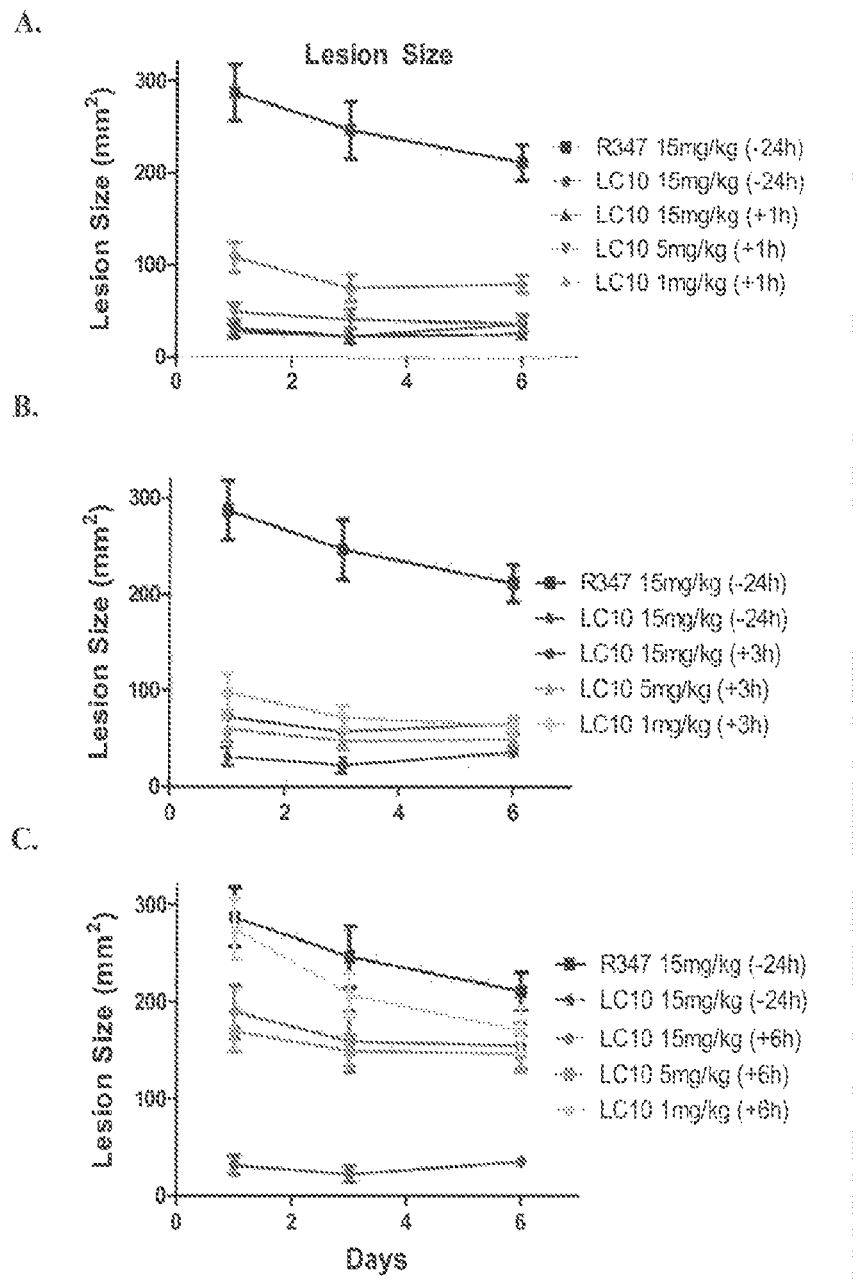
FIG. 24 graphically represents the treatment efficacy of LC10 in a murine dermonecrosis model. Groups of 5 Balb/C mice were passively immunized with 15 mg/kg LC10 or R347 Balb/C mice were infected intranasally with $2 \times 10^8$ *S. aureus* Wood. (A) 1 hr, (B) 3 hr or (C) 6 hr postinfection the mice were then treated with either 5, 15 or 45 mg/kg LC10 and lesion size monitored for 6 days. Groups of 5 administered 15 mg/kg LC10 or R347 24 hr prior to bacterial challenge were included as controls.

Results discussed above describe the efficacy of anti-AT mAbs used in prophylaxis. To explore the possibility that these mAbs also can function therapeutically, the efficacy of LC10 was tested in a therapeutic setting in both the dermonecrosis and pneumonia models. In the dermonecrosis model, LC10 was administered IV 24 hrs before bacterial challenge (prophylaxis) and 1, 3 or 6 hrs following intradermal infection (therapy). Lesion size on the animals was monitored for 6 days. Prophylaxis (−24 hr) and treatment 1 or 3 hrs post infection resulted in a reduction in lesion size relative to the negative control (R347) (FIG. 24). The strong treatment benefit was lost when LC10 was delivered 6 hr post infection in this model. These results indicate LC10 can function as an effective therapy for staphylococcal skin and soft tissue infections.

Figure 25:
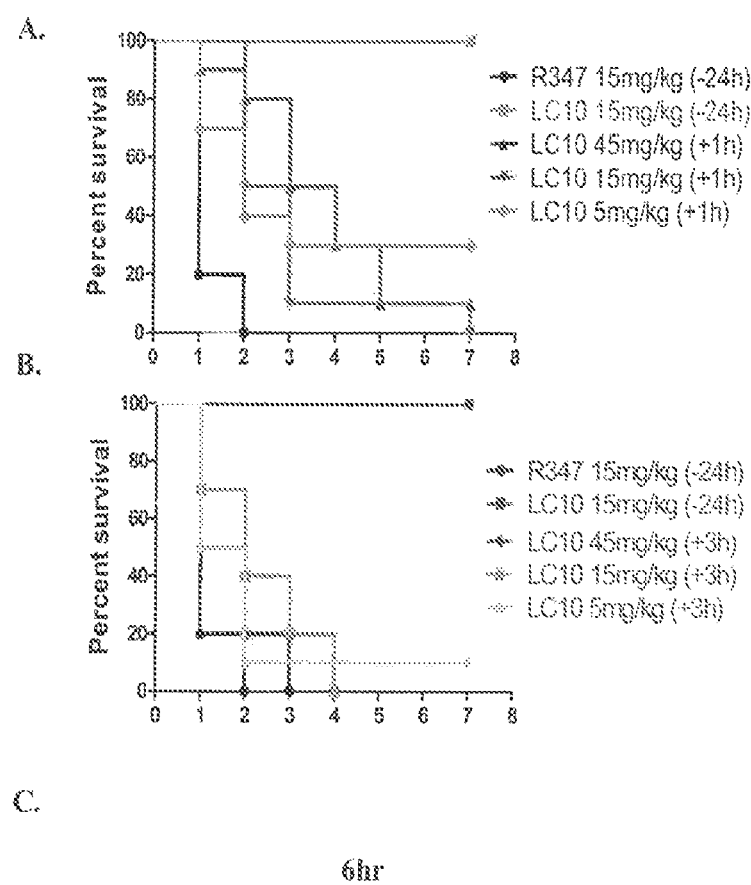
FIG. 25 graphically represents the treatment efficacy of LC10 in a murine pneumonia model. Groups of 10 C57BL/6 mice were passively immunized with 15 mg/kg LC10 or R347 24 hr prior to intranasal challenge with $2 \times 10^8$ *S. aureus* USA300. Groups of 10 C57BL/6 mice were infected intranasally with $2 \times 10^8$ *S. aureus* USA300. (A) 1 hr, (B) 3 hr or (C) 6 hr postinfection the mice were then treated with either 5, 15 or 45 mg/kg LC10 and survival monitored for 7 days. Groups of 10 administered 15 mg/kg LC10 or R347 24 hr prior to bacterial challenge were included as controls.

Similar experiments were conducted in the pneumonia model in which LC10 was delivered to the mice (IV) either in prophylaxis or 1, 3 or 6 hrs post intranasal infection. As expected, prophylactic mAb administration resulted in complete survival. (FIG. 25) Although complete survival did not result when LC10 was administered 1, 3 or 6 hrs post infection, there was a benefit in time to death relative to a negative control when LC10 was used in treatment 1 hour post infection at the highest LC10 doses. In view of the model's requirement for high infection dose and rapid onset of death, these survival improvements indicate that a therapeutic improvement during a human infection can occur.

Example 13

Efficacy of Vancomycin in Combination with the Anti-Alpha Toxin mAb LC-10

Studies were undertaken to assess the potential of anti-alpha toxin mAb LC 10 for use in adjunctive therapy with vancomycin in a murine pneumonia model by comparing anti-alpha toxin mAb and vancomycin monotherapy to combination therapy.

Seven-week old female C57BL/6J mice were infected intranasally with 2e8 cfu (LD100) of methicillin-resistant Staphylococcus aureus USA300. Vancomycin and LC-10 were individually titrated to determine the optimal and sub-efficacious doses. For mAb evaluation in monotherapy or dual therapy with vancomycin, mice were treated one hour post-infection, with a single intraperitoneal dose of LC-10, or the negative control antibody R347 (15 mg/kg). Vancomycin treatment in mono or dual therapy was initiated 1 hr postinfection and administered BID subcutaneously 3 days. The percent survival for all treated groups was determined at the end of seven days. Survival curves were analyzed using the Mandel-Cox log-rank test.

Figure 27:
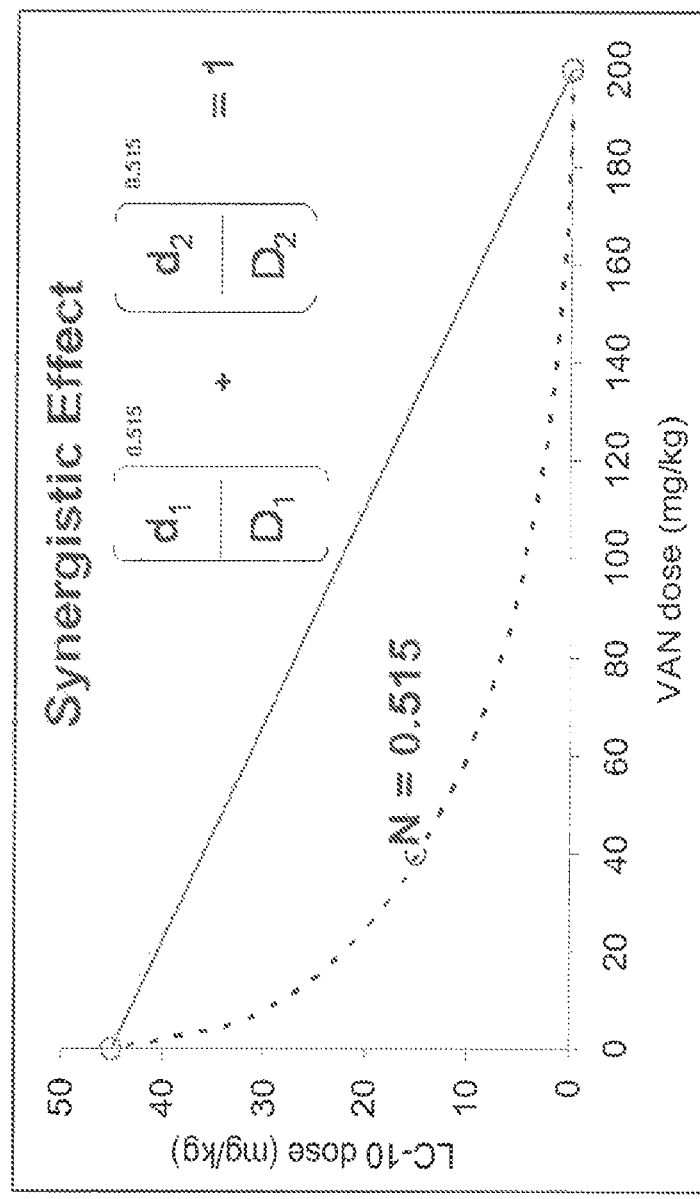
FIG. 27 is a graphical display of an isobologram analysis of synergy where N>1: antagonism, N=1: additive effect, N<1: synergy.

Treatment with vancomycin at 200 or 40 mg/kg/day resulted in survival of 90% and 43% respectively. Post infection monotherapy with LC-10 at 45 or 15 mg/kg protected 50% and 33% of the mice. (FIGS. 26A and B) Combination therapy with a single sub efficacious doses of LC-10 (15 mg/kg) and BID dosing of vancomycin at 40 mg/kg resulted in the survival of 75% of the animals. Ninety percent of the mice survived with the combination of 40 mg/kg/day vancomycin with 45 mg/kg LC-10. The differences in survival between monotherapy with vancomycin and combination therapy with either 15 mg/kg or 45 mg/kg LC-10 were statistically significant. (p=0.026 and p=0.015 respectively). Co-administration of vancomycin and LC-10 yielded a synergistic effect by an isobologram analysis (FIG. 27).

Example 14

Examples of Specific Embodiments

Provided hereafter are non-limiting examples of certain embodiments.

A1. An isolated antibody or antigen-binding fragment thereof that immunospecifically binds to a *Staphylococcus aureus* alpha toxin polypeptide and includes:
  (a) a VH CDR1 comprising an amino acid sequence identical to, or comprising 1, 2, or 3 amino acid residue substitutions relative to SEQ ID NO: 7, 10, 13 or 69;
  (b) a VH CDR2 comprising an amino acid sequence identical to, or comprising 1, 2, or 3 amino acid residue substitutions relative to SEQ ID NO: 8, 11, 14, 17, 70 or 75 and
  (c) a VH CDR3 comprising an amino acid sequence identical to, or comprising 1, 2, or 3 amino acid residue substitutions relative to SEQ ID NO: 9, 12, 15, 18, 16, 65, 66, 67, 71, 72, 76 or 78.

A2. The antibody or antigen binding fragment of embodiment A1, wherein the VH CDR1, VH CDR2 and VH CDR3 are represented by SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs 7, 8, and 67; SEQ ID NOs: 7, 8 and 78; SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

A3. An isolated antibody or antigen-binding fragment thereof, wherein the isolated antibody or antigen-binding fragment thereof immunospecifically binds to a *Staphylococcus aureus* alpha toxin polypeptide and includes:
  (a) a VH CDR1 comprising the amino acid sequence of SEQ ID NO: 7, 10, 13 or 69;
  (b) a VH CDR2 comprising the amino acid sequence of SEQ ID NO: 8, 11, 14, 17, 70 or 75;
  (c) a VH CDR3 comprising the amino acid sequence of SEQ ID NO: 9, 12, 15, 18, 16, 65, 66, 67, 71, 72, 76 or 78;
  (d) a VL CDR1 comprising the amino acid sequence of SEQ ID NO: 1 or 4;
  (e) a VL CDR2 comprising the amino acid sequence of SEQ ID NO: 2, 5, 73 or 77; and
  (f) a VL CDR3 comprising the amino acid sequence of SEQ ID NO: 3, 6, 64, 68 or 74.

A4. The antibody or antigen binding fragment of embodiment A3, wherein the VH CDR1, VH CDR2, VH CDR3, VL CDR1, VL CDR2 and VL CDR3 correspond to the amino acid sequences of SEQ ID NOs: 7, 8, 9, 1, 2 and 3; SEQ ID NOs: 10, 11, 12, 1, 2 and 3; SEQ ID NOs: 13, 14, 15, 4, 5 and 6; SEQ ID NOs: 7, 17, 18, 1, 2 and 3; SEQ ID NOs: 7, 8, 16, 1, 2 and 64; SEQ ID NOs: 7, 8, 65, 1, 2 and 64; SEQ ID NOs; 7, 8, 66, 1, 2 and 64; SEQ ID NOs: 7, 8, 67, 1, 2 and 68; SEQ ID NOs: 7, 8, 67, 1, 2 and 64; SEQ ID NOs: 7, 8, 78, 1, 2 and 64; SEQ ID NOs: 7, 8, 65, 1, 2 and 68; SEQ ID NOs: 69, 70, 71, 1, 2 and 68; SEQ ID NOs: 7, 8, 72, 1, 73 and 74; SEQ ID NOs: 69, 75, 71, 1, 2 and 68; SEQ ID NOs: 69, 75, 76, 1, 2 and 68; SEQ ID NOs: 69, 75, 76, 1, 77 and 74; SEQ ID NOs: 69, 70, 71, 1, 77 and 74

A5. The isolated antibody or antigen-binding fragment thereof of embodiment A1, wherein the isolated antibody or antigen-binding fragment thereof (i) comprises a VH chain domain comprising three CDRs and a VL chain domain comprising three CDRs; and (ii) immunospecifically binds to a *Staphylococcus aureus* alpha toxin polypeptide, wherein the three CDRs of the VH chain domain comprise:
  (a) a VH CDR1 comprising the amino acid sequence of SEQ ID NO: 7, 10, 13 or 69;
  (b) a VH CDR2 comprising the amino acid sequence of SEQ ID NO: 8, 11, 14, 17, 70 or 75; and
  (c) a VH CDR3 comprising the amino acid sequence of SEQ ID NO: 9, 12, 15, 18, 16, 65, 66, 67, 71, 72, 76 or 78.

A6. The antibody or antigen binding fragment of embodiment A5, wherein the VH CDR1, VH CDR2 and VH CDR3 correspond to the amino acid sequences of SEQ ID NOs: 7, 8 and 9; SEQ ID NOs: 10, 11 and 12; SEQ ID NOs: 13, 14 and 15; SEQ ID NOs: 7, 17 and 18; SEQ ID NOs: 7, 8 and 16; SEQ ID NOs: 7, 8 and 65; SEQ ID NOs: 7, 8 and 66; SEQ ID NOs 7, 8, and 67; SEQ ID NOs: 7, 8 and 78; SEQ ID NOs: 69, 70 and 71; SEQ ID NOs: 7, 8 and 72; SEQ ID NOs: 69, 75 and 71; SEQ ID NOs: 69, 75 and 76; or SEQ ID NOs: 69, 70 and 71.

A7. The isolated antibody or antigen-binding fragment thereof of embodiment A1, wherein the isolated antibody or antigen-binding fragment thereof (i) comprises a VH chain domain comprising three CDRs and a VL chain domain comprising three CDRs; and (ii) immunospecifically binds to a *Staphylococcus aureus* alpha toxin polypeptide, wherein the three CDRs of the VL chain domain comprise:
  (a) a VL CDR1 comprising the amino acid sequence of SEQ ID NO: 1 or 4;
  (b) a VL CDR2 comprising the amino acid sequence of SEQ ID NO: 2, 5, 73 or 77; and
  (c) a VL CDR3 comprising the amino acid sequence of SEQ ID NO: 3, 6, 64, 68 or 74.

A8. The antibody or antigen binding fragment of embodiment A7, wherein the VL CDR1, VL CDR2 and VL CDR3 correspond to the amino acid sequences of SEQ ID NOs: 1, 2 and 3; SEQ ID NOs: 4, 5 and 6; SEQ ID NOs: 1, 2 and 64; SEQ ID NOs: 1, 2 and 68; SEQ ID NOs: 1, 73 and 74; or SEQ ID NOs: 1, 77 and 74.

A9. An isolated antibody or antigen-binding fragment thereof that (i) immunospecifically binds to a *Staphylococcus aureus* alpha toxin polypeptide, (ii) comprises a heavy chain variable domain having at least 90% identity to the amino acid sequence of SEQ ID NO: 20, 22, 24, 26, 28, 41, 43, 45, 47, 49, 51, 53, 55, 57, 79, 59, 61, or 62 and (iii) comprises a light chain variable domain having at least 90% identity to the amino acid sequence of SEQ ID NO: 19, 21, 23, 25, 27, 42, 44, 46, 48, 50, 52, 54, 56, 58, 60 or 63.

A10. The antibody or antigen binding fragment of embodiment A9, wherein the VH and VL correspond to the amino acid sequences of SEQ ID NOs: 20 and 19; SEQ ID NOs; 22 and 21; SEQ ID NOs: 24 and 23; SEQ ID NOs: 26 and 25; SEQ ID NOs: 28 and 27; SEQ ID NOs: 41 and 42; SEQ ID NOs: 43 and 44; SEQ ID NOs: 45 and 46; SEQ ID NOs: 47 and 48; SEQ ID NOs: 47 and 48; SEQ ID NOs: 49 and 50; SEQ ID NOs: 51 and 52; SEQ ID NOs: 51 and 52; SEQ ID NOs: 53 and 54; SEQ ID NOs: 55 and 56; SEQ ID NOs: 57 and 58; SEQ ID NOs: 59 and 60; SEQ ID NOs: 61 and 58; SEQ ID NOs: 62 and 58; SEQ ID NOs: 62 and 63; SEQ ID NOs: 79 and 63.

A11. The isolated antibody or antigen-binding fragment thereof, wherein the isolated antibody or antigen-binding fragment thereof comprises a heavy chain variable domain of SEQ ID NO 20, 22, 24, 26, 28, 41, 43, 45, 47, 49, 51, 53, 55, 57, 79, 59, 61, or 62 and a light chain variable domain of SEQ ID NO: 19, 21, 23, 25, 27, 42, 44, 46, 48, 50, 52, 54, 56, 58, 60 or 63.

A12. The antibody or antigen binding fragment of embodiment A11, wherein the VH and VL correspond to the amino acid sequences of SEQ ID NOs: 20 and 19; SEQ ID NOs; 22 and 21; SEQ ID NOs: 24 and 23; SEQ ID NOs: 26 and 25; SEQ ID NOs: 28 and 27; SEQ ID NOs: 41 and 42; SEQ ID NOs: 43 and 44; SEQ ID NOs: 45 and 46; SEQ ID NOs: 47 and 48; SEQ ID NOs: 47 and 48; SEQ ID NOs: 49 and 50; SEQ ID NOs: 51 and 52; SEQ ID NOs: 51 and 52; SEQ ID NOs: 53 and 54; SEQ ID NOs: 55 and 56; SEQ ID NOs: 57 and 58; SEQ ID NOs: 59 and 60; SEQ ID NOs: 61 and 58; SEQ ID NOs: 62 and 58; SEQ ID NOs: 62 and 63; SEQ ID NOs: 79 and 63.

A13. The antibody or antigen binding fragment of any one of embodiments A1 to A12, wherein the isolated antibody or antigen-binding fragment thereof immunospecifically binds to a *Staphylococcus aureus* alpha toxin polypeptide and has one or more of the characteristics selected from the group consisting of:
  (a) affinity constant ($K_D$) for alpha toxin of about 13 nM or less;
  (b) binds to alpha toxin monomers, but does not inhibit binding of alpha toxin to alpha toxin receptor;
  (c) inhibits the formation of alpha toxin oligomers by at least 50%, 60%, 70%, 80%, 90%, or 95%;
  (d) reduces alpha toxin cytolytic activity by at least 50%, 60%, 70%, 80%, 90%, or 95% (e.g., as determined by cell lysis and hemolysis assays); and
  (e) reduces cell infiltration and pro-inflammatory cytokine release (e.g., in an animal pneumonia model).

A14. The antibody or antigen binding fragment of any one of embodiments A1 to A13, wherein the isolated antibody or antigen-binding fragment thereof comprises an additional agent.

A15. The antibody or antigen binding fragment of embodiment A14, wherein the additional agent is an antibiotic.

A16. The antibody or antigen binding fragment of embodiment A14, wherein the isolated antibody or antigen-binding fragment thereof is linked to the therapeutic agent via a linker.

A17. The antibody or antigen binding fragment of any one of embodiments A1 to A13, wherein the isolated antibody or antigen-binding fragment thereof further comprises a diagnostic agent.

A18. The antibody or antigen binding fragment of embodiment A17, wherein the diagnostic agent comprises an imaging agent.

A19. The antibody or antigen binding fragment of embodiment A17, wherein the diagnostic agent comprises a detectable label.

A20. The antibody or antigen binding fragment of embodiment A17, wherein the isolated antibody or antigen-binding fragment thereof is linked to the diagnostic agent via a linker.

A21. The antibody or antigen binding fragment of any one of embodiments A1 to A20, wherein the *Staphylococcus aureus* alpha toxin polypeptide is a native toxin polypeptide.

A22. The antibody or antigen binding fragment of any one of embodiments A1 to A20, wherein the *Staphylococcus aureus* alpha toxin polypeptide includes an amino acid sequence of SEQ ID NO: 39 or SEQ ID NO: 40.

A23. The antibody or antigen binding fragment of embodiment A13, wherein the cell is from the blood or the lung.

A24. The antibody or antigen binding fragment of embodiment A23, wherein the cell from the blood is a red blood cell.

A25. The antibody or antigen binding fragment of any one of embodiments, A13, A23 and A24, wherein the cell lysis is determined by a hemolytic in vitro assay or a lactate dehydrogenase in vitro assay.

A26. The antibody or antigen binding fragment of any one of embodiments A1 to A25, wherein the isolated antibody or antigen-binding fragment thereof immunospecifically binds to a *Staphylococcus aureus* alpha toxin polypeptide and comprises a VH CDR3 comprising an amino acid sequence identical to, or comprising 1, 2, or 3 amino acid residue substitutions relative to SEQ ID NO: 9, 12, 15, 18, 16, 65, 66, 67, 71, 72, 76 or 78, wherein the antibody or antigen-binding fragment neutralizes the *Staphylococcus aureus* alpha toxin polypeptide.

A27. The antibody or antigen binding fragment of any one of embodiments A1 to A26, wherein the isolated antibody or antigen-binding fragment thereof immunospecifically binds to a *Staphylococcus aureus* alpha toxin polypeptide and comprises a VL CDR3 comprising an amino acid sequence identical to, or comprising 1, 2, or 3 amino acid residue substitutions relative to, SEQ ID NO: 3, 6, 64, 68 or 74, wherein the antibody or antigen-binding fragment neutralizes the *Staphylococcus aureus* alpha toxin polypeptide.

A28. The antibody or antigen binding fragment of any one of embodiments A1 to A27, wherein the isolated antibody or antigen-binding fragment thereof immunospecifically binds to a *Staphylococcus aureus* alpha toxin polypeptide and comprises a VH CDR3 comprising an amino acid sequence identical to, or comprising 1, 2, or 3 amino acid residue substitutions relative to, SEQ ID NO: 9, 12, 15, 18, 16, 65, 66, 67, 71, 72, 76 or 78, wherein the antibody or antigen-binding fragment inhibits oligomerization of the *Staphylococcus aureus* alpha toxin polypeptide.

A29. The antibody or antigen binding fragment of any one of embodiments A1 to A28, wherein the isolated antibody or antigen-binding fragment thereof immunospecifically binds to a *Staphylococcus aureus* alpha toxin polypeptide and comprises a VL CDR3 comprising an amino acid sequence identical to, or comprising 1, 2, or 3 amino acid residue substitutions relative to, SEQ ID NO: 3, 6, 64, 68 or 74, wherein the antibody or antigen-binding fragment inhibits oligomerization of the *Staphylococcus aureus* alpha toxin polypeptide.

A30. The antibody or antigen binding fragment of any one of embodiments A13, A28 and A29, wherein the inhibition of oligomerization is determined by in vitro binding and/or electrophoretic mobility assay.

D1. A composition comprising the antibody or antigen binding fragment of any one of embodiments A1 to A30.

B1. A kit, comprising
(a) an antibody or antigen binding fragment of any one of embodiments A1 to A30 or the composition of embodiment D1;
(b) instructions for using the composition or directions for obtaining instructions for using the composition.

B2. The kit of embodiment B1, wherein the antibody in the composition is linked to a solid support.

B3. The kit of embodiment B2, wherein the solid support is a bead.

B4. The kit of embodiment B3, wherein the bead is a sepharose bead.

B5. The kit of any one of embodiments B1 to B4, wherein the instructions for use include one or more of isolating, purifying, detecting and quantifying a *Staphylococcus aureus* alpha toxin polypeptide.

B6. The kit of any one of embodiments B1 to B5 comprising a buffer, a solid support or a buffer and a solid support.

B7. The kit of embodiment B6, wherein the solid support is one or more of a bead, filter, membrane and multiwall plate.

B8. The kit of embodiment B6, which includes a buffer and membrane suitable for a Western blot.

B9. The kit of embodiment B6, which includes a loading buffer and an elution buffer.

B10. The kit of embodiment B6, which includes a buffer suitable for an enzyme-linked immunosorbant assay (ELISA).

C1. A method for preventing, treating or managing pneumonia in a subject, comprising:
administering an antibody or antigen binding fragment of any one of embodiments A1 to A30 or the composition of embodiment D1 to a subject in need thereof in an amount effective for preventing, treating or managing the pneumonia.

C2. The method of embodiment C1, which is a method for preventing pneumonia.

C3. The method of embodiment C1 or C2, wherein the antibody or antigen-binding fragment thereof immunospecifically binds to a conformational epitope within SEQ ID NO: 39.

C4. A method for preventing, treating or managing a skin infection condition in a subject, comprising: administering an antibody or antigen-binding fragment thereof that immunospecifically binds to a *Staphylococcus aureus* alpha toxin polypeptide to a subject in need thereof in an amount effective for preventing, treating or managing the skin infection condition.

C5. The method of embodiment C4, wherein the skin infection condition is dermonecrosis.

C6. The method of embodiment C4 or C5, wherein the skin infection condition includes a *Staphylococcus aureus* infection of the skin.

C7. The method of any one of embodiments C4 to C6, which is a method for preventing the skin infection condition.

C8. A method for preventing, treating or managing a condition associated with *Staphylococcus aureus* infection, comprising administering an antibody or antigen-binding fragment thereof that immunospecifically binds to a *Staphylococcus aureus* alpha toxin polypeptide to a subject in need thereof in an amount effective to reduce oligomerization of the toxin polypeptide.

C9. The method of embodiment C8, which is a method for preventing the condition associated with *Staphylococcus aureus* infection.

C10. A method for preventing, treating or managing a condition associated with *Staphylococcus aureus* infection, comprising administering an antibody or antigen-binding fragment thereof that immunospecifically binds to a *Staphylococcus aureus* alpha toxin polypeptide to a subject in need thereof in an amount effective to reduce erythrocyte lysis.

C11. The method of embodiment C10, which is a method for preventing the condition associated with *Staphylococcus aureus* infection.

C12. The method of embodiment C10 or C11, wherein the erythrocyte is a cell from the blood or the lung.

C13. The method of any one of embodiments C4 to C12, wherein the antibody or antigen-binding fragment thereof has one or more of the characteristics selected from the group consisting of:
(a) affinity constant ($K_D$) for alpha toxin of about 13 nM or less;
(b) binds to alpha toxin monomers, but does not inhibit binding of alpha toxin to alpha toxin receptor;

(c) inhibits the formation of alpha toxin oligomers by at least 50%, 60%, 70%, 80%, 90%, or 95%;
(d) reduces alpha toxin cytolytic activity by at least 50%, 60%, 70%, 80%, 90%, or 95% (e.g., as determined by cell lysis and hemolysis assays); and
(e) reduces cell infiltration and pro-inflammatory cytokine release (e.g., in an animal pneumonia model).

C14. The method of embodiment C13, wherein the antibody or antigen-binding fragment thereof immunospecifically binds to a conformational epitope within SEQ ID NO: 39.

C15. The method of any one of embodiments C1 to C14, wherein the antibody or antigen binding fragment or composition administered to the subject is according to any one of embodiments A1 to A30 or D1.

C16. A method, comprising:
administering an antibody or antigen binding fragment of any one of embodiments A1 to A30 or the composition of embodiment D1 to cells; and
detecting the presence, absence or amount of a biological effect associated with the administration of the composition to the cells.

C17. A method, comprising:
administering an antibody or antigen binding fragment of any one of embodiments A1 to A30 or the composition of embodiment D1 to a subject; and
detecting the presence, absence or amount of a biological effect in the subject associated with the administration of the composition.

C18. A method, comprising:
administering an antibody or antigen binding fragment of any one of embodiments A1 to A30 or the composition of embodiment D1 to a subject; and
monitoring the condition of the subject.

C19. A method for neutralizing a *Staphylococcus aureus* alpha toxin polypeptide by administering to a subject in need thereof an effective amount of an antibody or antigen binding fragment of any one of embodiments A1 to A30 or the composition of embodiment D1 to neutralize the toxin polypeptide.

C20. A method of preventing, treating, or managing a condition mediated by a *Staphylococcus aureus* alpha toxin in a subject in need thereof, the method comprising administering to the subject an effective amount of an antibody or antigen binding fragment of any one of embodiments A1 to A30 or the composition of embodiment D1 to prevent, treat or manage the condition.

C21. A method for treating, preventing or alleviating the symptoms of a disorder mediated by *Staphylococcus aureus* alpha toxin in a subject in need thereof, comprising administering an effective amount of an antibody or antigen binding fragment of any one of embodiments A1 to A30 or the composition of embodiment D1 to the subject to treat, prevent or alleviate the symptoms.

C22. A method for diagnosing a condition mediated by a *Staphylococcus aureus* alpha toxin in a subject, comprising selecting a subject in need of diagnosis and administering to the subject a diagnostically effective dose of an antibody or antigen binding fragment of any one of embodiments A1 to A30 or the composition of embodiment D1.

C23. The method of any one of embodiments C1 to C22, wherein the subject is a domestic animal.

C24. The method of any one of embodiments C1 to C22, wherein the subject is a human.

C25. A method of inhibiting the formation of *Staphylococcus aureus* alpha toxin oligomers by at least 50%, 60%, 70%, 80%, 90% or 95% with an antibody or antigen binding fragment of any one of embodiments A1 to A30 or the composition of embodiment D1.

C26. The method of C25, where the inhibition of the formation of *Staphylococcus aureus* alpha toxin oligomers inhibits formation of the active pore forming complex.

C27. A method of reducing *Staphylococcus aureus* alpha toxin cytolytic activity by at least 50%, 60%, 70%, 80%, 90%, or 95% with an antibody or antigen binding fragment of any one of embodiments A1 to A30 or the composition of embodiment D1, wherein the cytolytic activity is determined by a cell lysis and/or hemolysis assays.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects herein. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. It should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments herein are set forth in the claim(s) that follow(s).

What is claimed is:

1. An isolated antibody or antigen-binding fragment thereof, wherein the isolated antibody or antigen-binding fragment thereof immunospecifically binds to a *Staphylococcus aureus* alpha toxin polypeptide and comprises:
   (a) a VH CDR1 comprising the amino acid sequence of SEQ ID NO: 7, 10, 13 or 69;
   (b) a VH CDR2 comprising the amino acid sequence of SEQ ID NO: 8, 11, 14, 17, 70 or 75;
   (c) a VH CDR3 comprising the amino acid sequence of SEQ ID NO: 9, 12, 15, 18, 16, 65, 66, 67, 71, 72, 76 or 78;
   (d) a VL CDR1 comprising the amino acid sequence of SEQ ID NO: 1 or 4;
   (e) a VL CDR2 comprising the amino acid sequence of SEQ ID NO: 2, 5, 73 or 77; and
   (f) a VL CDR3 comprising the amino acid sequence of SEQ ID NO: 3, 6, 64, 68 or 74.

2. The antibody or antigen binding fragment of claim 1, wherein the VH CDR1, VH CDR2, VH CDR3, VL CDR1, VL CDR2 and VL CDR3 correspond to the amino acid sequences of SEQ ID NOs: 7, 8, 9, 1, 2 and 3; SEQ ID NOs: 10, 11, 12, 1, 2 and 3; SEQ ID NOs: 13, 14, 15, 4, 5 and 6; SEQ ID NOs: 7, 17, 18, 1, 2 and 3; SEQ ID NOs: 7, 8, 16, 1, 2 and 64; SEQ ID NOs: 7, 8, 65, 1, 2 and 64; SEQ ID NOs; 7, 8, 66, 1, 2 and 64; SEQ ID NOs: 7, 8, 67, 1, 2 and 68; SEQ ID NOs: 7, 8, 67, 1, 2 and 64; SEQ ID NOs: 7, 8, 78, 1, 2 and 64; SEQ ID NOs: 7, 8, 65, 1, 2 and 68; SEQ ID NOs: 69, 70, 71, 1, 2 and 68; SEQ ID NOs: 7, 8, 72, 1, 73 and 74; SEQ ID NOs: 69, 75, 71, 1, 2 and 68; SEQ ID NOs: 69, 75, 76, 1, 2 and 68; SEQ ID NOs: 69, 75, 76, 1, 77 and 74; SEQ ID NOs: 69, 70, 71, 1, 77 and 74.

3. The antibody or antigen binding fragment of claim 1, wherein the isolated antibody or antigen-binding fragment thereof immunospecifically binds to a *Staphylococcus aureus* alpha toxin polypeptide and has one or more of the characteristics selected from the group consisting of: (a) affinity constant (KD) for alpha toxin of about 13 nM or less; (b) binds to alpha toxin monomers, but does not inhibit binding of alpha toxin to alpha toxin receptor; (c) inhibits the formation of alpha toxin oligomers by at least 50%, 60%, 70%, 80%, 90%, or 95%; (d) reduces alpha toxin cytolytic activity by at least 50%, 60%, 70%, 80%, 90%, or 95% as determined by cell lysis and hemolysis assays; and (e) reduces cell infiltration and pro-inflammatory cytokine release.

4. The antibody or antigen binding fragment of claim 1, wherein the isolated antibody or antigen-binding fragment thereof comprises an additional agent, wherein the additional agent is an antibiotic.

5. A composition comprising the antibody or antigen binding fragment of claim 1.

6. A kit, comprising
   (a) an antibody or antigen binding fragment of claim 1;
   (b) instructions for using the antibody or antigen binding fragment or directions for obtaining instructions for using the antibody or antigen binding fragment.

7. The antibody or antigen-binding fragment of claim 4, wherein the antibiotic is vancomycin.

8. The isolated antibody or antigen-binding fragment thereof of claim 1, further comprising an Fc variant region.

9. The isolated antibody or antigen-binding fragment thereof of claim 8, wherein the isolated antibody comprises SEQ ID NO: 91 and SEQ ID NO: 92.

* * * * *